United States Patent
Biediger et al.

(10) Patent No.: US 6,723,711 B2
(45) Date of Patent: Apr. 20, 2004

(54) PROPANOIC ACID DERIVATIVES THAT INHIBIT THE BINDING OF INTEGRINS TO THEIR RECEPTORS

(75) Inventors: Ronald J. Biediger, Houston, TX (US); Brian Dupre, Houston, TX (US); Linda K. Hamaker, Houston, TX (US); George W. Holland, Houston, TX (US); Jamal M. Kassir, Stafford, TX (US); Wen Li, Pearland, TX (US); Robert V. Market, Pearland, TX (US); Noel Nguyen, Houston, TX (US); Ian L. Scott, Delanson, NY (US); Chengde Wu, Pearland, TX (US); E. Radford Decker, Houston, TX (US)

(73) Assignee: Texas Biotechnology Corporation, Houston, TX (US)

( * ) Notice: Subject to any disclaimer, the term of this patent is extended or adjusted under 35 U.S.C. 154(b) by 266 days.

(21) Appl. No.: 09/973,414

(22) Filed: Oct. 9, 2001

(65) Prior Publication Data

US 2003/0199692 A1 Oct. 23, 2003

Related U.S. Application Data

(63) Continuation-in-part of application No. 09/706,996, filed on Nov. 6, 2000, which is a continuation-in-part of application No. 09/565,507, filed on May 5, 2000.
(60) Provisional application No. 60/170,441, filed on Dec. 10, 1999, and provisional application No. 60/132,967, filed on May 7, 1999.

(51) Int. Cl.$^7$ .................. C07D 213/64; C07D 239/36; A61K 31/4412; A61K 31/513; A61D 11/06
(52) U.S. Cl. .................. 514/86; 514/89; 514/274; 514/317; 514/318; 514/326; 514/327; 514/336; 514/338; 514/351; 544/243; 544/316; 546/24; 546/192; 546/193; 546/243; 546/268.4; 546/271.4; 546/280.4; 546/300
(58) Field of Search .................. 514/86, 89, 274, 514/317, 318, 326, 327, 336, 338, 351; 544/243, 316; 546/24, 192, 193, 243, 268.4, 271.4, 286.4, 300

(56) References Cited

U.S. PATENT DOCUMENTS

| | | |
|---|---|---|
| 5,192,746 A | 3/1993 | Lobl et al. |
| 5,455,243 A * | 10/1995 | Duggan et al. .............. 514/218 |
| 5,484,946 A | 1/1996 | Abood et al. |
| 5,510,332 A | 4/1996 | Kogan et al. |
| 5,521,179 A | 5/1996 | Bernstein et al. |
| 5,656,627 A | 8/1997 | Bemis et al. |
| 5,710,153 A | 1/1998 | Ohmoto et al. |
| 5,721,366 A | 2/1998 | Abood et al. |
| 5,756,466 A | 5/1998 | Bemis et al. |
| 5,770,573 A | 6/1998 | Arrhenius et al. |
| 5,821,231 A | 10/1998 | Arrhenius et al. |
| 5,847,135 A | 12/1998 | Bemis et al. |
| 5,852,045 A * | 12/1998 | Ashew et al. .............. 514/318 |
| 5,874,424 A | 2/1999 | Batchelor et al. |
| 5,936,065 A | 8/1999 | Arrhenius et al. |
| 5,981,546 A * | 11/1999 | Duggan et al. .............. 514/300 |

FOREIGN PATENT DOCUMENTS

| | | |
|---|---|---|
| AU | 92421/98 | 10/1999 |
| EP | 0 341 915 | 5/1989 |
| EP | 0422 938 A1 | 4/1991 |
| EP | 0 512 831 A1 | 7/1992 |
| EP | 0 842 943 A2 | 10/1997 |
| EP | 0 761 680 A2 | 12/1997 |

(List continued on next page.)

OTHER PUBLICATIONS

Structure–Based Design of Non–Peptidic Pyridone Aldehydes As Inhibitors of Interleukin–1β Converting Enzyme, Biorganic & Medicinal Chemistry Letters, vol. 7, No. 17, pp. 2181–2186 (1997).
Pyridone–Based Peptidomimetic Inhibitors of Interleukin–1β Converting Enzyme (ICE), Biorganic & Medicinal Chemistry Letters, vol. 7, No. 10, pp. 1337–1342 (1997).
PeptidomimeticAminomethylene Ketone Inhibitors of Interleukin–1β Converting Enzyme (ICE), Biorganic & Medicinal Chemistry Letters, vol.87, pp. 959–964 (1998).
Walters, D. Eric, et al., "Genetically Evolved Receptor Models: A Computational Approach to Construction of Receptor Models", Journal of Medical Chemistry, 37(16):2527–2536 (1994).

Primary Examiner—Mukund J. Shah
Assistant Examiner—Thomas McKenzie
(74) Attorney, Agent, or Firm—Wood, Phillips, Katz, Clark & Mortimer

(57) ABSTRACT

A compound of the structure

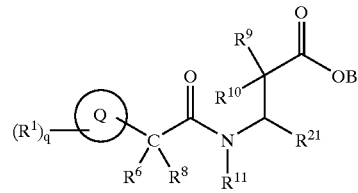

wherein circle Q is a ring selected from the group consisting of

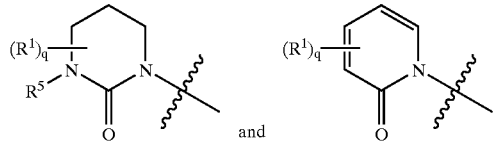

A method for the inhibition of the binding of $α_4β_1$ integrin to its receptors, for example VCAM-1(vascular cell adhesion molecule-1) and fibronectin; pharmaceutically active compositions comprising these compounds; and the use of these compounds for the control or prevention of diseases states in which $α_4β_1$ is involved are also disclosed.

13 Claims, No Drawings

FOREIGN PATENT DOCUMENTS

| | | |
|---|---|---|
| EP | 0 903 353 A1 | 3/1999 |
| GB | 2312895 A * | 11/1997 |
| JP | 09/031060 A2 * | 2/1997 |
| WO | WO 94/22820 | 10/1994 |
| WO | WO 95/15973 | 6/1995 |
| WO | WO 96/06108 | 2/1996 |
| WO | WO 96/22966 | 8/1996 |
| WO | WO 97/24122 A1 * | 7/1997 |
| WO | WO 98/16502 | 9/1997 |
| WO | WO 98/04247 | 2/1998 |
| WO | WO 98/04913 | 2/1998 |
| WO | WO 98/04247 | 5/1998 |
| WO | WO 98/22494 | 5/1998 |
| WO | WO 98/50420 | 12/1998 |
| WO | WO 99/06434 | 2/1999 |
| WO | WO 99/10313 | 3/1999 |
| WO | WO 99/20272 | 4/1999 |
| WO | WO 99/24398 | 5/1999 |
| WO | WO 00/17197 | 3/2000 |
| WO | WO 00/21920 | 4/2000 |
| WO | WO 00/61631 | 10/2000 |
| WO | WO 01/42216 A2 * | 12/2000 |

* cited by examiner

PROPANOIC ACID DERIVATIVES THAT INHIBIT THE BINDING OF INTEGRINS TO THEIR RECEPTORS

CROSS-REFERENCE TO RELATED APPLICATIONS

This application is a continuation-in-part of U.S. patent application Ser. No. 09/706,996, filed Nov. 6, 2000, which is a continuation-in-part of U.S. patent application Ser. No. 09/565,507, filed May 5, 2000, which claims the benefit of U.S. Provisional Patent Application Serial Nos. 60/132,967, filed May 7, 1999 and 60/170,441, filed Dec. 10, 1999.

FIELD OF THE INVENTION

This invention is directed generally to the inhibition of the binding of $\alpha_4\beta_1$ integrin to its receptors, for example VCAM-1 (vascular cell adhesion molecule-1) and fibronectin. The invention also relates to compounds that inhibit this binding, to pharmaceutically active compositions comprising such compounds and to the use of such compounds either as above, or in formulations for the control or prevention of disease states in which $\alpha_4\beta_1$ is involved.

BACKGROUND OF THE INVENTION

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells recognize the invaded or damaged tissue, bind to the wall of the capillary and migrate through the capillary into the affected tissue. These events are mediated by a family of proteins called cell adhesion molecules.

There are three main types of white blood cells: granulocytes, monocytes and lymphocytes. The integrin $\alpha_4\beta_1$ (also called VLA-4 for very late antigen-4) is a heterodimeric protein expressed on the surface of monocytes, lymphocytes and two subclasses of granulocytes: eosinophils and basophils. This protein plays a key role in cell adhesion through its ability to recognize and bind VCAM-1 and fibronectin, proteins associated with the endothelial cells that line the interior wall of capillaries.

Following infection or damage of tissue surrounding a capillary, endothelial cells express a series of adhesion molecules, including VCAM-1, that are critical for binding the white blood cells that are necessary for fighting infection. Prior to binding to VCAM-1 or fibronectin, the white blood cells initially bind to certain adhesion molecules to slow their flow and allow the cells to "roll" along the activated endothelium. Monocytes, lymphocytes, basophils and eosinophils are then able to firmly bind to VCAM-1 or fibronectin on the blood vessel wall via the $\alpha_4\beta_1$ integrin. There is evidence that such interactions are also involved in transmigration of these white blood cells into the damaged tissue, as well as the initial rolling event itself.

Although white blood cell migration to the site of injury helps fight infection and destroy foreign material, in many instances this migration can become uncontrolled, with white blood cells flooding to the scene, causing widespread tissue damage. Compounds capable of blocking this process, therefore, may be beneficial as therapeutic agents. Thus, it would be useful to develop inhibitors that would prevent the binding of white blood cells to VCAM-1 and fibronectin.

Some of the diseases that might be treated by the inhibition of $\alpha_4\beta_1$ binding include, but are not limited to, atherosclerosis, rheumatoid arthritis, asthma, allergy, multiple sclerosis, lupus, inflammatory bowel disease, graft rejection, contact hypersensitivity, and type I diabetes. In addition to being found on some white blood cells, $\alpha_4\beta_1$ is also found on various cancer cells, including leukemia, melanoma, lymphoma and sarcoma cells. It has been suggested that cell adhesion involving $\alpha_4\beta_1$ may be involved in the metastasis of certain cancers. Inhibitors of $\alpha_4\beta_1$ binding may, therefore, also be useful in the treatment of some forms of cancer.

The isolation and purification of a peptide which inhibits the binding of $\alpha_4\beta_1$ to a protein is disclosed in U.S. Pat. No. 5,510,332. Peptides which inhibit binding are disclosed in WO 95/15973, EP 0 341 915, EP 0 422 938 A1, U.S. Pat. No. 5,192,746 and WO 96/06108. Novel compounds which are useful for inhibition and prevention of cell adhesion and cell adhesion-mediated pathologies are disclosed in WO 96/22966, WO 98/04247 and WO 98/04913.

It is therefore an object of the invention to provide novel compounds which are inhibitors of $\alpha_4\beta_1$ binding, and pharmaceutical compositions including such novel compounds.

BRIEF SUMMARY OF THE INVENTION

The invention is directed to novel compounds of Formula I as follows:

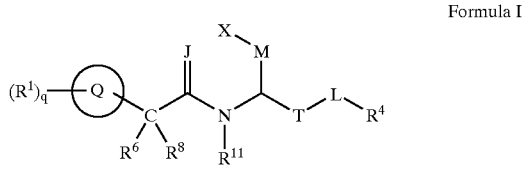

Formula I wherein circle Q represents one or more rings;

q is an integer of zero to six;

M is selected from the group consisting of —C(R$^9$)(R$^{10}$)— and —(CH$_2$)$_u$—, wherein u is an integer of from 0 to 3;

J is selected from the group consisting of —O—, —S— and —NR$^{12}$—;

T is selected from the group consisting of —C(O)— and —(CH$_2$)$_b$— wherein b is an integer of from 0 to 3;

L is selected from the group consisting of —O—, —NR$^{13}$—, —S—, and —(CH$_2$)$_v$— wherein v is an integer of 0 or 1;

X is selected from the group consisting of —CO$_2$B, —PO$_3$H$_2$, —SO$_3$H, —SO$_2$NH$_2$, —SO$_2$NHCOR$^{14}$, —OPO$_3$H$_2$, —C(O)NHC(O)R$^{15}$, —C(O)NHSO$_2$R$^{16}$, tetrazolyl, oxazolyl and hydroxyl;

R$^{11}$, R$^{12}$ and R$^{13}$ are each independently selected from the group consisting of hydrogen, alkyl, alkenyl, alkynyl, hydroxyalkyl, aliphatic acyl, alkynylamino, alkoxycarbonyl, heterocycloyl, —CH═NOH, haloalkyl, alkoxyalkyl, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups; and, B, R$^1$, R$^4$, R$^6$, R$^8$, R$^9$, R$^{10}$, R$^{14}$, R$^{15}$ and R$^{16}$ at each occurrence are independently selected from the group consisting of hydrogen, halogen, alkyl, alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)—C(O)$C_1$-$C_3$ alkyl), —NHC(O)N($C_1$-$C_3$ alkyl)C(O)—NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl and —C(O)NH(benzyl) groups;

wherein B, $R^1$, $R^4$, $R^6$, $R^8$, $R^9$, $R^{10}$, $R^{11}$, $R^{12}$, $R^{13}$, $R^{14}$, $R^{15}$ and $R^{16}$ are unsubstituted or substituted with at least one electron donating or electron withdrawing group;

wherein when L is —$NR^{13}$—, $R^4$ and $R^{13}$ taken together may form a ring;

and wherein $R^6$ and $R^8$ taken together may form a ring;

and wherein when M is —C($R^9$)($R^{10}$)—, $R^9$ and $R^{10}$ taken together may form a ring;

or a pharmaceutically acceptable salt thereof.

For Formula I, presently preferred compounds may have circle Q as an aryl, cycloalkyl, biaryl or heterocyclyl ring.

More specifically, the compounds of this invention may be described by Formula II below Formula II

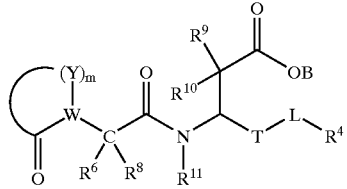

wherein Y, at each occurrence, is independently selected from the group consisting of C(O), N, $CR^7$, C($R^2$)($R^3$), $NR^5$, CH, O and S;

m is an integer of from 2 to 5;

W is selected from the group consisting of C, N and $CR^{22}$;

T is selected from the group consisting of C(O) and $(CH_2)_b$ wherein b is an integer of 0 to 3;

L is selected from the group consisting of O, $NR^{13}$, S, and $(CH_2)_n$ wherein n is an integer of 0 or 1;

$R^5$, $R^{11}$ and $R^{13}$ at each occurrence, are each independently selected from the group consisting of hydrogen, alkyl, alkenyl, alkynyl, hydroxyalkyl, aliphatic acyl, alkynylamino, alkoxycarbonyl, heterocycloyl, —CH=NOH, haloalkyl, alkoxyalkyl, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups; and, B, $R^2$, $R^3$, $R^4$, $R^6$, $R^7$, $R^8$, $R^9$, $R^{10}$ and $R^{22}$ are each independently selected from the group consisting of hydrogen, halogen, alkyl, alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)—C(O)($C_1$-$C_3$ alkyl), —NHC(O)N($CH_1$-$C_3$ alkyl)C(O)—NH($C_1$-$C_3$ alkyl), —NHC(O)NH($CH_1$-$C_6$ alkyl), —$NHSO_2$($C_1$-$C_3$ alkyl), —$NHSO_2$(aryl), alkoxyalkyl, alkylamino, alkenylamino, di(C, —$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl and —C(O)NH(benzyl) groups;

wherein B, $R^2$, $R^3$, $R^4$, $R^5$, $R^6$, $R^7$, $R^8$, $R^9$, $R^{10}$, $R^{11}$, $R^{13}$ and $R^{22}$ are unsubstituted or substituted with at least one electron donating or electron withdrawing group;

and wherein when L is —$NR^{13}$—, $R^4$ and $R^{13}$ taken together may form a ring; and wherein $R^6$ and $R^8$ taken together may form a ring; and wherein $R^9$ and $R^{10}$ taken together may form a ring;

or a pharmaceutically acceptable salt thereof.

More specifically, the compounds of this invention may be described by Formula III below Formula III

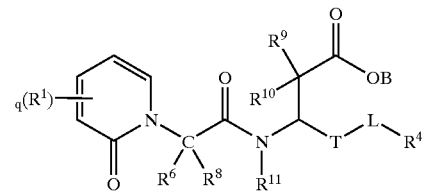

wherein q is an integer of zero to four;

T is selected from the group consisting of C(O) and $(CH_2)_b$ wherein b is an integer of 0 to 3;

L is selected from the group consisting of O, $NR_{13}$, S, and $(CH_2)_n$ wherein n is an integer of 0 or 1;

$R^{11}$ and $R^{13}$ are each independently selected from the group consisting of hydrogen, alkyl, alkenyl, alkynyl, hydroxyalkyl, aliphatic acyl, alkynylamino, alkoxycarbonyl, heterocycloyl, —CH=NOH, haloalkyl, alkoxyalkyl, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups; and, B, $R^1$, $R^4$, $R^6$, $R^8$, $R^9$ and $R^{10}$ at each occurrence are each independently selected from the group consisting of hydrogen, halogen, alkyl, alkenyl, alkynyl, alkoxy, alkenoxy, alkynoxy, thioalkoxy, hydroxyalkoxy, aliphatic acyl, —$CF_3$,—$CO_2H$, —SH, —CN, —$NO_2$, —$NH_2$, —OH, alkynylamino, alkoxycarbonyl, heterocycloyl, carboxy, —N($C_1$-$C_3$ alkyl)—C(O)$C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$–$C_3$)amino, —C(O)O—($C_1$–$C_3$)alkyl, —C(O)NH($C_1$–$C_3$)alkyl, —C(O)N($C_1$–$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$–$C_3$ alkyl), —SO$_3$—($C_1$–$C_3$ alkyl), sulfonamido, carbamate, aryloxyalkyl and —C(O)NH(benzyl) groups;

wherein B, $R^1$, $R^4$, $R^6$, $R^8$, $R^9$, $R^{10}$, $R^{11}$ and $R^{13}$ are unsubstituted or substituted with at least one electron donating or electron withdrawing group;

and wherein when L is —NR$^{13}$—, $R^4$ and $R^{13}$ taken together may form a ring;

and wherein $R^6$ and $R^8$ taken together may form a ring;

and wherein $R^9$ and $R^{10}$ taken together may form a ring;

or a pharmaceutically acceptable salt thereof.

Presently preferred compounds of Formula III have q as one or two; $R^1$ at each occurrence independently as aralkyl or alkyl; $R^6$ as alkyl; B, $R^8$, $R^9$, $R^{10}$ and $R^{11}$ ach independently as hydrogen, T as —(CH$_2$)$_b$— wherein b is zero; L as —(CH$_2$)$_n$— wherein n is zero and $R^4$ as aryl.

More specifically, the compounds of this invention may be described by Formula IV below Formula IV

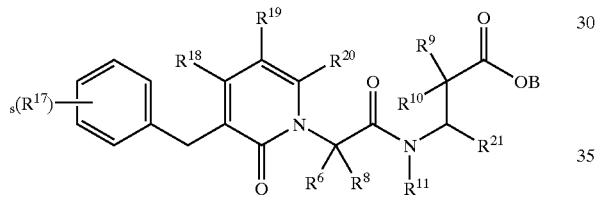

wherein s is an integer of zero to five;

$R^{21}$ is selected from the group consisting of aryl, alkyheterocyclyl, heterocyclylalkyl, heterocycloyl, aralkyl, alkylaryl, alkyl, aroyl, aryloxy, cycloalkyl, cycloalkenyl, cycloalkynyl, biaryl, arylamino, thioaryl and diarylamino;

B, $R^6$, $R^8$, $R^9$, $R^{10}$, $R^{17}$, $R^{18}$, $R^{19}$ and $R^{20}$ at each occurrence are each independently selected from the group consisting of hydrogen, halogen, alkyl, alkenyl, alkynyl, alkoxy, alkenoxy, alkynoxy, thioalkoxy, hydroxyalkoxy, aliphatic acyl, —CF$_3$, —CO$_2$H, —SH, —CN, NO$_2$, —NH$_2$, —OH, alkynylamino, alkoxycarbonyl, heterocycloyl, carboxy, —N($C_1$–$C_3$ alkyl)—C(O)$C_1$–$C_3$ alkyl), —NHC(O)N($C_1$–$C_3$ alkyl)C(O)NH($C_1$–$C_3$ alkyl), —NHC(O)NH($C_1$–$C_6$ alkyl), —NHSO$_2$($C_1$–$C_3$ alkyl), —NHSO$_2$(aryl), alkoxyalkyl, alkylamino, alkenylamino, di($C_1$–$C_3$)amino, —C(O)O—($C_1$–$C_3$)alkyl, —C(O)NH($C_1$–$C_3$)alkyl, —C(O)N($C_1$–$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$–$C_3$ alkyl), —SO$_3$—($C_1$–$C_3$ alkyl), sulfonamido, carbamate, aryloxyalkyl and —C(O)NH(benzyl) groups; and, $R^{11}$ is selected from the group consisting of hydrogen, alkyl, alkenyl, alkynyl, hydroxyalkyl, aliphatic acyl, alkynylamino, alkoxycarbonyl, heterocycloyl, —CH=NOH, haloalkyl, alkoxyalkyl, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups;

wherein B, $R^6$, $R^8$, $R^9$, $R^{10}$, $R^{11}$, $R^{17}$, $R^{18}$, $R^{19}$, $R^{20}$ and $R^{21}$ are unsubstituted or substituted with at least one electron donating or electron withdrawing group;

and wherein $R^6$ and $R^8$ taken together may form a ring;

and wherein $R^9$ and $R^{10}$ taken together may form a ring;

and wherein $R^{18}$ and $R^{19}$ taken together may form a ring;

and wherein $R^{19}$ and $R^{20}$ taken together may form a ring;

or a pharmaceutically acceptable salt thereof.

Presently preferred compounds of Formula IV have B, $R^8$, $R^9$, $R^{10}$, $R^{11}$, $R^{18}$ and $R^{20}$ each independently as hydrogen, $R^6$ and $R^{19}$ each independently as alkyl; s as an integer of zero to three; $R^{17}$ at each occurrence independently as halogen, alkyl, haloalkyl, —CF$_3$, alkoxy or —OH; and $R^{21}$ as aryl. A presently most preferred compound of Formula IV has s as zero; $R^6$ as butyl; B, $R^8$, $R^9$, $R^{10}$, $R^{11}$, $R^{18}$ and $R^{20}$ each independently as hydrogen; and $R^{21}$ as 1,3-benzodioxol-5-yl.

Compounds of the present invention may also be described by Formula V, shown below.

Formula V

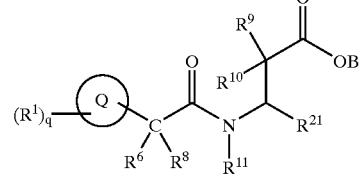

wherein circle Q is a ring selected from the group consisting of q is an integer of zero to four;

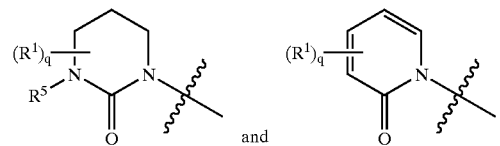

and

B, $R^1$, $R^6$, $R^8$, $R^9$ and $R^{10}$ are each independently selected from the group consisting of hydrogen, halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, NO$_2$, —NH$_2$, —OH, alkynylamino, alkoxycarbonyl, heterocycloyl, carboxy, —N($C_1$–$C_3$ alkyl)—C(O)$C_1$–$C_3$ alkyl), —NHC(O)NH($C_1$–$C_3$ alkyl), —NHC(O)N($C_1$–$C_3$ alkyl)C(O)NH($C_1$–$C_3$ alkyl), —NHSO$_2$($C_1$–$C_3$ alkyl), —NHSO$_2$(aryl), alkoxyalkyl, —$C_1$–$C_3$ alkylamino, alkenylamino, alkynylamino, di($C_1$–$C_3$ alkyl)amino, —C(O)O—($C_1$–$C_3$ alkyl), —C(O)NH—($C_1$–$C_3$ alkyl), —CH=NOH, —PO$_3$H$_2$, —OPO$_3$H$_2$, —C(O)N($C_1$–$C_3$ alkyl)$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, aryloxyalkyl, carboxyl, carbamate and —C(O)NH(benzyl);

$R^5$ and $R^{11}$ are each independently selected from the group consisting of hydrogen, alkyl, alkenyl, alkynyl, hydroxyalkyl, aliphatic acyl, alkynylamino, alkoxycarbonyl, heterocycloyl, —CH=NOH, haloalkyl, alkoxyalkyl, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups; and, $R^{21}$ is selected from the group consisting of aryl, alkyheterocyclyl, heterocyclylalkyl, heterocycloyl, aralkyl, alkylaryl, alkyl, aroyl, aryloxy, cycloalkyl, cycloalkenyl, cycloalkynyl, biaryl, arylamino, thioaryl and diarylamino;

wherein B, $R^1$, $R^5$, $R^6$, $R^8$, $R^9$, $R^{10}$, $R^{11}$ and $R^{21}$ are unsubstituted or substituted with at least one electron donating or electron withdrawing group;

and wherein $R^6$ and $R^8$ taken together may form a ring; and wherein $R^9$ and $R^{10}$ taken together may form a ring; or a pharmaceutically acceptable salt thereof.

Presently preferred compounds of Formula V have B, $R^6$, $R^8$, $R^9$, $R^{10}$ and $R^{11}$ each independently as hydrogen and alkyl, $R^1$ and $R^5$, at each occurrence, independently as hydrogen, 2-thienylmethyl, benzyl or methyl and $R^{21}$ as aryl.

Presently preferred compounds include (3S)-(1,3-benzodioxol-5-yl)-3-(((2S)-2-(2-oxo-3-(2-thienylmethyl) tetrahydro-1(2H)-pyrimidinyl)hexanoyl)amino) propanoic acid, (3S)-3-(1,3-benzodioxol-5-yl)-3-((2R,S)-2-(3-benzyl-5-methyl-2-oxo-1(2H)-pyridinyl)hexanoylamino)propanoic acid, (3S)-3-(1,3-benzodioxol-5-yl)-3-((2R,S)-2-(3-(3-chlorobenzyl)-5-methyl-2-oxo-1(2H)-pyridinyl) hexanoylamino)propanoic acid, (3S)-3-(1,3-benzodioxol-5-yl)-3-(((2S)-2-(2-oxo-3-(phenylmethyl)-1(2H)-pyridinyl) hexanoyl)amino) propanoic acid, (3S)-3-(1,3-benzodioxol-5-yl)-3-((2-(3-chlorophenyl)methyl)-5-methyl-2-oxo-1 (2H)-pyridinyl)hexanoyl)amino)propanoic acid, (3S)-3-{[(2S)-2-(3-benzyl-5-methyl-2-oxopyridin-1(2H)-yl) hexanoyl]amino}-3-(3,5-dimethoxyphenyl)propanoic acid, (3S)-3-{[(2S)-2-(3-benzyl-5-methyl-2-oxopyridin-1(2H)-yl)hexanoyl]amino}-3-(3-fluoro-4-methoxyphenyl) propanoic acid, (3S)-3-{[2-(3-benzyl-5-methyl-2-oxopyridin-1(2H)-yl)hexanoyl]amino}-3-(3-isopropoxyphenyl)propanoic acid, (3S)-3-({2-[3-(3-chlorobenzyl)-5-methyl-2-oxopyridin-1(2H)-yl] hexanoyl}amino)-3-(3-isopropoxyphenyl)propanoic acid, (3S)-3-(3-isopropoxyphenyl)-3-({2-[3-(2-methoxybenzyl)-5-methyl-2-oxopyridin-1(2H)-yl]hexanoyl}amino) propanoic acid, (3S)-3-{[2-(3-benzyl-5-methyl-2-oxopyridin-1(2H)-yl)hexanoyl]amino}-3-(3-ethoxy-4-methoxyphenyl)propanoic acid, (3S)-3-{[2-(3-benzyl-5-methyl-2-oxopyridin-1(2H)-yl)hexanoyl]amino}-3-(4-methoxy-3-methylphenyl)propanoic acid, (3S)-3-{[2-(3-benzyl-5-methyl-2-oxopyridin-1(2H)-yl)hexanoyl]amino}-3-phenylpropanoic acid, (3S)-3-({2-[3-(2-chlorobenzyl)-5-methyl-2-oxopyridin-1(2H)-yl]hexanoyl}amino)-3-(4-methylphenyl)propanoic acid, (3S)-3-({2-[3-(2-chlorobenzyl)-5-methyl-2-oxopyridin-1(2H)-yl] hexanoyl}amino)-3-(3-isopropoxyphenyl)propanoic acid, (3S)-3-({2-[3-(2-chlorobenzyl)-5-methyl-2-oxopyridin-1 (2H)-yl]hexanoyl}amino)-3-phenylpropanoic acid, (3S)-3-(1-methyl-1H-indol-6-yl)-3-({2-[5-methyl-2-oxo-3-(phenylmethyl)-1(2H)-pyridinyl]hexanoyl}amino) propanoic acid, (3S)-3-{3-[(1-methylethyl)oxy]phenyl}-3-({2-[5-methyl-3-(2-naphthalenylmethyl)-2-oxo-1(2H)-pyridinyl]hexanoyl}amino)propanoic acid, (3S)-3-({2-[5-methyl-2-oxo-3-(phenylmethyl)-1(2H)-pyridinyl] hexanoyl}amino)-3-[3-(2-methylpropyl)phenyl]propanoic acid, (3S)-3-[3-(difluoromethyl)phenyl]-3-({2-[5-methyl-2-oxo-3-(phenylmethyl)-1(2H)-pyridinyl]hexanoyl}amino) propanoic acid, (3S)-3-{3-[(1-methylethyl)oxy]phenyl}-3-({2-[5-methyl-3-[(2-methylphenyl)methyl]-2-oxo-1(2H)-pyridinyl]hexanoyl}amino)propanoic acid, (3S)-3-(3-fluorophenyl)-3-({2-[5-methyl-2-oxo-3-(phenylmethyl)-1 (2H)-pyridinyl]hexanoyl}amino)propanoic acid, (3S)-3-({2-[3-[(2-chloro-4-fluorophenyl)methyl]-5-methyl-2-oxo-1(2H)-pyridinyl]hexanoyl}amino)-3-{3-[(1-methylethyl) oxy]phenyl}propanoic acid and (3S)-3-{3-[(1-methylethyl) oxy]phenyl}-3-({2-[5-methyl-2-oxo-1-(phenylmethyl)-1,2-dihydro-3-pyridinyl]-2-phenylacetyl}amino) propanoic acid, and pharmaceutically acceptable salts thereof.

Other presently preferred compounds include (3S)-3-{ [(2S)-2-(3-benzyl-5-methyl-2-oxopyridin-1(2H)-yl) hexanoyl]amino}-3-(3',4'-dimethoxy-1,1'-biphenyl-4-yl) propanoic acid, (3S)-3-({(2S)-2-[3-(2-chlorobenzyl)-5-methyl-2-oxopyridin-1(2H)-yl]hexanoyl}amino)-3-(3',4'-dimethoxy-1,1'-biphenyl-4-yl)propanoic acid, (3S)-3-(1,1'-biphenyl-4-yl)-3-({(2S)-2-[3-(2-chloro-6-methylbenzyl)-5-methyl-2-oxopyridin-1(2H)-yl]hexanoyl}amino)propanoic acid, (3S)-3-{[(2S)-2-(3-benzyl-5-methyl-2-oxopyridin-1 (2H)-yl)hexanoyl]amino}-3-(1,1'-biphenyl-4-yl)propanoic acid, (3S)-3-(1,1'-biphenyl-4-yl)-3-({(2S)-2-[3-(2-chlorobenzyl)-5-methyl-2-oxopyridin-1(2H)-yl] hexanoyl}amino)propanoic acid, (3S)-3-{[(2S)-2-(3-benzyl-5-methyl-2-oxopyridin-1(2H)-yl)hexanoyl]amino}-3-(4'-methyl-1,1'-biphenyl-4-yl)propanoic acid, (3S)-3-({ (2S)-2-[3-(2-chlorobenzyl)-5-methyl-2-oxopyridin-1(2H)-yl]hexanoyl}amino)-3-(4'-methyl-1,1'-biphenyl-4-yl) propanoic acid, (3S)-3-({(2S)-2-[3-(2-chloro-6-methylbenzyl)-5-methyl-2-oxopyridin-1(2H)-yl] hexanoyl}amino)-3-(4'-methyl-1,1'-biphenyl-4-yl) propanoic acid, (3S)-3-{[(2S)-2-(3-benzyl-5-methyl-2-oxopyridin-1(2H)-yl)hexanoyl]amino}-3-(2',6'-dimethoxy-1,1'-biphenyl-4-yl)propanoic acid, (3S)-3-({(2S)-2-[3-(2-chlorobenzyl)-5-methyl-2-oxopyridin-1(2H)-yl] hexanoyl}amino)-3-(2',6'-dimethoxy-1,1'-biphenyl-4-yl) propanoic acid, (3S)-3-({(2S)-2-[3-(2-chloro-6-methylbenzyl)-5-methyl-2-oxopyridin-1(2H)-yl] hexanoyl}amino)-3-(2',6'-dimethoxy-1,1'-biphenyl-4-yl) propanoic acid, (3S)-3-{[(2S)-2-(3-benzyl-5-methyl-2-oxopyridin-1(2H)-yl)hexanoyl]amino}-3-biphenyl-3-yl) propanoic acid, (3S)-3-(1,1'-biphenyl-3-yl)-3-({(2S)-2-[3-(2-chlorobenzyl)-5-methyl-2-oxopyridin-1(2H)-yl] hexanoyl}amino)propanoic acid, (3S)-3-(1,1'-biphenyl-3-yl)-3-({(2S)-2-[3-(2-chloro-6-methylbenzyl)-5-methyl-2-oxopyridin-1(2H)-yl]hexanoyl}amino)propanoic acid, (3S)-3-{[(2S)-2-(3-benzyl-5-methyl-2-oxopyridin-1(2H)-yl) hexanoyl]amino}-3-(2'-methoxy-1,1'-biphenyl-3-yl) propanoic acid, (3S)-3-({(2S)-2-[3-(2-chlorobenzyl)-5-methyl-2-oxopyridin-1(2H)-yl]hexanoyl}amino)-3-(2'-methoxy-1,1'-biphenyl-3-yl)propanoic acid, (3S)-3-({(2S)-2-[3-(2-chloro-6-methylbenzyl)-5-methyl-2-oxopyridin-1 (2H)-yl]hexanoyl}amino)-3-(2'-methoxy-1,1'-biphenyl-3-yl)propanoic acid, (3S)-3-({(2S)-2-[3-(2-fluoro-6-methoxybenzyl)-5-methyl-2-oxopyridin-1(2H)-yl] hexanoyl}amino)-3-(4-methylphenyl)propanoic acid, (3S)-3-({(2S)-2-[3-(2,6-dimethylbenzyl)-5-methyl-2-oxopyridin- 1(2H)-yl]hexanoyl}amino)-3-(4-methylphenyl)propanoic acid, (3S)-3-({(2S)-2-[3-(3,5-dimethylbenzyl)-5-methyl-2-oxopyridin-1(2H)-yl]hexanoyl}amino)-3-(4-methylphenyl) propanoic acid, (3S)-3-({(2S)-2-[3-(2,6-dichlorobenzyl)-5-methyl-2-oxopyridin-1(2H)-yl]hexanoyl}amino)-3-(4-methylphenyl)propanoic acid, (3S)-3-({(2S)-2-[3-(2-chloro-6-fluorobenzyl)-5-methyl-2-oxopyridin-1(2H)-yl]hexanoyl}amino)-3-(4-methylphenyl)propanoic acid, (3S)-3-({(2S)-2-[3-(2,6-difluorobenzyl)-5-methyl-2-oxopyridin-1(2H)-yl]hexanoyl}amino)-3-(4-methylphenyl)propanoic acid, (3S)-3-(1,3-benzodioxol-5-yl)-3-({(2S)-2-[3-(2,6-difluorobenzyl)-5-methyl-2-oxopyridin-1(2H)-yl]hexanoyl}amino)propanoic acid, (3S)-3-(1,3-benzodioxol-5-yl)-3-({(2S)-2-[3-(2-chloro-6-fluorobenzyl)-5-methyl-2-oxopyridin-1(2H)-yl]hexanoyl}amino)propanoic acid, (3S)-3-(1,3-benzodioxol-5-yl)-3-({(2S)-2-[3-(2,6-dichlorobenzyl)-5-methyl-2-oxopyridin-1(2H)-yl]hexanoyl}amino)propanoic acid, (3S)-3-(1,3-benzodioxol-5-yl)-3-({(2S)-2-[3-(2,6-dimethylbenzyl)-5-methyl-2-oxopyridin-1(2H)-yl]hexanoyl}amino)propanoic acid, (3S)-3-(1,3-benzodioxol-5-yl)-3-({(2S)-2-[3-(3,5-dimethylbenzyl)-5-methyl-2-oxopyridin-1(2H)-yl]hexanoyl}amino)propanoic acid, (3S)-3-(1,3-benzodioxol-5-yl)-3-({(2S)-2-[3-(2-fluoro-6-methoxybenzyl)-5-methyl-2-oxopyridin-1(2H)-yl]hexanoyl}amino)propanoic acid, (3S)-3-({(2S)-2-[3-(2-chlorobenzyl)-5-methyl-2-oxopyridin-1(2H)-yl]hexanoyl}amino)-3-(3,4-diethoxyphenyl)propanoic acid, (3S)-3-(3,4-diethoxyphenyl)-3-({(2S)-2-[3-(2,6-difluorobenzyl)-5-methyl-2-oxopyridin-1(2H)-yl]hexanoyl}amino)propanoic acid, (3S)-3-({(2S)-2-[3-(2,6-difluorobenzyl)-5-methyl-2-oxopyridin-1(2H)-yl]hexanoyl}amino)-3-(3-ethoxyphenyl)propanoic acid, (3S)-3-({(2S)-2-[3-(2-chloro-6-fluorobenzyl)-5-methyl-2-oxopyridin-1(2H)-yl]hexanoyl}amino)-3-(3-ethoxyphenyl)propanoic acid, (3S)-3-({(2S)-2-[3-(2-chlorobenzyl)-5-methyl-2-oxopyridin-1(2H)-yl]-3-methylbutanoyl}amino)-3-(4-methylphenyl)propanoic acid, (3S)-3-({(2S)-2-[3-(2-chlorobenzyl)-5-methyl-2-oxopyridin-1(2H)-yl]-4-methylpentanoyl}amino)-3-(4-methylphenyl)propanoic acid, (3S)-3-(1,3-benzodioxol-5-yl)-3-({(2S)-2-[3-(2-chlorobenzyl)-5-methyl-2-oxopyridin-1(2H)-yl]-4-methylpentanoyl}amino)propanoic acid, (3S)-3-(1,3-benzodioxol-5-yl)-3-({(2S)-2-[3-(2-chlorobenzyl)-5-methyl-2-oxopyridin-1(2H)-yl]-3-methylbutanoyl}amino)propanoic acid, (3S)-3-(1,3-benzodioxol-5-yl)-3-({(2S)-2-[3-(2-chlorobenzyl)-5-methyl-2-oxopyridin-1(2H)-yl]-3-phenylpropanoyl}amino) propanoic acid, (3S)-3-({(2S)-2-[3-(2-chlorobenzyl)-5-methyl-2-oxopyridin-1(2H)-yl]-3-phenylpropanoyl}amino)-3-(4-methylphenyl)propanoic acid, (3S)-3-(1,3-benzodioxol-5-yl)-3-(((2R)-2-(1-benzyl-5-methyl-2-oxo-1,2-dihydropyridin-3-yl)hexanoyl)amino) propanoic acid and pharmaceutically acceptable salts thereof.

A presently most preferred compound is (3S)-3-(1,3-benzodioxol-5-yl)-3-((2S)-2-(3-benzyl-5-methyl-2-oxo-1(2H)-pyridinyl)hexanoylamino)propanoic acid or a pharmaceutically acceptable salt thereof.

Derivatives of Formulae I–V which are esters, carbamates, aminals, amides, optical isomers and pro-drugs are also contemplated.

The present invention also relates to pharmaceutical compositions comprising a physiologically acceptable diluent and at least one compound of the present invention.

The present invention further relates to a process of inhibiting the binding of $\alpha_4\beta_1$ integrin to VCAM-1 comprising exposure of a cell expressing $\alpha_4\beta_1$ integrin to a cell expressing VCAM-1 in the presence of an effective inhibiting amount of a compound of the present invention. The VCAM-1 may be on the surface of a vascular endothelial cell, an antigen presenting cell, or other cell type. The $\alpha_4\beta_1$ may be on a white blood cell such as a monocyte, lymphocyte, granulocyte; a stem cell; or any other cell that naturally expresses $\alpha_4\beta_1$.

The invention also provides a method for treating disease states mediated by $\alpha_4\beta_1$ binding which comprises administration of an effective amount of a compound of the present invention, either alone or in formulation, to an afflicted patient.

DETAILED DESCRIPTION OF THE INVENTION

Definition of Terms

The term "alkyl" as used herein, alone or in combination, refers to $C_1$–$C_{12}$ straight or branched, substituted or unsubstituted saturated chain radicals derived from saturated hydrocarbons by the removal of one hydrogen atom, unless the term alkyl is preceded by a $C_x$–$C_y$ designation. Representative examples of alkyl groups include methyl, ethyl, n-propyl, iso-propyl, n-butyl, sec-butyl, iso-butyl, and tert-butyl among others.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a $C_1$–$C_6$ unit for a particular functionality. For example lower alkyl means $C_1$–$C_6$ alkyl.

The term "aliphatic acyl" as used herein, alone or in combination, refers to radicals of formula alkyl-C(O)—, alkenyl-C(O)— and alkynyl-C(O)— derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl and methylpropiolyl, among others.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

"Cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexylmethyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkoxyalkyl" as used herein, refers to $R_y$—O—$R_z$, wherein $R_y$ is lower alkyl as defined above, and $R_z$ is alkylene (—$(CH_2)_w$—) wherein w is an integer of from one to six.

The term "alkenoxy" as used herein, alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy" as used herein, alone or in combination, refers to a radical of formula alkynyl-O—, provided that the radical is not an -ynol ether. Examples of suitable alkynoxy radicals include, but are not limited to, propargyloxy, 2-butynyloxy and the like.

The term "thioalkoxy" refers to a thioether radical of formula alkyl-S—, wherein "alkyl" is as defined above.

The term "sulfonamido" as used herein refers to —$SO_2NH_2$.

The term "carboxaldehyde" as used herein refers to —C(O)R wherein R is hydrogen.

The terms "carboxamide" or "amide" as used herein refer to —C(O)$NR_aR_b$ wherein $R_a$ and $R_b$ are each independently hydrogen, alkyl or any other suitable substituent.

The term "carboxy" as used herein refers to —C(O)O—.

The term "alkoxyalkoxy" as used herein refers to $R_c$O—$R_d$O— wherein $R_c$ is lower alkyl as defined above and $R_d$ is alkylene wherein alkylene is —$(CH_2)_{n'}$,— wherein n' is an integer from 1 to 6. Representative examples of alkoxyalkoxy groups include methoxymethoxy, ethoxymethoxy, t-butoxymethoxy among others.

The term "alkylamino" as used herein refers to $R_e$NH— wherein $R_e$ is a lower alkyl group, for example, ethylamino, butylamino, among others.

The term "alkenylamino" as used herein, alone or in combination, refers to a radical of formula alkenyl-NH— or (alkenyl)$_2$N—, wherein the term "alkenyl" is as defined above, provided that the radical is not an enamine. An example of such alkenylamino radical is the allylamino radical.

The term "alkynylamino" as used herein, alone or in combination, refers to a radical of formula alkynyl-NH— or (alkynyl)$_2$N— wherein the term "alkynyl" is as defined above, provided that the radical is not an amine. An example of such alkynylamino radicals is the propargyl amino radical.

The term "dialkylamino" as used herein refers to $R_fR_gN$— wherein $R_f$ and $R_g$ are independently selected from lower alkyl, for example diethylamino, and methyl propylamino, among others.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination, refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group which is an aromatic ring containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Aralkyl" and "alkylaryl" employ the term "alkyl" as defined above. Rings may be multiply substituted.

The term "aralkyl" as used herein, alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmetbyl, thienylpropyl and the like.

The term "aralkenyl" as used herein, alone or in combination, refers to an aryl substituted alkenyl radical, wherein the terms "aryl" and "alkenyl" are as defined above.

The term "arylamino" as used herein, alone or in combination, refers to a radical of formula aryl-NH—, wherein "aryl" is as defined above. Examples of arylamino radicals include, but are not limited to, phenylamino (anilido), naphthlamino, 2-, 3-, and 4-pyridylamino and the like.

The term "benzyl" as used herein, alone or in combination, refers to $C_6H_5$—$CH_2$—.

The term "biaryl" as used herein, alone or in combination, refers to a radical of formula aryl-aryl, wherein the term "aryl" is as defined above.

The term "thioaryl" as used herein, alone or in combination, refers to a radical of formula aryl-S—, wherein the term "aryl" is as defined above. An example of a thioaryl radical is the thiophenyl radical.

The term "aroyl" as used herein, alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl" as used herein, alone or in combination, refers to a non-aromatic 3- to 10- membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group, including but not limited to 2-methyl-5-thiazolyl, 2-methyl-1-pyrrolyl and 5-ethyl-2-thiophenyl.

The term "heterocyclylalkyl" as used herein refers to a heterocyclyl group as previously defined appended to the parent molecular moiety through an alkyl group, including but not limited to 2-thienylmethyl, 2-pyridinylmethyl and 2-(1-piperidinyl) ethyl.

The term "aminal" as used herein refers to a hemi-acetal of the structure $R_hC(NR_iR_j)(NR_kR_l)$— wherein $R_h$, $R_i$, $R_j$, $R_k$ and $R_l$ are each independently hydrogen, alkyl or any other suitable substituent.

The term "ester" as used herein refers to —$C(O)R_m$, wherein $R_m$ is hydrogen, alkyl or any other suitable substituent.

The term "carbamate" as used herein refers to compounds based on carbamic acid $NH_2C(O)OH$.

The term "optical isomers" as used herein refers to compounds which differ only in the stereochemistry of at least one atom, including enantiomers, diastereomers and racemates.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)O—. Rings may be substituted multiple times.

The terms "electron-witbdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16–18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, sulfonyl and aryl lower alkanoyl among others. Electron sulfonyl donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio, alkyldithio, carboxy lower alkyl, arylalkoxy, alkanoylamino, alkanoyl (lower alkyl)amino, lower alkylsufonylamino, arylsulfonylamino, alkylsulfonyl(lower alkyl)amino, arylsulfonyl(lower alkyl)amino, lower alkylcarboxamide, di(lower alkyl)carboxamide, sulfonamide, lower alkylsulfonamide, di(lower alkyl)sulfonamide, lower alkylsulfonyl, and arylsulfonyl.

As used herein, the term "composition" is intended to encompass a product comprising the specified ingredients in the specified amounts, as well as any product which results, directly or indirectly, from a combination of the specified ingredients in the specified amounts.

The ring including Y in Formula II or ring Q in Formulae I and V can be a mono-cyclic heterocycle or aromatic ring, or can be a bicyclic ring. When more than one Y is $C(R^2)(R^3)$, the C substituents from each Y may be joined to form a ring. Moreover, in the rings including Y, two independent $R^2$, $R^3$, $R^5$ and $R^7$ groups taken together may be linked to form a ring.

Suitable substituents for the aryl, alkyl, cycloalkyl, heterocyclyl groups or ring including Y defined above, when present, include alcohols, amines, heteroatoms, or any combination of aryl, alkyl, cycloalkyl or heterocyclyl groups either attached directly, or via suitable linkers. The linkers are typically short chains of 1–3 atoms containing any combination of C, C=O, $CO_2$, O, N, S, S=O, $SO_2$, as for example ethers, amides, amines, ureas, sulfamides, sulfonamides, and the like.

In the Formulae I and III–V, defined R groups $R^1$ and $R^{17}$ potentially substitute their associated rings a number of times. For $R^1$, when q is zero, the associated ring is unsubstituted, having hydrogens at each available position. Similarly, for $R^{17}$, when s is zero, the associated ring is unsubstituted, having hydrogens at each available position.

For example, $R^1$, $R^2$, $R^3$, $R^5$, $R^7$, $R^{11}$ and $R^{13}$ in Formulae I–V above may independently be, but are not limited to, phenyl, thienylmethyl, isobutyl, n-butyl, 2-thienylmethyl, 1,3-thiazol-2-yl-methyl, benzyl, thienyl, 3-pyridinylmethyl, 3-methyl-1-benzothiophen-2-yl, allyl, 3-methoxybenzyl, propyl, 2-ethoxyethyl, cyclopropylmethyl, benzylsulfanylmethyl, benzylsulfonylmethyl, phenylsulfanylmethyl, phenethylsulfanylmethyl, 3-phenylpropylsulfanylmethyl, 4-((2-toluidinocarbonyl) amino)benzyl, 2-pyridinylethyl, 2-(1H-indol-3-yl)ethyl, 1H-benzimidazol-2-yl, 4-piperidinylmethyl, 3-hydroxy-4-methoxybenzyl, 4-hydroxyphenethyl, 4-aminobenzyl, phenylsulfonylmethyl, 4-(acetylamino)phenyl, 4-methoxyphenyl, 4-aminophenyl, 4-chlorophenyl, (4-(benzylsulfonyl)amino)phenyl, (4-(methylsulfonyl)amino) phenyl, 2-aminophenyl, 2-methylphenyl, isopropyl, 2-oxo-1-pyrrolidinyl, 3-(methylsulfanyl)propyl, (propylsulfanyl) methyl, octylsulfanylmethyl, 3-aminophenyl, 4-((2-toluidinocarbonyl)amino)phenyl, 2-((methylbenzyl)arnino) benzyl, methylsulfanylethyl, ethylsulfanylmethyl, 2-chlorobenzyl, 2-bromobenzyl, 2-fluorobenzyl, 2-chloro-6-fluorobenzyl, 2-chloro-4-fluorobenzyl, 2,4-dichlorobenzyl, 2-chloro-6-methoxybenzyl, 2-cyanobenzyl, 2,6-difluorobenzyl, 2-chloro-5-(trifluoromethyl)benzyl, 2-chloro-6-methylbenzyl, 2,6-dimethoxybenzyl, 2-chloro-5-(methylsulfonyl)benzyl, 2-chloro-6-cyanobenzyl, 2-chloro-6-ethoxybenzyl, 2-chloro-5-methoxybenzyl, 2-chloro-5-fluorobenzyl, 5-chloro-2-fluorobenzyl, ethyl, propyl, butyl, pentyl, cyclopropyl, tert-butylamino, propylamino, 4-methyl-1-piperazinyl, 1-azetidinyl, 4-morpholino, (4-carboxyphenyl)amino, pivaloylamino, ((tert-butylamino)

carbonyl)amino, trifluoromethyl, benzyloxy, 2-(2-metboxyethoxy)ethoxy, 2-(2-(2-methoxyethoxy)ethoxy) ethoxy and 2-(2-(2-(2-methoxyethoxy)ethoxy)ethoxy) ethoxy. $R^6$ and $R^8$ may be linked to form a ring such as cyclopropyl, cyclobutyl, cyclopentyl, cyclohexyl, 4-piperidinyl, and 4-tetrahydropyranyl among others. $R^4$ and $R^{13}$ may be linked to form a ring such as pyrrolidino, 1-piperidino, 4-methyl-1-piperazino, 4-aceto-1-piperazino, and 4-morpholino among others. $R^9$ and $R^{10}$ may be linked to form a ring such as cyclopropyl, cyclobutyl, cyclopentyl, and cyclohexyl among others.

The $R^4$ substituent for Formulae I–III and the $R^{21}$ substituent of Formula IV above may be, but are not limited to, 1,3-benzodioxol-5-yl, 1-naphthyl, thienyl, 4-isobutoxyphenyl, 2,6-dimethylphenyl, allyloxyphenyl, 3-bromo-4-methoxyphenyl, 4-butoxyphenyl, 1-benzofuran-2-yl, 2-thienylmethyl, phenyl,methysulfanyl, phenylsulfanyl, phenethylsulfanyl, 4-bromo-2-thienyl, 3-methyl-2-thienyl, 4,5-dihydro-1,3-oxazol-2-yl, 3-(trifluoromethyl)phenyl, 4-(trifluoromethoxy)phenyl, 2,3-dihydro-1,4-benzodioxin-6-yl, 7-methoxy-1,3-benzodioxol-5-yl, 3-ethoxy-4-methoxyphenyl, 3,4-dimethoxyphenyl, 3,4-diethoxyphenyl, 3-ethoxyphenyl, 3-methoxy-4-methylphenyl, 3,5-dimethoxy-4-methylphenyl, 3-propoxyphenyl, 3-butoxyphenyl, 3-(2-methoxyethoxy) phenyl, 3,4-dipropoxyphenyl, 3-(difluoromethoxy)phenyl, 2-naphthyl, 3-isopropoxyphenyl, 1-methyl-1H-indol-5-yl, 2,3-dihydro-1-benzofuran-5-yl, 1,3-diethyl-2-oxo-2,3-dihydro-1H-benzimidazol-5-yl, 3-(trifluoromethoxy) phenyl, 1-methyl-1H-indol-6-yl, 3-(cyclopropoxy)phenyl, 3-(cyclopropylmethoxy)phenyl, 3-(difluoromethoxy) phenyl, 3-(1,1,2,2-tetrafluoroethoxy)phenyl, 1-ethyl-1H-indol-5-yl, 3-(diethylamino)phenyl, 6-methoxy-2-naphthyl, 3-[(methylsulfonyl)amino]phenyl, 3-[methyl (methylsulfonyl)amino]phenyl, 3-[ethyl(methylsulfonyl) amino]phenyl, 1H-indol-5-yl, 3-fluoro-4-methoxyphenyl, and 3-(difluoromethyl)phenyl.

The $R^6$ and $R^8$ substituents for Formulae I–V above may be, but are not limited to hydrogen, butyl, benzyl, benzyloxymethyl, ethyl, propyl, phenylsulfanylmethyl, benzylsulfanylmethyl, methylsulfanylethyl, ethylsulfanylmethyl, methyl, or carboxyethyl.

$R^4$ and $R^{13}$ may be linked to form a ring such as 1-pyrrolidino, 1-piperidino, 4-methyl-1-piperazino, 4-acetyl-1-piperazino and 4-morpholino among others.

$R^6$ and $R^8$ may be linked to form a ring such as cyclopropyl, cyclobutyl, cyclopentyl and cyclohexyl, among others.

$R^9$ and $R^{10}$ may be linked to form a ring such as cyclopropyl, cyclobutyl, cyclopentyl and cyclohexyl, among others.

Abbreviations

Abbreviations which have been used in the schemes and the examples which follow are: BOC for t-butyloxycarbonyl; EtOAc for ethyl acetate; DMF for dimethylformamide; THF for tetrahydrofuran; Tos for p-toluenesulfonyl; DCC for dicyclohexylcarbodiimide; HOBT for 1-hydroxybenzotriazole; TFAA for trifluoroacetic anhydride; NMM for N-methyl morpholine; DIPEA for diisopropylethylamine; DCM for methylene dichloride; LHMDS for lithium hexamethyl disilazide; NaHMDS for sodium hexamethyl disilazide; CDI for 1,1'-carbonlyldiimidazole HBTU for O-benzotriazol-1-yl-N,N,N',N'-tetramethyluronium hexafluorophosphate, EDCI for 1-[3-(dimethylamino) propyl]-3-ethylcarbodiimide hydrochloride and TBS for TRIS-buffered saline. Amino acids are abbreviated as follows: C for L-cysteine; D for L-aspartic acid; E for L-glutamic acid; G for glycine; H for L-histidine; I for L-isoleucine; L for L-leucine; N for L-asparagine; P for L-proline; Q for L-glutamine; S for L-serine; T for L-threonine; V for L-valine, and W for L-tryptophan.

Examples of the procedures utilized to synthesize the compounds are illustrated by the following schemes.

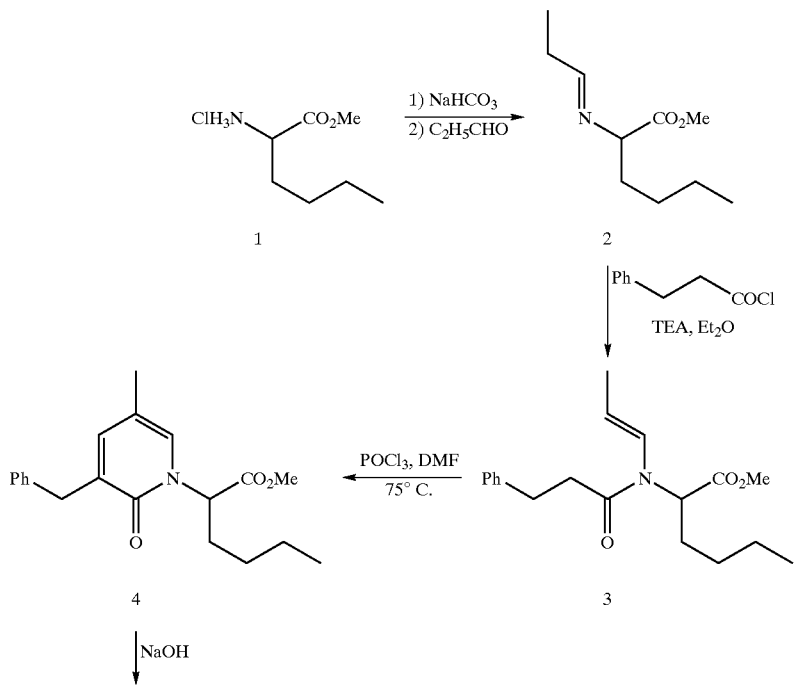

Scheme 1

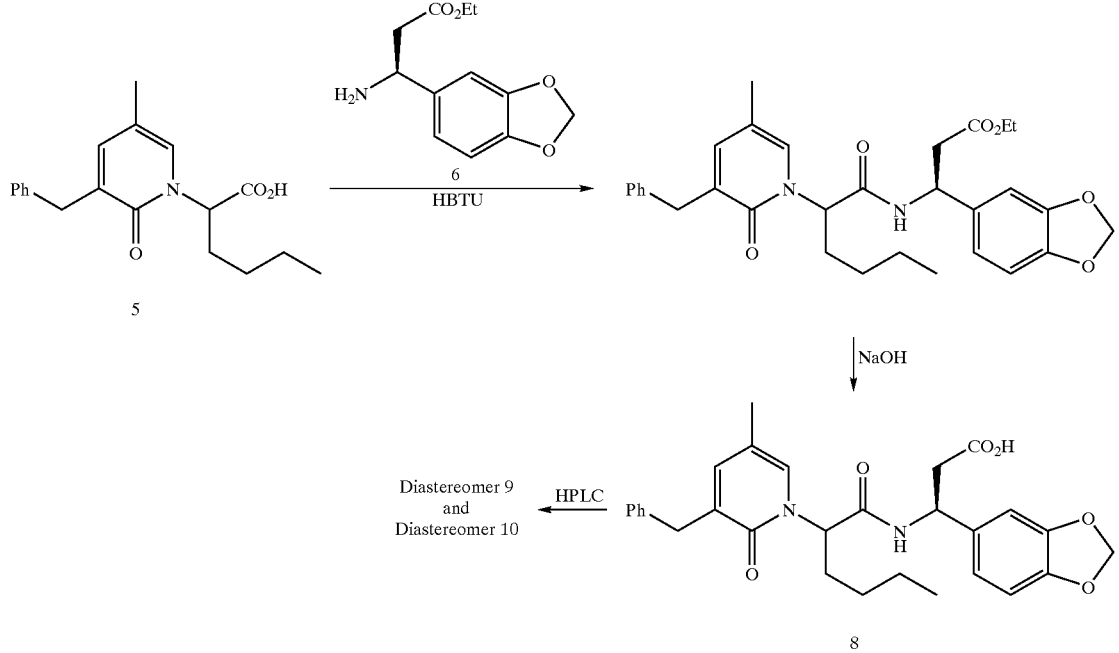
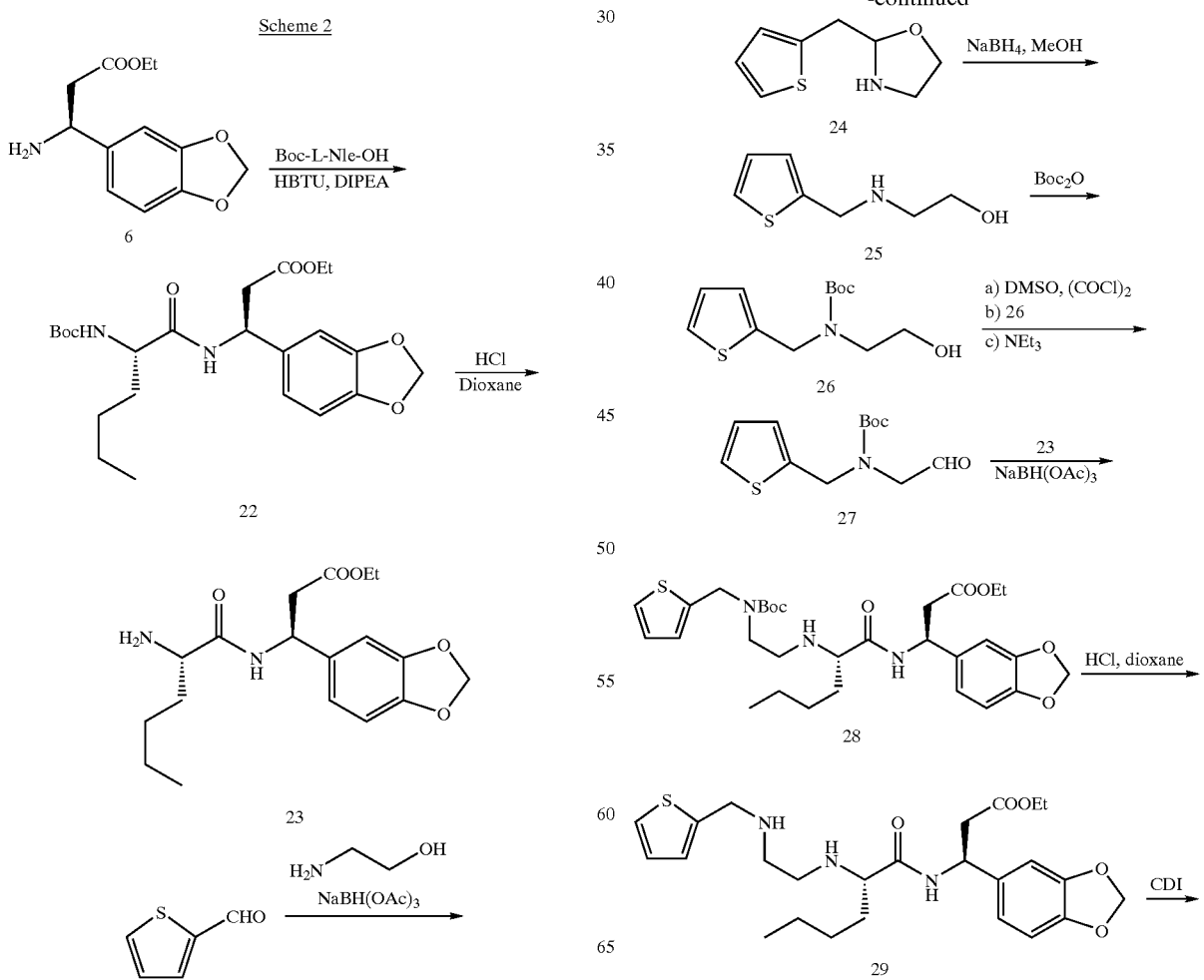

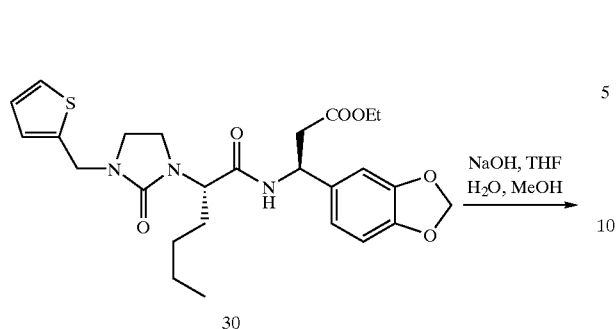
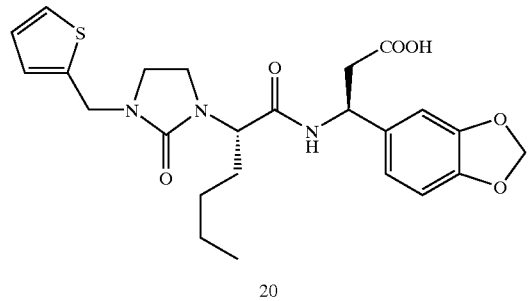
Scheme 3, shown below, illustrates the procedure described in Example 11.
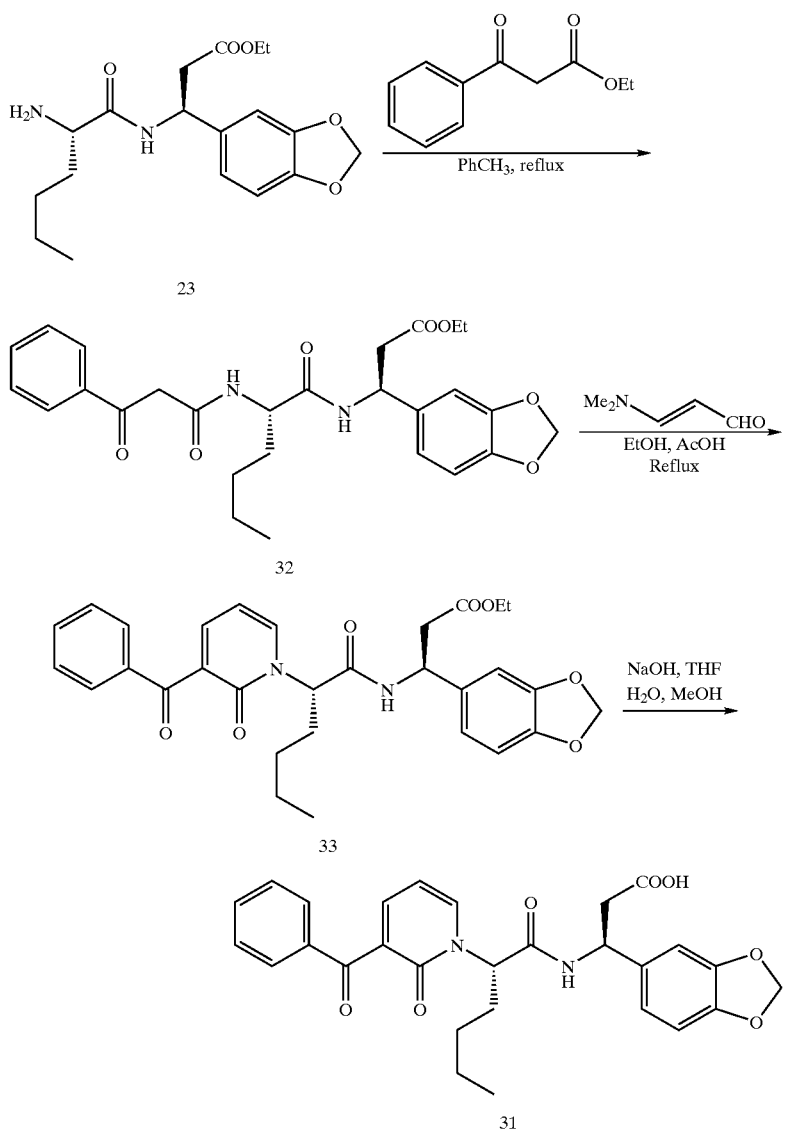

Scheme 4, shown below, illustrates Example 12.
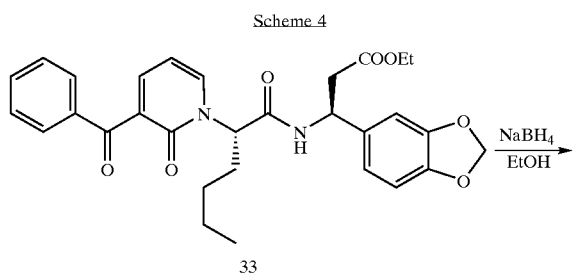
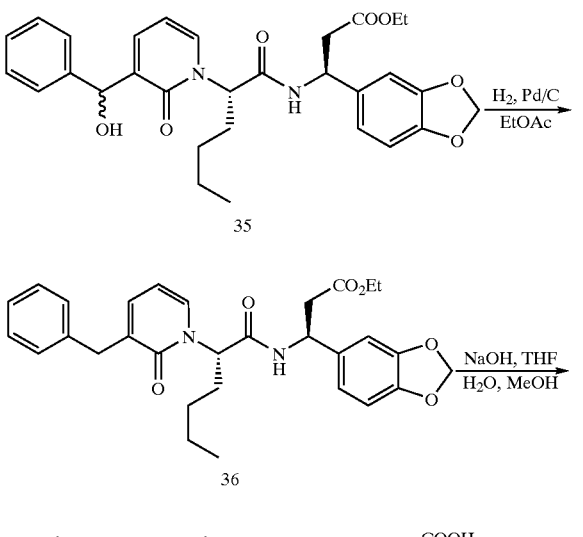
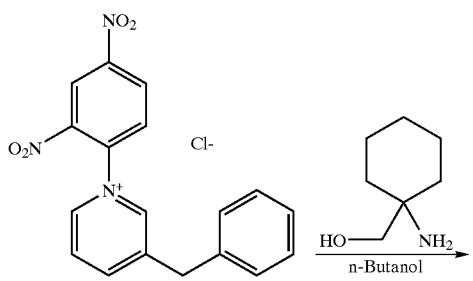
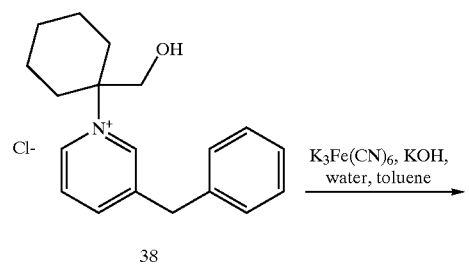
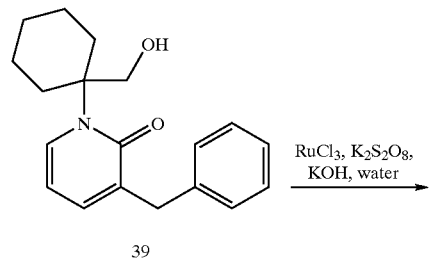
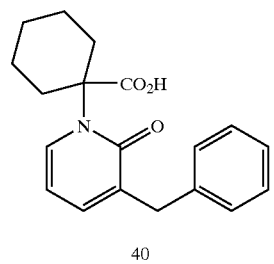
Scheme 5, shown below, illustrates the procedure of Example 13.
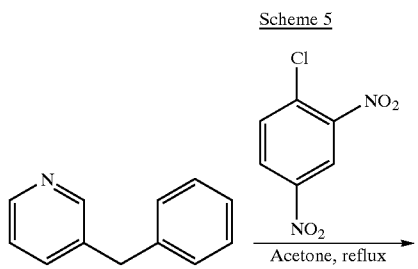
Scheme 6, shown below, illustrates the procedure described in Example 14.

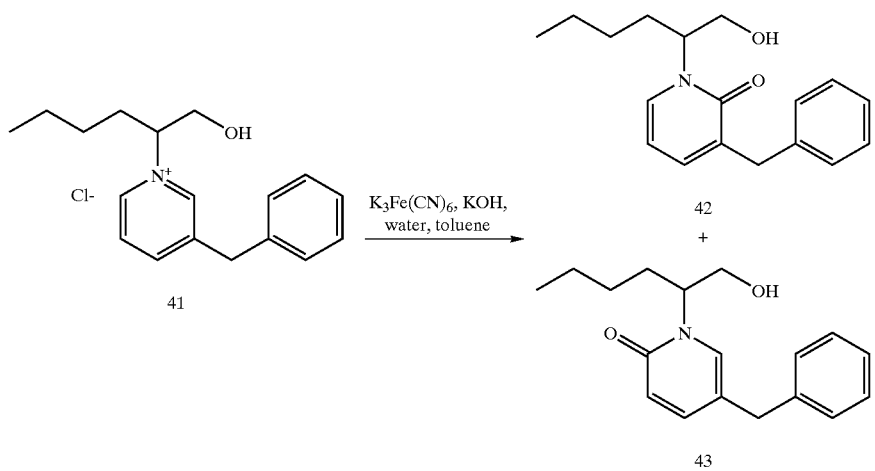
Scheme 7, shown below, illustrates the procedure described in Example 15.
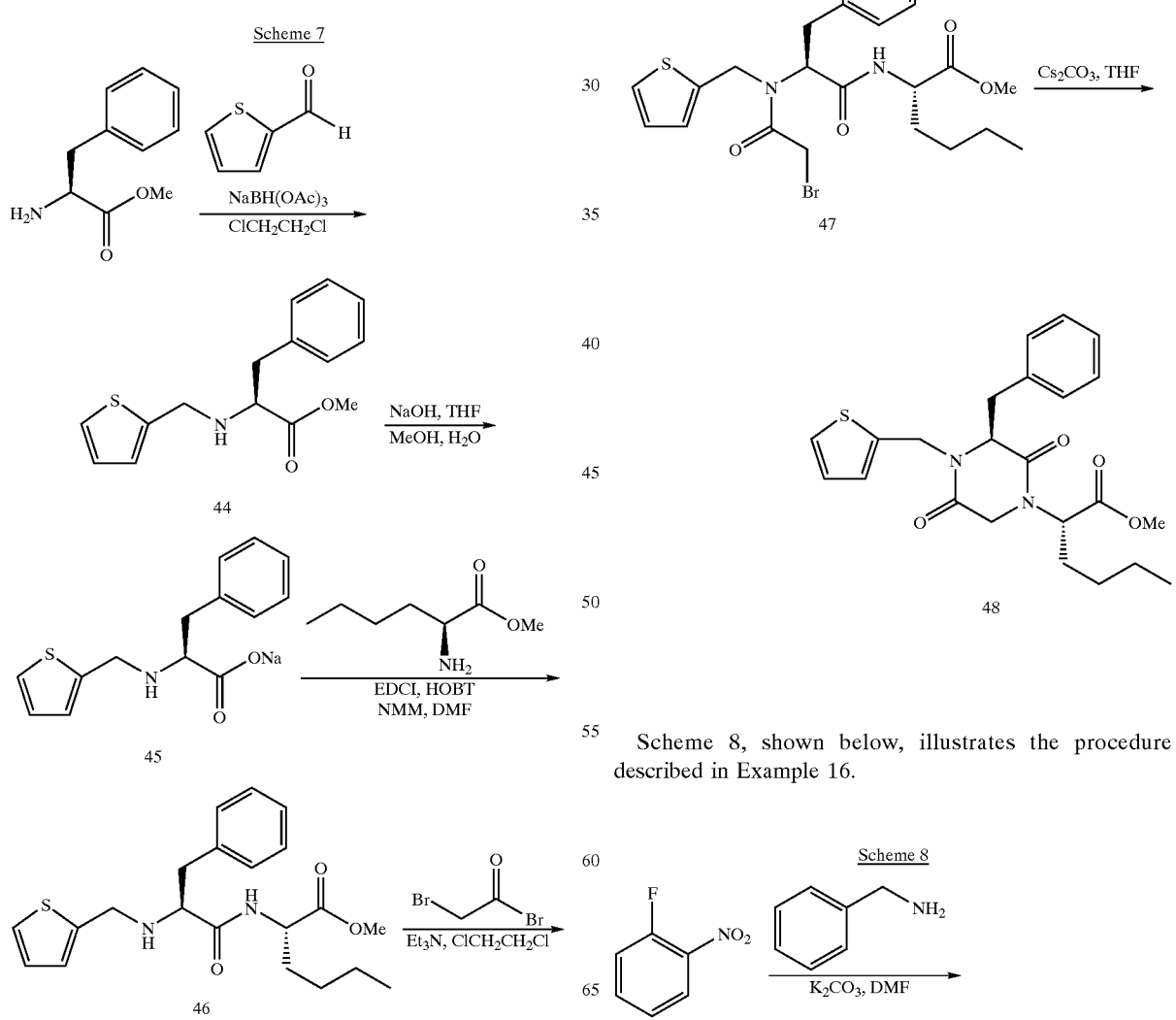
Scheme 8, shown below, illustrates the procedure described in Example 16.

-continued
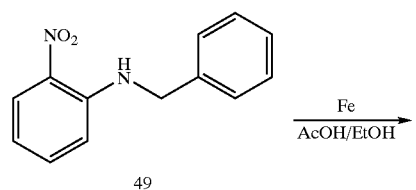
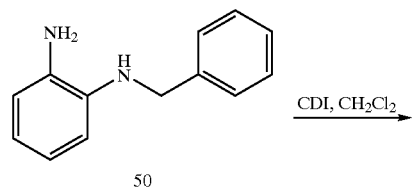
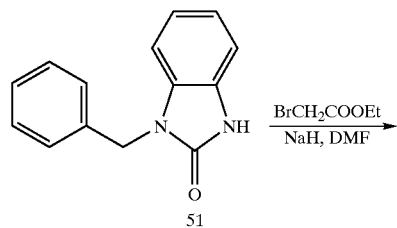
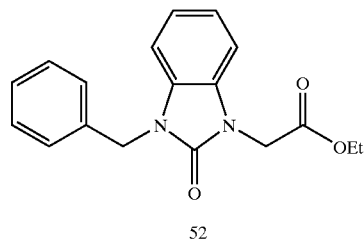
Scheme 9, shown below, illustrates the procedure described in Example 17.
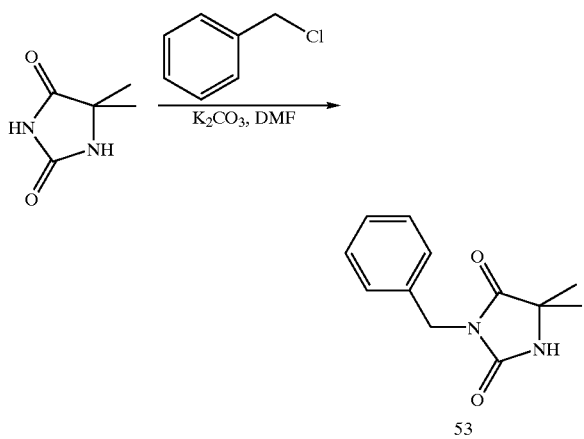
Scheme 10, shown below, illustrates the procedure described in Example 18.
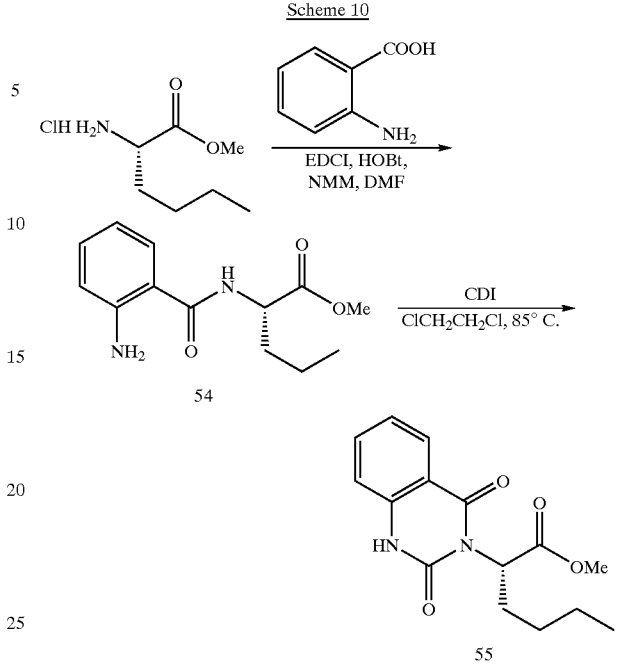
Scheme 11, shown below, illustrates the procedure described in Example 19.
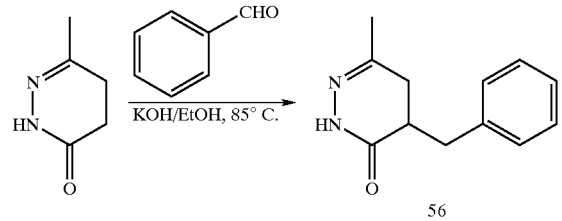
Scheme 12, shown below, illustrates the procedure described in Example 20.
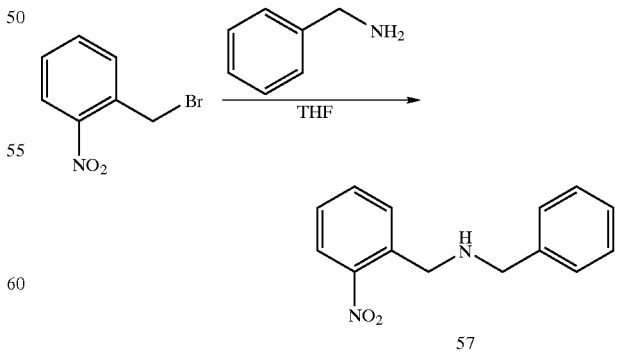
Scheme 13, shown below, illustrates the procedure described in Example 21.

Scheme 13
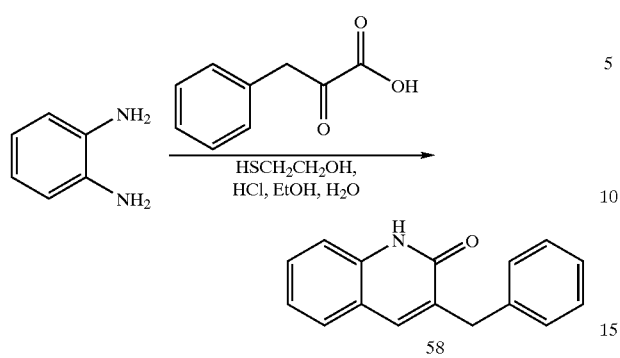
Scheme 14, shown below, illustrates the procedure of Example 22.
Scheme 14
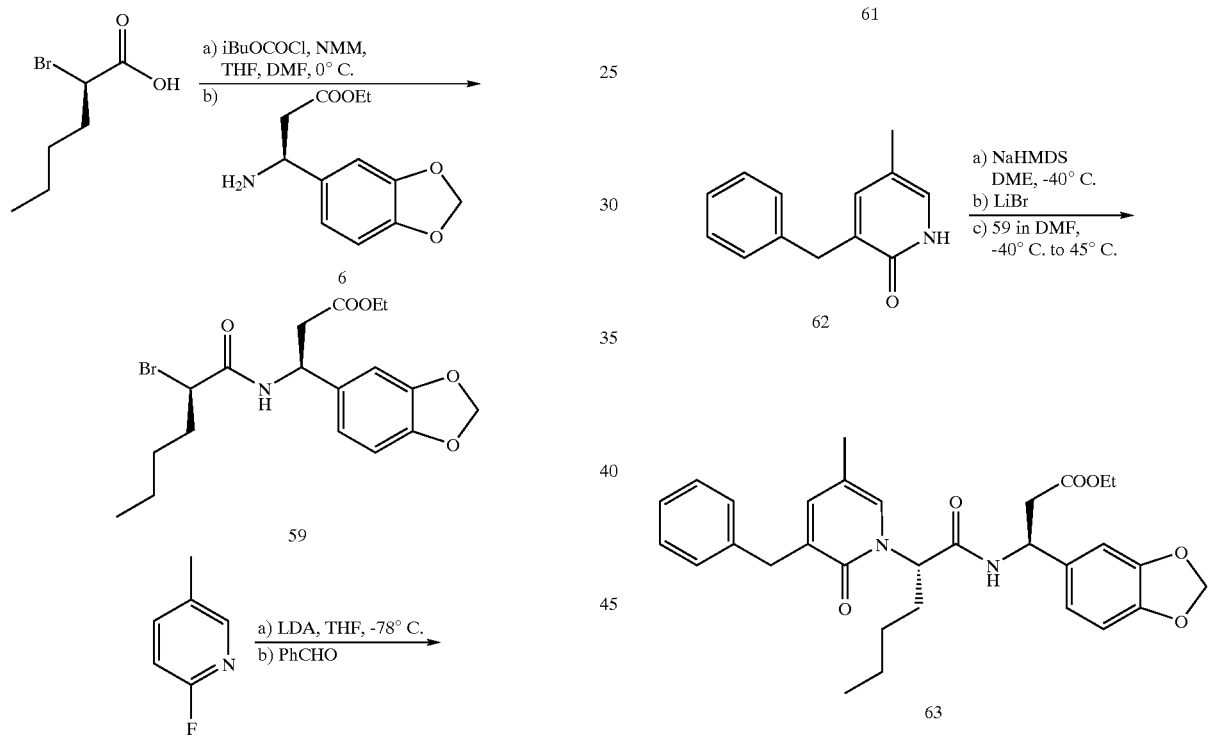
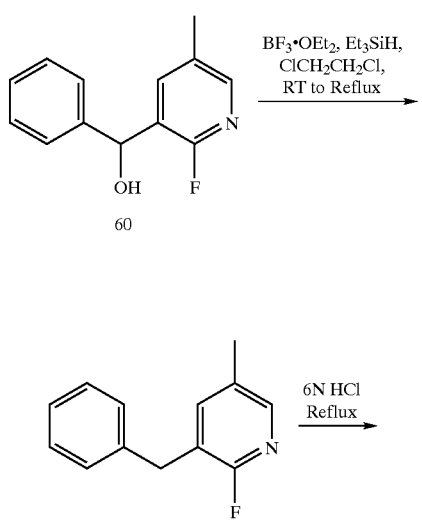
Scheme 15
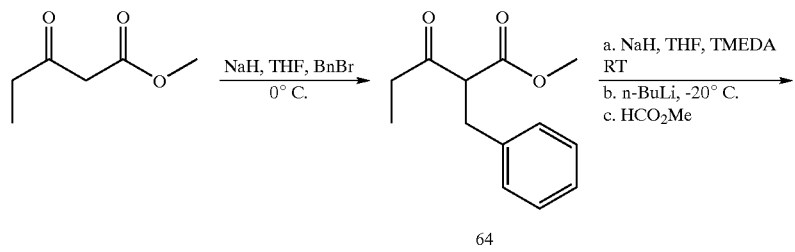

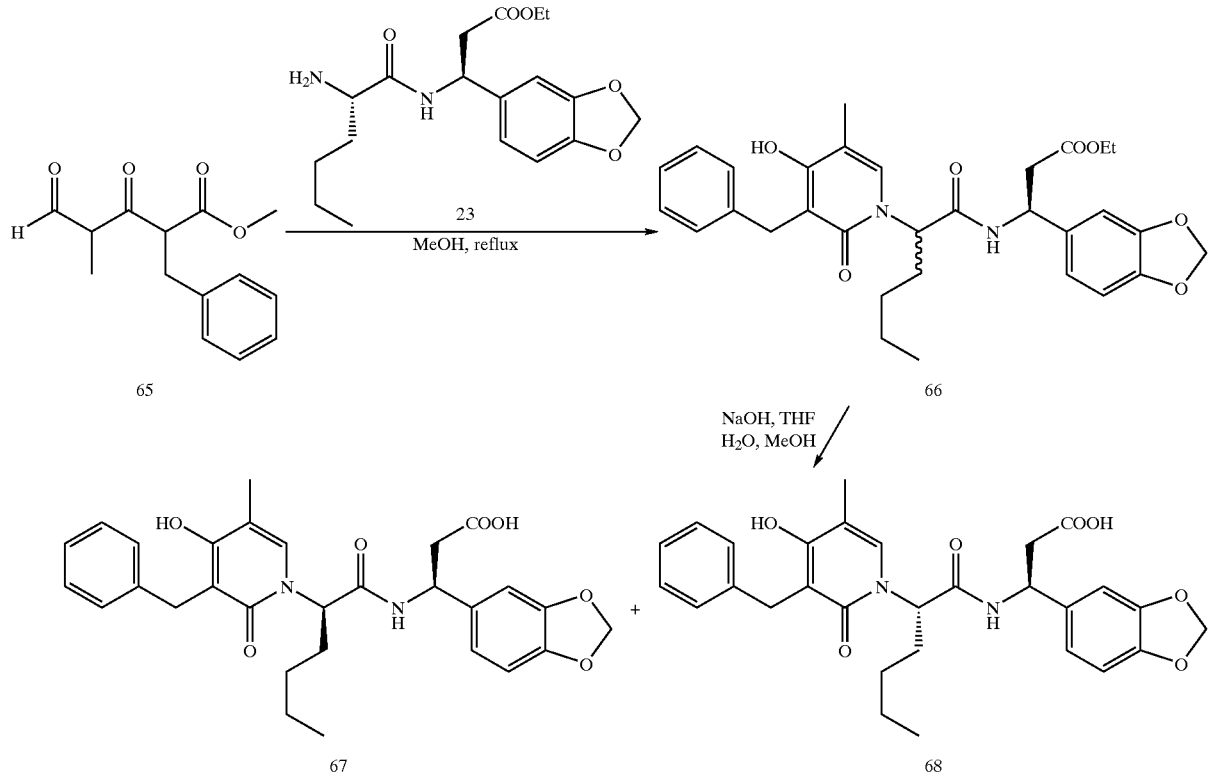
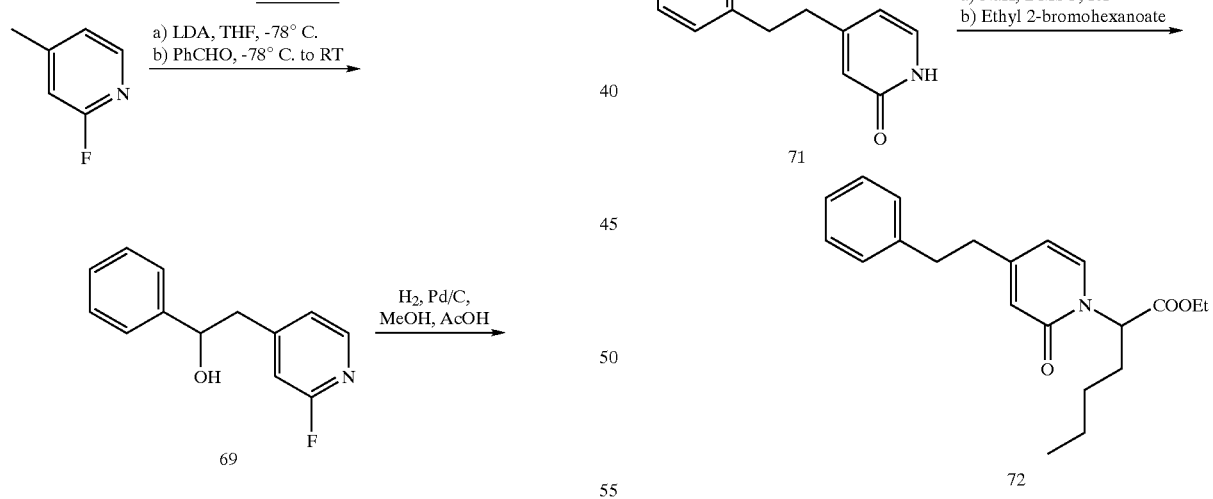
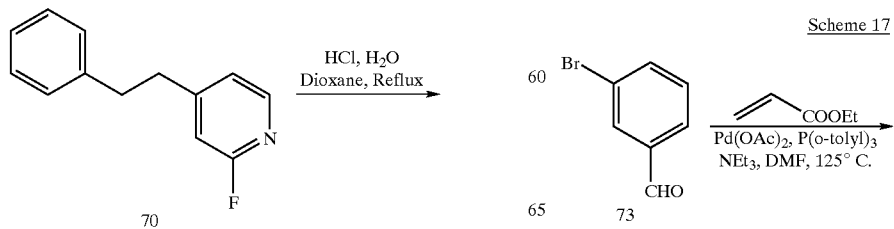

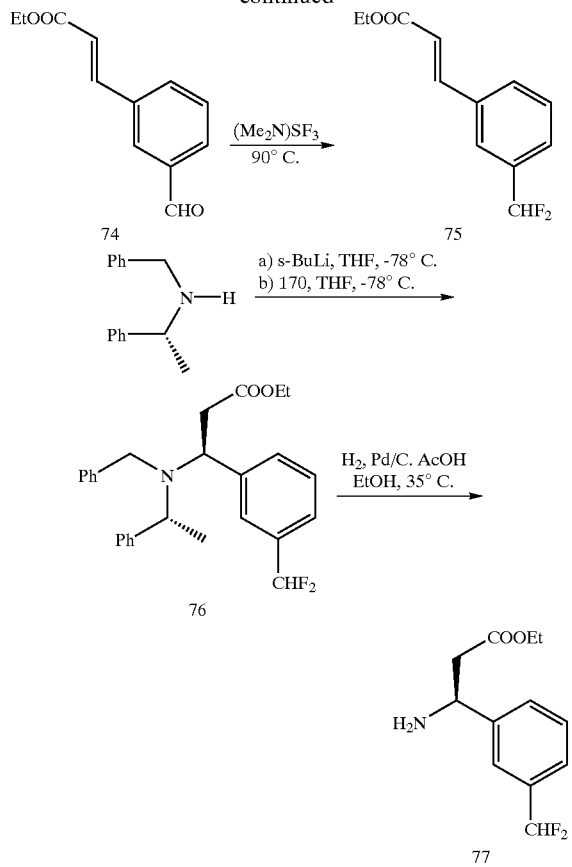

A detailed description of the preparation of representative compounds of the present invention is set forth in the Examples.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrastemal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, or the like.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants. In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary arnmonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono or multi-larnellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention. In another aspect, the present invention contemplates a process of inhibiting the binding of $\alpha_4\beta_1$ integrin to VCAM-1. A process of the present invention can be used either in vitro or in vivo. In accordance with a process of the present invention, a cell expressing $\alpha_4\beta_1$ integrin is exposed to a cell expressing VCAM-1 in the presence of an effective inhibiting amount of a compound of the present invention.

A cell expressing $\alpha_4\beta_1$ integrin can be a naturally occurring white blood cell, mast cell or other cell type that naturally expresses $\alpha_4\beta_1$ on the cell surface, or a cell transfected with an expression vector that contains a polynucleotide (e.g., genomic DNA or cDNA) that encodes $\alpha_4\beta_1$ integrin. In an especially preferred embodiment, $\alpha_4\beta_1$ integrin is present on the surface of a white blood cell such as a monocyte, a lymphocyte or a granulocyte (e.g., an eosinophil or a basophil).

A cell that expresses VCAM-1 can be a naturally occurring cell (e.g. an endothelial cell) or a cell transfected with an expression vector containing a polynucleotide that encodes VCAM-1. Methods for producing transfected cells that express VCAM-1 are well known in the art.

Where VCAM-1 exists on the surface of cell, the expression of that VCAM-1 is preferably induced by inflammatory cytokines such as tumor necrosis factor-$\alpha$, interleukin-4 and interleukin-1$\beta$.

Where the cells expressing $\alpha_4\beta_1$ integrin and VCAM-1 are in a living organism, a compound of the present invention is administered in an effective amount to the living organism. Preferably, the compound is in a pharmaceutical composition of this invention. A process of the present invention is especially useful in treating diseases associated with uncontrolled migration of white blood cells to damaged tissue. Such diseases include, but are not limited to, asthma, atherosclerosis, rheumatoid arthritis, allergy, multiple sclerosis, lupus, inflammatory bowel disease, graft rejection, contact hypersensitivity, type I diabetes, leukemia, and brain cancer. Administration is preferably accomplished via intravascular, subcutaneous, intranasal, transdermal or oral delivery.

The present invention also provides a process of selectively inhibiting the binding of $\alpha_4\beta_1$ integrin to a protein comprising exposing the integrin to the protein in the presence of an effective inhibiting amount of a compound of the present invention. In a preferred embodiment, the $\alpha_4\beta_1$ integrin is expressed on the surface of a cell, either naturally occurring or a cell transformed to express $\alpha_4\beta_1$ integrin.

The protein to which the $\alpha_4\beta_1$ integrin binds can be expressed either on a cell surface or be part of the extracellular matrix. Especially preferred proteins are fibronectin or invasin.

The ability of compounds of the present invention to inhibit binding is described in detail hereinafter in the Examples. These Examples are presented to describe preferred embodiments and utilities of the invention and are not meant to limit the invention unless otherwise stated in the claims appended hereto.

EXAMPLE 1

Compound 8, (3S)-3-(1,3-benzodioxol-5-yl)-3-((2R,S)-2-(3-benzyl-5-methyl-2-oxo-1(2H)-pyridinyl)hexanoylamino) propanoic acid, of the structure shown below, was synthesized as follows.

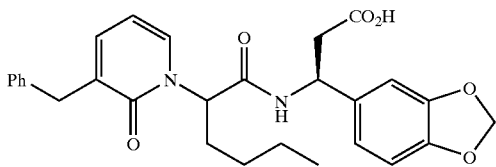

The structures of the compounds identified by number in this Example are found in Scheme 1 above.

Step 1: A solution of 540 mg of 2-aminohexanoic acid methyl ester hydrochloride salt 1 in 20 ml of methylene chloride was washed with excess saturated sodium bicarbonate. The organic layer was separated, dried over magnesium sulfate, and concentrated in vacuo to give 365 mg of 2-aminohexanoic acid methyl ester as a colorless oil. This material was combined with 5 ml of benzene, 0.28 ml of propionaldehyde, and excess magnesium sulfate. After stirring for 15 minutes, the reaction mixture was filtered and concentrated in vacuo to yield 420 mg of compound 2 as a colorless oil. Compound 2 was used directly without further purification.

Step 2: To an ice-bath cooled solution of 1050 mg of compound 2 in 10 ml of diethyl ether, under a positive nitrogen atmosphere, was added 0.80 ml of triethylamine, and a solution of 964 mg of 3-phenylpropanoyl chloride in 2 ml of diethyl ether. The ice bath was removed and the reaction mixture stirred for 30 minutes. The reaction mixture was then concentrated in vacuo and the residual materials further separated by silica gel chromatography using 15% ethyl acetate/hexane as the eluant to yield 468 mg of compound 3 as a colorless oil. Compound 3: $^1$H NMR CDCl$_3$): δ 0.87 (t, J=7.0 Hz, 3H), 1.26 (m, 4H), 1.68 (dd, J=7.0, 1.1 Hz, 3H), 1.74 (m, 1H), 1.97 (m, 1H), 2.70 (t, J=7.9 Hz, 2H), 2.96 (t, J=7.9 Hz, 2H), 3.68 (s, 3H), 4.96 (dd, J.=10.1, 5.3 Hz, 1H), 5.32 (dq, J=13.9, 7.0 Hz, 1H), 6.13 (dd, J=13.9, 1.1 Hz, 1H), 7.20 (m, 2H), 7.25 (m, 3H).

Step 3: N,N-Dimethylformamide (1.63 ml) was added dropwise to an ice-cooled flask containing 4.57 ml of phosphorus oxychloride sealed under a positive nitrogen atmosphere. After 5 minutes, the reaction solution was cannulated into a flask containing 2.22 gm of compound 3. This mixture was stirred at room temperature under a positive nitrogen atmosphere for 2 hours and then heated at 75° C. for 46 hours. The dark-colored reaction mixture was poured over ice and mixed with an excess of sodium bicarbonate and ethyl acetate. The mixture was saturated with sodium chloride and the organic layer separated. The aqueous layer was extracted (3×100 ml) with ethyl acetate. The combined organic materials were dried over magnesium sulfate and concentrated in vacuo to yield 1.70 gm of a dark-colored oil. Methylene chloride extraction (3×) of the aqueous layer yielded an additional 200 mg of material after drying (MgSO$_4$) and condensation in vacuo. The combined residual oils were further purified by silica gel chromatography using 20%–25% ethyl acetate/hexane as the eluant to yield 815 mg of compound 4 as a yellow oil. Compound 4: $^1$H NMR (CDCl$_3$): δ 0.87 (t, J=7.2 Hz, 3H), 1.18 (m, 1H), 1.31 (m, 3H), 1.87 (m, 1H), 2.00 (d, J=0.7 Hz, 3H), 2.16 (m, 1H), 3.72 (s, 3H) 3.85 (br. s, 2H), 5.57 (dd, J=10.1, 5.7 Hz, 1H), 6.82 (br. s, 1H), 6.94 (br. s, 1H), 7.23 (m, 3H), 7.30 (m, 2H).

Step 4: To a solution of 86 mg of compound 4 in 3 ml of tetrahydrofuran was added 1 ml of 2N sodium hydroxide and 2 ml of methanol. After complete hydrolysis, the reaction mixture was acidified with 2N hydrochloric acid and saturated with sodium chloride. The mixture was extracted (3×) with ethyl acetate and the combined extracts were dried with magnesium sulfate and concentrated in vacuo to yield 80 mg of compound 5 as a light yellow oil. Compound 5: $^1$H NMR CDCl$_3$): δ 0.88 (t, J=7.1 Hz, 3H), 1.18 (m, 1H), 1.33 (m, 3H), 2.04 (d, J=0.7 Hz, 3H), 2.07 (m, 1H), 2.27 (m, 1H), 3.86 (d, J=16.1 Hz, 1H), 3.90 (d, J=16.1 Hz, 1H), 5.04 (dd, J=9.0, 6.8 Hz, 1H), 6.96 (br. s, 1H), 6.98 (br. s, 1H), 7.23 (m, 3H), 7.31 (m, 2H).

Step 5: To a solution of 80 mg of compound 5 in 1 ml of N,N-dimethylformamide at room temperature and under a positive nitrogen atmosphere, was added 78 mg of (S)-compound 6, 0.057 ml of diisopropylethylamine, and 137 mg of HBTU. The mixture was stirred for 16 hours and then mixed with 1:1 ethyl acetate/hexane. This mixture was washed with 2N hydrochloric acid, saturated sodium bicarbonate, water (2×), and finally brine. The resulting solution was dried over magnesium sulfate and concentrated in vacuo to yield 156 mg of a yellow oil. This material was further purified by silica gel chromatography using 25% ethyl acetate as the eluant to give 109 mg of compound 7 as a colorless oil. Compound 7: (least polar diastereomer): $^1$H NMR (CDCl$_3$): δ 0.85 (t, J=7.1 Hz, 3H), 1.11 (t, J=7.1 Hz, 3H), 1.18 (m, 1H), 1.30 (m, 3H), 1.78 (m, 1H), 2.02 (d, J=0.8 Hz, 3H), 2.14 (m, 1H), 2.57 (dd, J=15.4, 7.1 Hz, 1H), 2.66 (dd, J=15.4, 6.6 Hz, 1H), 3.86 (br. s, 2H), 3.95 (q, J=7.1 Hz, 2H), 5.17 (m, 1H), 5.42 (t, J=7.7 Hz, 1H), 5 (s, 2H), 6.72 (m, 2H), 6.74 (m, 1H), 6.90 (m, 1H), 7.11 (br. s, 1H), 7.23 (m, 3H), 7.30 (m, 2H), 7.37 (d, J=7.7 Hz, 1H).

Step 6: A solution composed of 109 mg of compound 7, 3 ml of tetrahydrofuran, 1 ml of 2N sodium hydroxide, and 2 ml of methanol was stirred at room temperature until hydrolysis was complete. The mixture was then diluted with water and extracted with diethyl ether. The aqueous layer was acidified with 2N hydrochloric acid and extracted (3×) with ethyl acetate. The combined extracts were dried with magnesium sulfate and concentrated in vacuo to yield 103 mg of compound 8, a 1:1 diasteroisomeric mixture, as an off-white foam.

The diastereomeric mixture was separated by reverse-phase HPLC using a 30–55% acetonitrile/water gradient to yield Compound 9 (R,S) and Compound 10 (S,S).

Compound 9 (most polar diastereomer): $^1$H NMR (CD$_3$SOCD$_3$): δ 0.83 (t, J=7.1 Hz, 3H), 1.13 (m, 2H), 1.26

(m, 2H), 1.76 (m, 1H), 1.96 (s over-lapping m, 4H), 2.62 (dd, J=15.8, 6.6 Hz, 1H), 2.70 (dd, J=15.8, 8.4 Hz, 1H), 3.69 (d, J=14.8 Hz, 1H), 3.73 (d, J=14.8 Hz, 1H), 5.09 (m, 1H), 5.47 (dd, J=9.2, 6.6 Hz, 1H), 6.71 (dd, J=8.0,1.5 Hz, 1H), 6.77 (d, J=8.0 Hz, 1H), 6.84 (d, J=1.5 Hz, 1H), 7.00 (d, J=1.8 Hz, 1H), 7.14–7.30 (m, 6H), 8.70 (d, J=8.1 Hz, 1H).

Compound 10: (least polar diastereomer) NMR (CD$_3$SOCD$_3$): δ 0.76 (t, J=7.3 Hz, 3H), 1.01 (m, 2H), 1.20 (m, 2H), 1.98 (br. s, 3H), 2.60 (dd, J=15.8, 7.0 Hz, 1H), 2.68 (dd, J=15.8, 7.7 Hz, 1H), 3.71 (d, J=15.0 Hz, 1H), 3.76 (d, J=15.0 Hz, 1H), 5.05 (ddd, J=8.0, 7.7, 7.0 Hz, 1H), 5.51 (dd, J=9.2, 6.6 Hz, 1H), 5.98 (s, 2H), 6.77 (dd, 3J=8.0, 1.4 Hz, 1H), 6.83, (d, J=8.0 Hz, 1H), 6.89 (d, J=1.4 Hz, 1H), 7.02 (d, J=2.2 Hz, 1H), 7.18 (m, 1H), 7.25 (m, 4H), 7.38 (m1H), 8.79 (d, J=8.0 Hz, 1H), 12.08 (br. s, 1H).

EXAMPLE 2

Compound 12, (3S)-3-((2R, S)-2-(3-benzyl-5-methyl-2-oxo-1(2H)-pyridinyl)hexanoylamino)-3-(2,3-dihydro-1-benzofutran-5-yl)propanoic acid, shown below, was synthesized according to the procedure of Example 1, except that compound A, shown below, was substituted for compound 6 in step 5.

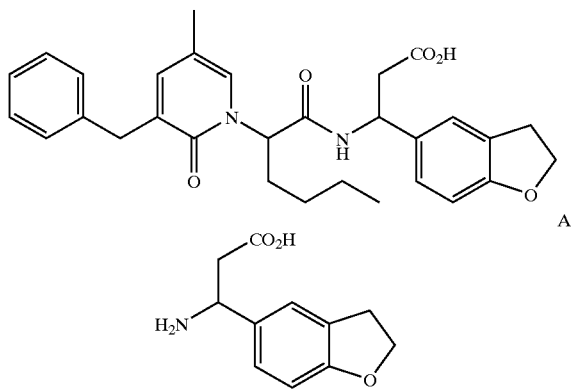

A

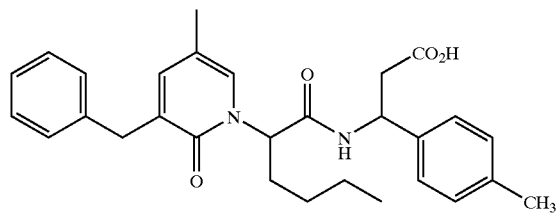

EXAMPLE 3

Compound 13, (3S)-3-((2R,S)-2-(3-benzyl-5-methyl-2-oxo-1(2H)-pyridinyl)hexanoylamino)-3-(4-methylphenyl) propanoic acid, shown below,was obtained by the procedure of Example 1,

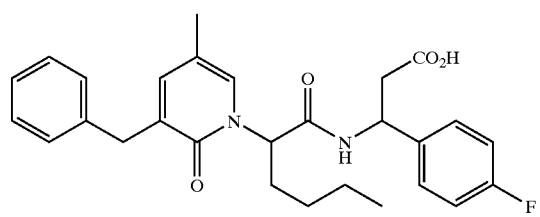

except that compound B, shown below, was substituted for compound 6 in step 5.

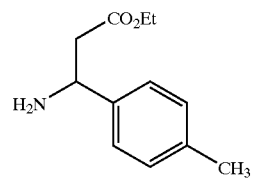

B

EXAMPLE 4

Compound 14, (3S)-3-((2R,S)-2-(3-benzyl-5-methyl-2-oxo-1(2H)-pyridinyl)hexanoylamino)-3-(4-fluorophenyl) propanoic acid, shown below was obtained by the procedure of Example 1,

14 except that compound 11, shown below, was substituted for compound 6 in step 5.

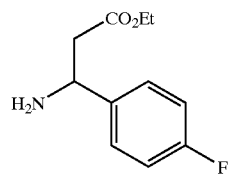

11

EXAMPLE 5

Compound 15, (3S)-3-(1,3-benzodioxol-5-yl)-3-((2R,S)-2-(3-(4-methoxybenzyl)-5-methyl-2-oxo-1(2H)-pyridinyl) hexanoylamino)propanoic acid, shown below, can be obtained by the procedure of Example 1,

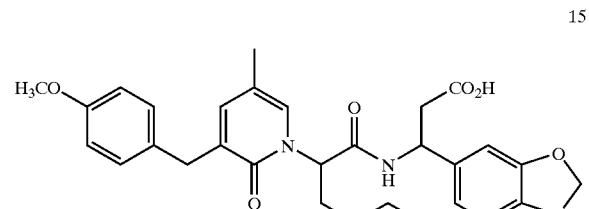

15 except that 3-(4-methoxyphenyl)-propanoyl chloride should be substituted for 3-phenylpropanoyl chloride in step 2.

EXAMPLE 6

Compound 16, (3S)-3-(1,3-benzodioxol-5-yl)-3-((2R,S)-2-(3-(4-methylbenzyl)-5-methyl-2-oxo-1(2H)-pyridinyl)hexanoylamino)propanoic acid, shown below can be obtained by the procedure of Example 1,

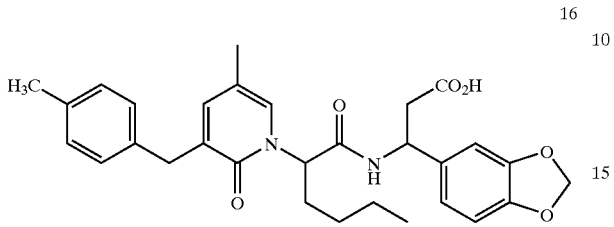

16 except that 3-(4-methylphenyl)-propanoyl chloride should be substituted for 3-phenylpropanoyl chloride in step 2.

EXAMPLE 7

Compound 17, (3S)-3-(1,3-benzodioxol-5-yl)-3-((2R,S)-2-(3-(4-fluorobenzyl)-5-methyl-2-oxo-1(2)-pyridinyl)hexanoylamino)propanoic acid, shown below, was obtained by the procedure of Example 1,

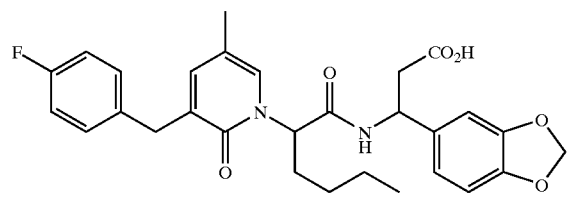

17 except that 3-(4-fluorophenyl)-propanoyl chloride was substituted for 3-phenylpropanoyl chloride in step 2.

EXAMPLE 8

Compound 18, (3S)-3-(1,3-benzodioxol-5-yl)-3-((2R,S)-2-(3-(4-chlorobenzyl)-5-methyl-2-oxo-1(2H)-pyridinyl)hexanoylamino)propanoic acid, shown below was obtained by the procedure of Example 1,

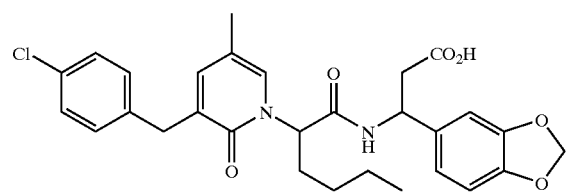

18 except that 3-(4-chlorophenyl)-propanoyl chloride was substituted for 3-phenylpropanoyl chloride in step 2.

EXAMPLE 9

Compound 19, (3S)-3-(1,3-benzodioxol-5-yl)-3-((2R,S)-2-(3-(3-chlorobenzyl)-5-methyl-2-oxo-1(2H)-pyridinyl)hexanoylamino)propanoic acid, shown below was obtained by the procedure of Example 1,

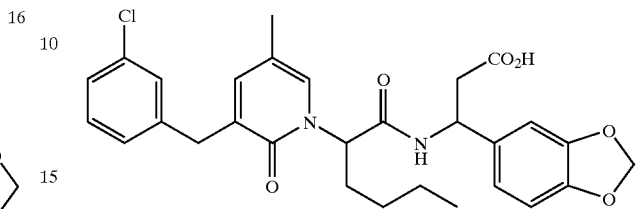

19 except that 3-(3-chlorophenyl)-propanoyl chloride was substituted for 3-phenylpropanoyl chloride in step 2.

EXAMPLE 10

Synthesis of (3S)-3-(1,3-benzodioxol-5-yl)-3-({(2S)-2-[2-oxo-3-(2-thienylmethyl)-1-imidazolidinyl]hexanoyl}amino)propanoic acid (20).

Step One: To a solution of 6 (680 mg, 2.87 mmol) and N-tert-butoxycarbonyl-L-norleucine (696 mg, 3.01 mmol) in DMF (14.4 ml) at room temperature under a dry nitrogen atmosphere, N, N-diisopropylethylamine (0.52 ml, 3.0 mmol) and HBTU (1.25 g, 3.3 mmol) were added sequentially. The resulting mixture was stirred at room temperature overnight then was diluted with a 1:1 mixture of hexanes-:ethyl acetate and washed 2N HCl, $H_2O$, saturated $NaHCO_3$, $H_2O$ (3×) and brine. The organic phase was dried over $MgSO_4$ and filtered and the filtrate was concentrated under reduced pressure to give 22 (1.27 g, 98%) as a light yellow solid.

Step Two: To a flask containing 22 (1.27 g, 2.82 mmol) sealed with a rubber septum at room temperature under a dry nitrogen atmosphere, HCl (7.2 ml, 4.0M in dioxane, 28.8 mmol) was added by syringe. The nitrogen needle was removed and the mixture in the sealed flask was stirred for 1 hour. The mixture was diluted with $CH_2Cl_2$ and washed with saturated $NaHCO_3$. The organic phase was dried over $MgSO_4$ and filtered and the filtrate was concentrated under reduced pressure to give 23 (892 mg, 90%) as a light yellow oil.

Step Three: To a solution of ethanolamine (1.70 g, 27.8 mmol) and 2-thiophenecarboxaldehyde (0.52 ml, 5.6 mmol) in 1,2-dichloroethane (22 ml) at room temperature under a dry nitrogen atmosphere, sodium triacetoxyborohydride (1.66 g, 7.8 mmol) was added. The resulting mixture was stirred at room temperature overnight then was diluted with $CH_2Cl_2$ and washed with a 1:1 mixture of saturated $NaHCO_3$ and brine. The aqueous phase was extracted with $CH_2Cl_2$ and the organic phases were combined, dried over $MgSO_4$ and filtered. The filtrate was concentrated under reduced pressure to give 24 (840 mg, 97%) as a pale yellow oil.

Step Four: A solution of aminal 24 (840 mg, 5.41 mmol) in methanol (10 ml) was stirred at room temperature for 30 minutes, cooled to 0° C. and then sodium borohydride (106 mg, 2.8 mmol) was added. The mixture was allowed to warm to room temperature and was then stirred for 1 hour. The mixture was quenched by dropwise addition of water then diluted with $CH_2Cl_2$ and a 1:1 mixture of saturated $NaHCO_3$ and brine. The aqueous phase was extracted with CH₂Cl₂ (2×) and the organic phases were combined, dried over MgSO₄ and filtered. The filtrate was concentrated under reduced pressure to give 25 (420 mg, 49%) as a pale yellow viscous oil.

Step Five: A solution of 25 (420 mg, 2.67 mmol) and di-tert-butyl dicarbonate (650 mg, 2.98 mmol) in CH₂Cl₂ (10 ml) was stirred at room temperature under a dry nitrogen atmosphere for 20 minutes and then concentrated. The residue was filtered though silica gel, eluting with 7:3 hexanes:ethyl acetate increasing to 3:2 hexanes:ethyl acetate to yield 26 (610 mg, 88%) as a colorless, viscous oil.

Step Six: To a solution of methylsulfoxide (0.49 ml, 6.9 mmol) in CH₂Cl₂ (11 ml) cooled to −78° C. under a dry nitrogen atmosphere, oxalyl chloride (1.7 ml, 2.0 M in CH₂Cl₂, 3.4 mmol) was added by syringe. The resulting mixture was stirred at −78° C. for 15 minutes, then a solution of 26 (590 mg, 2.3 mmol) in CH₂Cl₂ (10 ml) was added by cannula along with a CH₂Cl₂ (5 ml) rinse. The mixture was stirred at −78° C. for 30 minutes, triethylamine (0.96 ml, 6.9 mmol) was added and the mixture was allowed to warm to room temperature. The mixture was diluted with CH₂Cl₂ and washed with saturated NaHCO₃. The organic phase was dried over MgSO₄ and filtered and the filtrate was concentrated under reduced pressure to give 27 (630 mg) as a light yellow oil. This material was used without purification.

Step Seven: To a solution of 27 (102 mg, 0.40 mmol) and 23 (140 mg, 0.40 mmol) in 1,2-dichloroethane (4 ml) at room temperature under a dry nitrogen atmosphere, sodium triacetoxyborohydride (119 mg, 0.56 mmol) was added. The resulting mixture was stirred for 2 hours, then was diluted with ethyl acetate and washed with saturated NaHCO₃ and brine. The organic phase was dried over MgSO₄ and filtered and the filtrate was concentrated under reduced pressure to give 28 (232 mg) as a light yellow oil. This material was used without purification.

Step Eight: To a flask containing 28 (232 mg crude material, 0.40 mmol theoretical from previous step) sealed with a rubber septum at room temperature under a dry nitrogen atmosphere, HCl (1.95 ml, 4.0M in dioxane, 7.8 mmol) was added by syringe. The nitrogen needle was removed and the mixture in the sealed flask was stirred for 15 minutes. The mixture was diluted with CH₂Cl₂ and washed with a 1:1 mixture of saturated NaHCO3:brine. The organic phase was dried over MgSO₄ and filtered and the filtrate was concentrated under reduced pressure to give 29 (180 mg) as a light yellow oil. This material was used without purification.

Step Nine: To a solution of 29 (180 mg crude material, 0.40 mmol theoretical from previous step) in 1,2-dichloroethane (3.7 ml) at room temperature under a dry nitrogen atmosphere, carbonyldiimidazole (66 mg, 0.41 mmol) was added. The mixture was heated to 50° C. (oil bath temperature) for 1 hour, the was concentrated. The residue was taken up in ethyl acetate and washed with 2N HCl, H₂), saturated NaHCO₃ and brine. The organic phase was dried over MgSO₄ and filtered and the filtrate was concentrated under reduced pressure. The residue was filtered through silica gel, eluting with 3:2 hexanes:ethyl acetate increasing to 1:1 hexanes:ethyl acetate to yield 30 (114 mg, 55% for 3 steps) as a colorless oil.

Step Ten: To a solution of 30 (114 mg, 0.22 mmol) in THF (3 ml) at room temperature, NaOH (1 ml, 2N in H₂O, 2 mmol) and methanol (enough to give a clear solution, approximately 2 ml) were added. The resulting mixture was stirred for 15 minutes, then was diluted with water and extracted with ether. The aqueous phase was acidified with HCl (2N) and extracted with ethyl acetate. The ethyl acetate layer was washed with brine, dried over MgSO₄ and filtered and the filtrate was concentrated under reduced pressure to give 20 (111 mg, 100%) as a white foam. ¹H NMR (400 MHz, CD₃SOCD₃): δ 0.82 (t, J=7.3 Hz, 3H), 1.09 (m, 2H), 1.25 (m, 2H), 1.48 (m, 1H), 1.64 m, 1H), 2.61 (dd, J=15.8, 7.0 Hz, 1H), 2.70 (dd, J=15.8, 8.0 Hz, 1H), 3.20 (m, 3H), 3.50 (m, 1H), 4.27 (dd, J=9.5, 5.9 Hz, 1H), 4.38 (d, J=15.6 Hz, 1H), 4.54(d, J=15.6 Hz, 1H), 5.08 (ddd, J=8.1, 8.0, 7.0 Hz, 1H), 5.91 (s, 2H), 6.76 (dd, J=8.0, 1.5 Hz, 1H), 6.83 (d, J=8.0 Hz, 1H), 6.88 (d, J=1.5 Hz, 1H), 6.99 (m, 2H), 7.43 (dd, J=4.4, 1.8 Hz, 1H), 8.43 (d, J=8.1 Hz, 1H).

Synthetic procedures similar to those described above may be utilized to obtain the following compounds: (3S)-(1,3-benzodioxol-5-yl)-3-(((2S)-2-(2-oxo-3-(2-thienylmethyl)tetrahydro-1(2H)-pyrimidinyl)hexanoyl)amino) propanoic acid, (3S)-3-(1,3-benzodioxol-5-yl)-3-(((2S)-2-(2-oxo-4-(2-thienyl)-3-(2-thienylmethyl)tetrahydro-1((2H)-pyrimidinyl)hexanoyl)amino)propanoic acid and (3S)-3-(1,3-benzodioxol-5-yl)-3-(((2S)-2-(2-oxo-3-(2-thienylmethyl)-1,3-diazepan-1-yl)hexanoyl)amino) propanoic acid.

EXAMPLE 11

Synthesis of (3S)-3-(1,3-benzodioxol-5-yl)-3-({(2S)-2-[2-oxo-3-(phenylcarbonyl)-1(2H)-pyridinyl]hexanoyl}amino)propanoic acid (31).

31

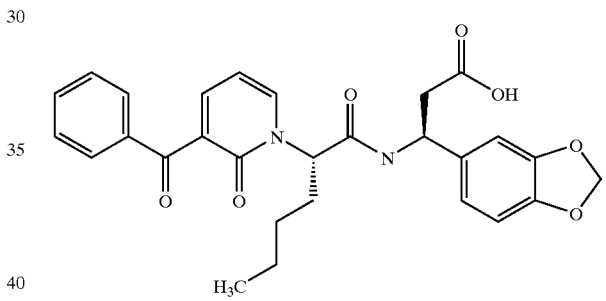

Step One: A solution of 23 (541 mg, 1.54 mmol) and ethyl benzoylacetate (0.53 mL, 3.09 mmol) in toluene (15 mL) was heated to reflux for 2 hours. The resulting mixture was cooled to room temperature and concentrated under reduced pressure. The residue was recrystallized from hexanes/CH₂Cl₂ to give compound 32 (310 mg, 40%) as a pale yellow solid.

Step Two: To a suspension of 32 (851 mg, 1.71 mmol) in ethanol (absolute, 6.8 mL) and acetic acid (glacial, 0.34 mL) at room temperature under nitrogen, 3-(dimethylamino)acrolein (1.02 mL, 10.2 mmol) was added by syringe. The resulting mixture was heated to reflux overnight, cooled to room temperature and diluted with ethyl acetate. This mixture was washed with HCl (2N, twice) and brine. The organic phase was dried over MgSO₄ and filtered and the filtrate was concentrated under reduced pressure. The residue was purified by silica gel chromatography, eluting with 3:2 hexanes:ethyl acetate to give 33 (476 mg, 52%) as a light yellow oil.

Step Three: To a solution of 33 (115 mg, 0.22 mmol) in THF (6 mL) at room temperature, aqueous NaOH (2N, 2 mL) and methanol (4 mL) were added. The resulting solution was stirred for 15 minutes, diluted with water and extracted with Et₂O. The aqueous phase was acidified with HCl (2N) and was extracted with ethyl acetate. The ethyl acetate layer was washed with water and brine, dried over MgSO$_4$ and filtered. The filtrate was concentrated under reduced pressure to give (3S)-3-(1,3-benzodioxol-5-yl)-3-({(2S)-2-[2-oxo-3-(phenylcarbonyl)-1(2H)-pyridinyl]hexanoyl}amino)propanoic acid (31, 100 mg, 92%) as a pale yellow foam. $^1$H NMR (400 MHz, CD$_3$SO$_2$CD$_3$): δ 0.81 (t, J=7.3 Hz, 3H), 1.08 (m, 2H), 1.25 (m, 2H), 1.80 (m, 1H), 1.93 (m, 1H), 2.61 (dd, J=15.8, 6.8 Hz, 1H), 2.68 (dd, J=15.8, 7.9 Hz, 1H), 5.09 (m, 1H), 5.49 (dd, J=9.5, 6.2 Hz, 1H), 5.98 (s, 2H), 6.24 (t, J=7.0 Hz, 1H), 6.78 (dd, J=8.1, 1.4 Hz 1H), 6.84 (d, J=8.1 Hz, 1H), 6.89 (d, J=1.4 Hz, 1H), 7.49 (t, J=7.7 Hz, 2H), 7.62 (m, 1H), 7.70 (m, 3H), 7.97 (dd, J=7.0, 2.2 Hz, 1H), 8.87 (d, J=8.1 Hz, 1H), 12.11 (br. s, 1H).

EXAMPLE 12

Synthesis of (3S)-3-(1,3-benzodioxol-5-yl)-3-({(2S)-2-[2-oxo-3-(phenylmethyl)-1(2H)-pyridinyl]hexanoyl}amino)propanoic acid (34).

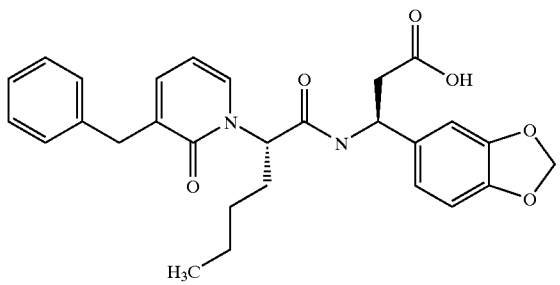

34

Step One: To a solution of 33 (88 mg, 0.17 mmol) in ethanol (absolute, 4 mL) at room temperature, NaBH$_4$ (12.5 mg, 0.33 mmol) was added. The resulting mixture was stirred for 20 minutes, then was quenched with HCl (2N, 2 mL). The resulting mixture was diluted with water and ethyl acetate and the organic layer was washed with saturated aqueous NaHCO$_3$ and brine. The organic layer was dried over MgSO$_4$ and filtered and the filtrate was concentrated under reduced pressure to give 35 (85 mg, 96%) as a pale yellow oil. This material was used without purification.

Step Two: To a solution of 35 (85 mg, 0.16 mmol) in ethyl acetate (4 mL) at room temperature under nitrogen, Pd/C (10% dry weight basis, Degussa type E101 NE/W, ~50% water content, 36 mmol) was added. The atmosphere was replaced with hydrogen (toggle between vacuum and hydrogen from a balloon five times) and the mixture was vigorously stirred for 1.5 hours. The mixture was filtered through Celite and the filtrate was concentrated under reduced pressure. The residue was purified by silica gel chromatography, eluting with 7:3 hexanes:ethyl acetate to give 36 (32 mg, 39%) as a colorless oil.

Step Three: To a solution of 36 (32 mg, 0.062 mmol) in THF (3 mL) at room temperature, aqueous NaOH (2N, 1 mL) and methanol (2 mL) were added. The resulting solution was stirred for 15 minutes, diluted with water and extracted with Et$_2$O. The aqueous phase was acidified with HCl (2N) and was extracted with ethyl acetate. The ethyl acetate layer was washed with water and brine, dried over MgSO$_4$ and filtered. The filtrate was concentrated under reduced pressure. The residue was taken up in acetonitrile (3 mL) and water (7 mL) and the mixture was lyophilized to give (3S)-3-(1,3-benzodioxol-5-yl)-3-({(2S)-2-[2-oxo-3-(phenylmethyl)-1(2H)-pyridinyl]hexanoyl}amino)propanoic acid (34, 31 mg, 100%) as a white powder. $^1$H NMR (400 MHz, CD$_3$SO$_2$CD$_3$): δ 0.76 (t, J=7.3 Hz, 3H), 1.01 (m, 2H), 1.22 (m, 2H), 1.70 (m, 1H), 1.87 (m, 1H), 2.60 (dd, J=15.8, 7.0 Hz, 1H), 2.68 (dd, J=15.8, 7.9 Hz, 1H), 3.72 (d, J=15.0 Hz, 1H), 3.77 (d, J=15.0 Hz, 1H), 5.06 (m, 1H), 5.54 (dd, J=9.2, 6.6 Hz, 1H), 5.98 (s, 2H), 6.16 (t, J=7.0 Hz, 1H), 6.77 (dd, J=8.1, 1.4 Hz, 1H), 6.83 (d, J=8.1 Hz, 1H), 6.89 (d, J=1.4 Hz, 1H), 7.13 (m, 1H), 7.18 (m, 1H), 7.26 (m, 4H), 7.59 (dd, J=7.0, 1.8 Hz, 1H), 8.83 (d, J=8.1 Hz, 1H), 12.11 (br. s, 1H).

EXAMPLE 13

Synthesis of (3S)-3-(1,3-benzodioxol-5-yl)-3-[({1-[2-oxo-3-(phenylmethyl)-1(2H)-pyridinyl]cyclohexyl}carbonyl)amino]propanoic acid.

Step One: To a solution of 3-benzylpyridine (1.65 g, 9.77 mmol) in acetone (3.5 mL), 1-chloro-2,4-dinitrobenzene (2.00 g, 9.56 mmol) was added and the mixture was refluxed overnight. The mixture was cooled to room temperature, diluted with acetone and the solvent was decanted from the precipitate. The crude solid was washed with acetone (2 times) and diethyl ether (1 time), decanting each time to give 37 (3.57 g, 100%) as a gray solid.

Step Two: To a solution of 1-amino-1-hydroxymethylcyclohexane (0.45 g, 3.5 mmol) in n-butanol (8.75 mL), solid N-(2,4-dintrophenyl)-3-benzylpyridinum chloride (37, 1.23 g, 3.3 mmol) was added. The resulting solution was heated to reflux for 2.5 days under a nitrogen atmosphere. The mixture was cooled, diluted with water and filtered. The filtrate was basified with concentrated NH$_4$OH (2 mL) and extracted with ethyl acetate. The aqueous layer was concentrated to dryness to give 38 (0.56 g) as a yellow oil which was used without further purification.

Step Three: To a solution of crude 38 (0.56 g, 3.5 mmol theoretical) in water (10 mL), a solution of potassium ferricyanide (3.3 g, 10 mmol) in water (15 mL) was added dropwise via an addition funnel over 30 minutes at 0° C. A solution of KOH (0.76 g, 13.5 mmol) in water (5 mL) was then added over 30 minutes. Toluene (10 mL) was added and the solution was stirred for one hour at 0° C. The layers were separated, and the aqueous layer was extracted again with toluene. The combined extracts were dried over Na$_2$SO$_4$ and filtered and the filtrate was concentrated under reduced pressure. The residue was chromatographed on silica gel, eluting with 7:13 hexanes:ethyl acetate to give 39 (20 mg, 1.9%, two steps.)

Step Four: To a suspension of 39 (20 mg, 0.068 mmol) in aqueous KOH (1M, 0.70 mL) potassium persulfate (0.073 g, 0.270 mmol) and ruthenium (III) chloride (1 mg, catalytic) and THF (0.25 mL) were added. The mixture was stirred for 1 hour and extracted with dichloromethane. The aqueous layer was acidified and extracted with ethyl acetate (3 times). The ethyl acetate extracts were combined, dried over MgSO$_4$ and filtered. The filtrate was concentrated under reduced pressure to give 40 (0.0148 g, 70%) as a tan solid. (3S)-3-(1,3-Benzodioxol-5-yl)-3-[({1-[2-oxo-3-(phenylmethyl)-1(2H)-pyridinyl]cyclohexyl}carbonyl)amino]propanoic acid was prepared from 40 according to the procedures described in Example 1. $^1$H NMR (400 MHz, CD$_3$SO$_2$CD$_3$): δ 1.40 (m, 4H), 1.68 (m, 2H), 2.04 (m, 2H), 2.60 (d, J=7.0 Hz, 2H), 3.67 (d, J=15.2 Hz, 1H), 3.72 (d, J=15.2 Hz, 1H), 5.12 (m, 1H), 5.95 (m, 2H), 6.19 (t, J=7.0 Hz, 1H), 6.74 (dd, J=7.8, 1.4 Hz, 1H), 6.76 (d, J=7.8 Hz, 1H), 6.90 (d, J=1.4 Hz, 1H), 7.10 (d, J=5.8 Hz, 1H), 7.20 (m, 5H), 7.57 (d, J=8.4 Hz, 1H), 7.66 (dd, J=7.7, 1.8 Hz, 1H).

EXAMPLE 14

Synthesis of (3S)-3-(1,3-benzodioxol-5-yl)-3-({2-[2-oxo-5-(phenylmethyl)-1(2H)-pyridinyl]hexanoyl}amino)propanoic acid.

Step One: To a mixture of 41 (prepared according to procedures described in Example 13, 1.75 g crude orange oil, 5.0 mmol theoretical) in water (25 mL) at 0° C., a solution of potassium ferricyanide (4.7 g, 14 mmol) in water (22 mL) was added dropwise via an addition funnel over 30 minutes. A solution of KOH (1.1 g, 19 mmol) in water (7 mL) was then added over 30 minutes. Toluene (15 mL) was added and the solution was stirred for one hour at 0° C. The layers were separated, and the aqueous layer was extracted again with toluene. The combined extracts were dried over $Na_2SO_4$ and filtered and the filtrate was concentrated under reduced pressure. The residue was chromatographed on silica gel, eluting with 7:13 hexanes:ethyl acetate to give 42 (major product, 0.36 g, 29%) and 43 (minor product, 0.10 g, 7.0%).

(3S)-3-(1,3-Benzodioxol-5-yl)-3-({2-[2-oxo-5-(phenylmethyl)-1(2H)-pyridinyl]hexanoyl}amino)propanoic acid was prepared from 42 according to procedures described in Examples 1 and 13. $^1$H NMR (400 MHz, $CD_3SO_2CD_3$) δ 0.77 (t, J=7.3 Hz, 3H), 1.00 (m, 2H), 1.20 (m, 2H), 1.75 (m, 1H), 1.88 (m, 1H), 2.65 (m, 2H), 3.70 (s, 2H), 5.08 (m, 1H), 5.49 (dd, J=9.9, 6.2 Hz, 1H), 5.98 (s, 2H), 6.32 (d, J=9.2 Hz, 1H), 6.77 (dd, J=8.1, 1.5 Hz, 1H), 6.83 (d, J=9.2 Hz, 1H), 6.89 (d, J=1.5 Hz, 1H), 7.20 (m, 4H), 7.28 (m, 4H), 7.61 (d, J=2.6 Hz, 1H), 8.81 (d, J=8.1 Hz, 1H), 12.10 (br. s, 1H).

EXAMPLE 15

Synthesis of (3S)-3-(1,3-benzodioxol-5-yl)-3-({(2S)-2-[(3S)-2,5-dioxo-3-(phenylmethyl)-4-(2-thiophenylmethyl)tetrahydro-1(2H)-pyrazinyl]hexanoyl}amino)propanoic acid.

Step 1: To a solution of phenylalanine methyl ester (2.32 g, 12.9 mmol) in DCE (50 ml) at room temperature, 2-thiophenecarboxaldehyde (1.2 ml, 12.9 mmol) and NaBH(OAc)$_3$ (4.11 g, 19.4 mmol) were added. The reaction stirred at room temperature for 24 hours, diluted with $CH_2Cl_2$ (300 ml) and washed with water (300 ml). The organic layer was dried over $MgSO_4$ and filtered and the filtrate was concentrated under reduced pressure. The residue was purified by silica gel chromatography, eluting with 9:1 hexanes:ethyl acetate to yield 44 (2.78 g, 78%).

Step 2: To a solution of 44 (1.50 g, 5.45 mmol) in methanol (10 ml), tetrahydrofuran (10 ml) and water (10 ml), sodium hydroxide (880 mg, 21.8 mmol) was added. The reaction was stirred at room temperature for 48 hours. The mixture was concentrated under reduced pressure to an aqueous solution and then lyophilized to yield 45 (1.42 g).

Step 3: To a solution of 45 (500 mg, 1.91 mmol) and norleucine methyl ester hydrochloride (382 mg, 2.10 mmol) in DMF (10 ml) at room temperature, 1-[3-(dimethylamino)propyl]-3-ethylcarbodiimide hydrochloride (401 mg, 2.10 mmol), 1-hydroxybenzotriazole (238 mg, 2.10 mmol) and 4-methylmorpholine (0.23 ml, 2.10 mmol) were added. The reaction stirred at room temperature for 24 hours then the mixture was taken up in ethyl acetate (200 ml) and washed with water (2 times, 200 ml). The organic layer was dried over $MgSO_4$ and filtered and the filtrate was concentrated under reduced pressure. The residue was purified by silica gel chromatography, eluting with 9:1 hexanes:ethyl acetate to yield 46 (422 mg, 57%).

Step 4: To a solution of 46 (415 mg, 1.07 mmol) DCE (10 ml) and triethylamine (0.15 ml, 1.07 mmol) at 0° C., bromoacetyl bromide (0.090 ml, 1.07 mmol) was added and the reaction was warmed to room temperature and stirred for 24 hours. The mixture was taken up in $CH_2Cl_2$ (150 ml) and washed with water (150 ml). The organic layer was dried over $MgSO_4$ and filtered and the filtrate was concentrated under reduced pressure. The residue was purified by silica gel chromatography, eluting with 4:1 hexanes:ethyl acetate to yield 47 (381 mg, 70%).

Step 5: To a solution of 47 (375 mg, 0.74 mmol) in THF (8 ml), $Cs_2CO_3$ (360 mg, 1.10 mmol) was added. The reaction was stirred at room temperature for 4 hours. The mixture was taken up in ethyl acetate (150 ml) and washed with water (150 ml) The organic layer was dried over $MgSO_4$ and filtered and the filtrate was concentrated under reduced pressure. The residue was purified by silica gel chromatography, eluting with 4:1 hexanes:ethyl acetate to yield 48 (145.0 mg, 46%). (3S)-3-(1,3-benzodioxol-5-yl)-3-({(2S)-2-[(3S)-2,5-dioxo-3-(phenylmethyl)-4-(2-thiophenylmethyl)tetrahydro-1(2H)-pyrazinyl]hexanoyl}amino)propanoic acid was prepared from 48 according to procedures described in Example 1. MS: Calculated: (M–H)$^-$=604.2 m/z; Found: (M–H)$^-$=604.4 m/z.

EXAMPLE 16

Synthesis of (3S)-3-(1,3-benzodioxol-5-yl)-3-({2-[2-oxo-3-(phenylmethyl)-2,3-dihydro-1H-benzimidazol-1-yl]acetyl}amino)propanoic acid.

Step One: A mixture of 1-fluoro 2-nitrobenzene (0.50 g, 3.54 mmol), benzylamine (0.38 g, 3.54 mmol) and $K_2CO_3$ (0.98 g, 7.08 mmol) in DMF (10 mL) was stirred at room temperature overnight. The mixture was then partitioned between EtOAc and water. The organic layer was washed with water and brine, dried over $MgSO_4$ and filtered. The filtrate was concentrated to dryness to give 49 (0.79 g, 98%) as an orange solid.

Step Two: To a solution of 49 (0.79 g, 3.5 mmol) in ethanol (7.0 mL) and acetic acid (7.0 mL) at room temperature, Fe powder (2.44 g, 34.6 mmol) was added and the suspension was stirred vigorously at 40° C. until thin layer chromatography indicated complete consumption of 49. The mixture was filtered through Celite, washing with chloroform. The filtrate was diluted with saturated sodium bicarbonate and the chloroform layer was dried over $Na_2SO_4$ and filtered. The filtrate was concentrated under reduced pressure and the residue was purified by chromatography on silica gel (4:1 increasing to 1:1 hexanes:ethyl acetate) to give compound 50 (0.35 g, 50%)

Step Three: A solution of 50 (0.25 g, 1.26 mmol) and CDI (0.22 g, 1.4 mmol) in $CH_2Cl_2$ (12 mL) was stirred at room temperature overnight. The mixture was diluted with EtOAc and was washed with 1N HCl (3×) and brine. The organic layer was dried over $MgSO_4$ and filtered and the filtrate was concentrated under reduced pressure to give 51 (0.23 g, 82%) as a brown solid.

Step Four: To a solution of 51 (0.19 g, 0.85 mmol) in anhydrous DMF (5 mL) at 0° C. was added NaH (60% dispersion in mineral oil, 0.044 g, 1.1 mmol). The mixture was stirred at 0° C. for 10 minutes before the addition of ethyl bromoacetate (0.21 g, 0.13 mmol). After stirring at room temperature overnight, the mixture was poured into ice-water and extracted with EtOAc (2 times). The organic layer was washed with water and brine, dried over $MgSO_4$ and filtered. The filtrate was concentrated under reduced pressure to give 52 (0.25 g, 95%) as a brown solid.

(3S)-3-(1,3-benzodioxol-5-yl)-3-({2-[2-oxo-3-(phenylmethyl)-2,3-dihydro-1H-benzimidazol-1-yl]acetyl}amino)propanoic acid was prepared from 52 according to procedures described in Example 1. $^1$H NMR (400 MHz, CD$_3$COCD$_3$): δ 2.79 (m, 2H), 4.56 (m, 2H), 5.02 (s, 2H), 5.31 (m, 1H), 5.90 (s, 2H), 6.92 (m, 7H), 7.25 (m, 5H), 7.91 (d, J=8.4 Hz, 1H), 10.79 (br. S, 1H).

EXAMPLE 17

Synthesis of (3S)-3-(1,3-benzodioxol-5-yl)-3-({2-[5,5-dimethyl-2,4-dioxo-3-(phenylmethyl)tetrahydro-1H-imidazol-1-yl]hexanoyl}amino) propanoic acid.

Step One: To a solution of 5,5-dimethylhydantoin (2.00 g, 15.6 mmol) in DMF (30 mL) at room temperature, K$_2$CO$_3$ (6.5 g, 47 mmol) and benzyl chloride (2.20 mL, 18.7 mmol) were added. The resulting mixture was stirred overnight, diluted with water and extracted with ethyl acetate. The organic layer was washed with brine, dried over MgSO$_4$ and filtered. The filtrate was concentrated under reduced pressure and the residue was purified by silica gel chromatography, eluting with 6:1 increasing to 3:1 hexanes:ethyl acetate to yield 53 (3.21 g, 94%).

(3S)-3-(1,3-benzodioxol-5-yl)-3-({2-[5,5-dimethyl-2,4-dioxo-3-(phenylmethyl)tetrahydro-1H-imidazol-1-yl]hexanoyl}amino)propanoic acid was prepared from 53 according to procedures described in Examples 1 and 16. MP: 53–55° C.

EXAMPLE 18

Synthesis of (3S)-3-(1,3-benzodioxol-5-yl)-3-({(2S)-2-[2,4-dioxo-1-(phenylmethyl)-1,4-dihydro-3(2H)-quinazolinyl]hexanoyl}amino)propanoic acid.

Step One: To a solution of anthranillic acid (450 mg, 3.30 mmol) and norleucine methyl ester hydrochloride (500 mg, 2.75 mmol) in dimethylformamide (10 ml) at room temperature, 1-[3-(dimethylamino) propyl]-3-ethylcarbodiimide hydrochloride (640 mg, 3.30 mmol), 1-hydroxybenzo triazole (450 mg, 3.30 mmol), and 4-methylmorpholine (610 mg, 5.50 mmol) were added. The reaction was stirred at room temperature for 24 hours then the mixture was taken up in ethyl acetate (200 ml) and washed with water (2×200 ml). The organic layer was dried over MgSO$_4$ and filtered and the filtrate was concentrated under reduced pressure. The residue was purified by silica gel chromatography, eluting with 4:1 increasing to 1:1 hexanes:ethyl acetate to yield 54 (860 mg, 99%).

Step Two: A solution of 54 (0.86 g, 3.26 mmol) and CDI (0.79 g, 4.89 mmol) in anhydrous ClCH$_2$CH$_2$Cl (30 mL) was heated at 85° C. overnight. The mixture was cooled to room temperature and concentrated and the residue was brought up in EtOAc. The organic layer was washed with 1N HCl (3×) and brine, dried over MgSO$_4$ and filtered. The filtrate was then concentrated under reduced pressure and the residue was purified by silica gel chromatography (hexanes:EtOAc, 5:1 increasing to 1:1) to give 55 as a white solid (0.67 g, 71%). (3S)-3-(1,3-benzodioxol-5-yl)-3-({(2S)-2-[2,4-dioxo-1-(phenylmethyl)-1,4-dihydro-3(2H)-quinazolinyl]hexanoyl}amino)propanoic acid was prepared from 55 according to procedures outlined in Examples 1 and 16. $^1$H NMR (400 MHz, CD$_3$SO$_2$CD$_3$): δ 0.80 (m, 3H), 1.1–1.6 (m, 4H), 2.03 (m, 1H), 2.20 (m, 1H), 2.63 (m, 2H), 5.20 (m, 2H), 5.35 (m, 1H), 5.47 (m, 1H), 5.91 (d, J=11.0 Hz, 1H), 5.96 (d, J=3.3 Hz, 1H), 6.64–6.87 (m, 3H), 7.30 (m, 6H), 7.68 (m, 1H), 8.14 (m, 2H), 12.09 (br. S, 1H).

EXAMPLE 19

Synthesis of (3S)-3-(1,3-benzodioxol-5-yl)-3-({2-[3-methyl-6-oxo-5-(phenylmethyl)-1(6H)-pyridazinyl]hexanoyl}amino)propanoic acid.

Step One: To a mixture of dihydropyridazinone (2.50 g, 19.21 mmol) in EtOH (6 mL) at room temperature, benzaldehyde (2.04 g, 19.21 mmol) and solid KOH (1.3 g, 23.05 mmol) were added. This mixture was heated to 85° C. overnight, cooled to room temperature and poured into ice water. The resulting mixture was acidified to pH=4 with concentrated HCl and the precipitate was collected by filtration, washing with water. The resulting solid was then dried in vacuo to give 56 (3.6 g, 85%).

(3S)-3-(1,3-benzodioxol-5-yl)-3-({2-[3-methyl-6-oxo-5-(phenylmethyl)-1(6H)-pyridazinyl]hexanoyl}amino)propanoic acid was prepared from 56 according to procedures described in Examples 1 and 16. $^1$H NMR (400 MHz, CD$_3$SO$_2$CD$_3$): δ 0.80 (m, 3H), 1.18 (m, 4H), 1.95 (m, 2H), 2.18 (s, 3H), 2.65 (m, 2H), 3.79 (m, 2H), 5.06 (m, 1H), 5.26 (m, 1H), 5.97 (d, J=2.2 Hz, 2H), 6.81 (m, 3H), 6.98 (s, 1H), 7.27 (m, 5H), 8,27 (m, 1H), 12.14 (br. S, 1H).

EXAMPLE 20

Synthesis of (3S)-3-(1,3-benzodioxol-5-yl)-3-({2-[2-oxo-3-(phenylmethyl)-3,4-dihydro-1(2H)-quinazolinyl]hexanoyl}amino)propanoic acid.

Step 1: A solution of 2-nitrobenzylbromide (0.50 g, 2.31 mmol) and benzylamine (0.49 g, 4.62 mmol) in THF (5 mL) was stirred at room temperature overnight and was then diluted with EtOAc. The organic layer was washed with 1 N NaOH (twice) and brine, dried over MgSO$_4$ and filtered. The filtrate was concentrated under reduced pressure and the residue was purified by silica gel chromatography (hexanes:EtOAc, 3:1 increasing to 1:1) to give 57 (0.5 g, 89%) as an oil. (3S)-3-(1,3-benzodioxol-5-yl)-3-({2-[2-oxo-3-(phenylmethyl)-3,4-dihydro-1(2H)-quinazolinyl]hexanoyl}amino)propanoic acid was prepared with 57 according to procedures described in Examples 1 and 16. $^1$H NMR (400 MHz, CD$_3$SO$_2$CD$_3$): δ 0.78 (m, 3H), 1.21 (m, 4H), 1.88 (m, 1H), 2.14 (m, 1H), 2.65 (m, 2H), 4.26 (m, 2H), 4.43 (m, 1H), 4.80 (m, 1H), 5.03 (m, 1H), 5.18 (m, 1H), 5.92 (d, J=4.0 Hz, 1H), 5.97 (s, 1H), 6.70 (m, 2H), 6.80 (m, 1H), 6.95 (m, 2H), 7.12 (m, 2H), 7.30 (m, 5H), 8.20 (m, 1H), 12.09 (br. s, 1H).

EXAMPLE 21

Synthesis of (3S)-3-(1,3-benzodioxol-5-yl)-3-({2-[2-oxo-3-(phenylmethyl)-1(2H)-quinoxalinyl]hexanoyl}amino)propanoic acid.

Step One: To solution of 1,2-phenylenediamine (2.64 g, 14.4 mmol) and phenylpyruvic acid (2.00 g, 12.2 mmol) in ethanol (absolute, 20 mL), a solution of 2-mercaptoethanol (1.6 mL) in 2N HCl (18.3 mL) was added. The resulting mixture was heated to reflux for 2 hours, then was allowed to cool to room temperature and filtered, washing the precipitate with ethanol (twice). The precipitate was dried under vacuum to give 58 (1.88 g, 65%) as a white solid.

(3S)-3-(1,3-Benzodioxol-5-yl)-3-({2-[2-oxo-3-(phenylmethyl)-1(2H)-quinoxalinyl]hexanoyl}amino)propanoic acid was prepared from 58 according to procedures described in Examples 1 and 16. MS: Calculated (M−H)$^-$=540.21; Found (M−H)$^-$=540.21.

EXAMPLE 22

Synthesis of (3S)-3-(1,3-benzodioxol-5-yl-3-((2S)-2-(3-benzyl-5-methyl-2-oxo-1(2H)-pyridinyl)hexanoylamino) propanoic acid, (10).

Step One: To a solution of (R)-(+)-2-bromohexanoic acid (410 mg, 2.1 mmol) and NMM (0.265 mL, 2.1 mmol) in THF (8 mL) at 0° C. under a dry, nitrogen atmosphere, isobutyl chloroformate (0.27 mL, 2.1 mmol) was added. The resulting suspension was stirred at 0° C. for 10 minutes before the addition of a solution of 6 (500 mg, 2.1 mmol) in DMF (2 mL). After 1 hour the suspension was filtered and the filtrate was concentrated under reduced pressure. The residue was taken up in $CH_2Cl_2$ and washed with HCl (1 N, 2 times). The combined organic layers were washed with brine. The organic layer was dried over $MgSO_4$, filtered and concentrated under reduced pressure to give 59 (840 mg, 96% yield) as a yellow oil. This material was used without further purification.

Step Two: To a solution of 2-fluoro-5-methylpyridine (3.23 g, 30 mmol) in THF (60 mL) cooled to −78° C. under a dry, nitrogen atmosphere, lithium diisopropylamide (22 mL, 2 M solution in THF, 44 mmol) was added dropwise. The resulting orange-red solution was stirred at −78° C. for 6 hours after which benzaldehyde (3.1 mL, 35 mmol) was added. The reaction mixture was stirred an additional 30 minutes, quenched with $H_2O$ (75 mL) and extracted with EtOAc (2 times). The combined organic layers were washed with brine, dried over $MgSO_4$, filtered and concentrated under reduced pressure to give 60 (6.5 g, quant.) as a yellow oil. This material was used without further purification.

Step Three: A solution of 60 (6.5 g, 30 mmol), boron trifluoride diethyl etherate (13 mL, 100 mmol) and triethylsilane (9 mL, 60 mmol) in dichloroethane (50 mL) was heated to reflux under a dry, nitrogen atmosphere and for 1 hour. The resulting solution was allowed to cool to room temperature and quenched with $H_2O$ (50 mL). The resulting mixture was extracted with EtOAc (2 times). The combined organic layers were washed with brine, dried over $MgSO_4$, filtered and concentrated under reduced pressure to give 61 (5.9 g, 98% yield) as a yellow oil.

Step Four: A solution of 61 (5.9 g, 30 mmol) in dioxane (2 mL) was added to HCl (6 N, 50 mL) and the resulting mixture was heated to reflux for 12 hours. The resulting solution was allowed to cool to room temperature and made basic by the addition of NaOH (2 N). The resulting mixture was extracted with EtOAc (100 mL×2) and the combined organic layers were washed with brine, dried over $MgSO_4$ and filtered. The resulting filtrate was concentrated under reduced pressure. The residue was recrystallized from methanol/hexanes to provide 62 (3.1 g, 51% yield) as an off-white solid.

Step Five: To a solution of 62 (48 mg, 0.24 mmol) in DME (1.5 mL) under a dry, nitrogen atmosphere cooled to −40° C., NaHMDS (0.25 mL, 1M in THF, 0.25 mmol) was added. The resulting suspension was stirred at −40° C. for an additional 30 minutes before LiBr (21 mg, 0.25 mmol) was added. After an additional 10 minutes, a solution of 59 (100 mg, 0.24 mmol) in DMF (0.5 mL) was added dropwise. The resulting mixture was then allowed to warm to room temperature and then was heated to 45° C. for 3.5 hours. The mixture was allowed to cool to room temperature and quenched with HCl (1 N, 15 mL). The resulting mixture was extracted with $CH_2Cl_2$ (twice). The combined organic layers were washed with aqueous sodium carbonate (5%) and brine. The organic phase was dried over $MgSO_4$, filtered and concentrated under reduced pressure. The residue was recrystallized from methanol/hexanes to give 63 (39 mg, 31%) as white crystals. (3S)-3-(1,3-benzodioxol-5-yl-3-((2S)-2-(3-benzyl-5-methyl-2-oxo-1(2H)-pyridinyl) hexanoylamino)propanoic acid, (10),was prepared from 63 according to procedures described in Example 1.

Among the compounds representative of the present invention, which can be synthesized according to the procedure of Example 22, by varying starting materials, are (3S)-3-{[(2S)-2-(3-benzyl-5-methyl-2-oxopyridin-1(2H)-yl)hexanoyl]amino}-3-(3',4'-dimethoxy-1,1'-biphenyl-4-yl) propanoic acid, (3S)-3-({(2S)-2-[3-(2-chlorobenzyl)-5-methyl-2-oxopyridin-1(2H)-yl]hexanoyl}amino)-3-(3',4'-dimethoxy-1,1'-biphenyl-4-yl)propanoic acid, (3S)-3-(1,1'-biphenyl-4-yl)-3-({(2S)-2-[3-(2-chloro-6-methylbenzyl)-5-methyl-2-oxopyridin-1(2H)-yl]hexanoyl}amino)propanoic acid, (3S)-3-{[(2S)-2-(3-benzyl-5-methyl-2-oxopyridin-1 (2H)-yl)hexanoyl]amino}-3-(1,1'-biphenyl-4-yl)propanoic acid, (3S)-3-(1,1'-biphenyl-4-yl)-3-({(2S)-2-[3-(2-chlorobenzyl)-5-methyl-2-oxopyridin-1(2H)-yl] hexanoyl}amino)propanoic acid, (3S)-3-{[(2S)-2-(3-benzyl-5-methyl-2-oxopyridin-1(2H)-yl)hexanoyl]amino}-3-(4'-methyl-1,1'-biphenyl-4-yl)propanoic acid, (3S)-3-({(2S)-2-[3-(2-chlorobenzyl)-5-methyl-2-oxopyridin-1(2H)-yl]hexanoyl}amino)-3-(4'-methyl-1,1'-biphenyl-4-yl) propanoic acid, (3S)-3-({(2S)-2-[3-(2-chloro-6-methylbenzyl)-5-methyl-2-oxopyridin-1(2H)-yl] hexanoyl}amino)-3-(4'-methyl-1,1'-biphenyl-4-yl) propanoic acid, (3S)-3-{[(2S)-2-(3-benzyl-5-methyl-2-oxopyridin-1(2H)-yl)hexanoyl]amino -3-(2',6'-dimethoxy-1,1'-biphenyl-4-yl)propanoic acid, (3S)-3-({(2S)-2-[3-(2-chlorobenzyl)-5-methyl-2-oxopyridin-1(2H)-yl] hexanoyl}amino)-3-(2',6'-dimethoxy-1,1'-biphenyl-4-yl) propanoic acid, (3S)-3-({(2S)-2-[3-(2-chloro-6-methylbenzyl)-5-methyl-2-oxopyridin-1(2H)-yl] hexanoyl}amino)-3-(2',6'-dimethoxy-1,1'-biphenyl-4-yl) propanoic acid, (3S)-3-{[(2S)-2-(3-benzyl-5-methyl-2-oxopyridin-1(2H)-yl)hexanoyl]amino}-3-(1,1'-biphenyl-3-yl)propanoic acid, (3S)-3-(1,1'-biphenyl-3-yl)-3-({(2S)-2-[3-(2-chlorobenzyl)-5-methyl-2-oxopyridin-1(2H)-yl] hexanoyl}amino)propanoic acid, (3S)-3-(1,1'-biphenyl-3-yl)-3-({(2S)-2-[3-(2-chloro-6-methylbenzyl)-5-methyl-2-oxopyridin-1(2H)-yl]hexanoyl}amino)propanoic acid, (3S)-3-{[(2S)-2-(3-benzyl-5-methyl-2-oxopyridin-1(2H)-yl) hexanoyl]amino}-3-(2'-methoxy-1,1'-biphenyl-3-yl) propanoic acid, (3S)-3-({(2S)-2-[3-(2-chlorobenzyl)-5-methyl-2-oxopyridin-1(2H)-yl]hexanoyl}amino)-3-(2'-methoxy-1,1'-biphenyl-3-yl)propanoic acid, (3S)-3-({(2S)-2-[3-(2-chloro-6-methylbenzyl)-5-methyl-2-oxopyridin-1 (2H)-yl]hexanoyl}amino)-3-(2'-methoxy-1,1'-biphenyl-3-yl)propanoic acid, (3S)-3-({(2S)-2-[3-(2-fluoro-6-methoxybenzyl)-5-methyl-2-oxopyridin-1(2H)-yl] hexanoyl}amino)-3-(4-methylphenyl)propanoic acid, (3S)-3-({(2S)-2-[3-(2,6-dimethylbenzyl)-5-methyl-2-oxopyridin-1(2H)-yl]hexanoyl}amino)-3-(4-methylphenyl)propanoic acid, (3S)-3-({(2S)-2-[3-(3,5-dimethylbenzyl)-5-methyl-2-oxopyridin-1(2H)-yl]hexanoyl}amino)-3-(4-methylphenyl) propanoic acid, (3S)-3-({(2S)-2-[3-(2,6-dichlorobenzyl)-5-methyl-2-oxopyridin-1(2H)-yl]hexanoyl}amino)-3-(4-methylphenyl)propanoic acid, (3S)-3-({(2S)-2-[3-(2-chloro-6-fluorobenzyl)-5-methyl-2-oxopyridin-1(2H)-yl] hexanoyl}amino)-3-(4-methylphenyl)propanoic acid, (3S)-3-({(2S)-2-[3-(2,6-difluorobenzyl)-5-methyl-2-oxopyridin-1(2H)-yl]hexanoyl}amino)-3-(4-methylphenyl)propanoic acid, (3S)-3-(1,3-benzodioxol-5-yl)-3-({(2S)-2-[3-(2,6-difluorobenzyl)-5-methyl-2-oxopyridin-1(2H)-yl] hexanoyl}amino)propanoic acid, (3S)-3-(1,3-benzodioxol-5-yl)-3-({(2S)-2-[3-(2-chloro-6-fluorobenzyl)-5-methyl-2-oxopyridin-1(2H)-yl]hexanoyl}amino)propanoic acid, (3S)-3-(1,3-benzodioxol-5-yl)-3-({(2S)-2-[3-(2,6-dichlorobenzyl)-5-methyl-2-oxopyridin-1(2H)-yl] hexanoyl}amino)propanoic acid, (3S)-3-(1,3-benzodioxol-5-yl)-3-({(2S)-2-[3-(2,6-dimethylbenzyl)-5-methyl-2-oxopyridin-1(2H)-yl]hexanoyl}amino)propanoic acid, (3S)-3-(1,3-benzodioxol-5-yl)-3-({(2S)-2-[3-(3,5- dimethylbenzyl)-5-methyl-2-oxopyridin-1(2H)-yl]hexanoyl}amino)propanoic acid, (3S)-3-(1,3-benzodioxol-5-yl)-3-({(2S)-2-[3-(2-fluoro-6-methoxybenzyl)-5-methyl-2-oxopyridin-1(2H)-yl]hexanoyl}amino)propanoic acid, (3S)-3-({ (2S)-2-[3-(2-chlorobenzyl)-5-methyl-2-oxopyridin-1(2H)-yl]hexanoyl}amino)-3-(3,4-diethoxyphenyl)propanoic acid, (3S)-3-(3,4-diethoxyphenyl)-3-({(2S)-2-[3-(2,6-difluorobenzyl)-5-methyl-2-oxopyridin-1(2H)-yl]hexanoyl}amino)propanoic acid, (3S)-3-({(2S)-2-[3-(2,6-difluorobenzyl)-5-methyl-2-oxopyridin-1(2H)-yl]hexanoyl}amino)-3-(3-ethoxyphenyl)propanoic acid, (3S)-3-({(2S)-2-[3-(2-chloro-6-fluorobenzyl)-5-methyl-2-oxopyridin-1(2H)-yl]hexanoyl}amino)-3-(3-ethoxyphenyl)propanoic acid(3S)-3-({(2S)-2-[3-(2-chlorobenzyl)-5-methyl-2-oxopyridin-1(2H)-yl]-3-methylbutanoyl}amino)-3-(4-methylphenyl)propanoic acid, (3S)-3-({(2S)-2-[3-(2-chlorobenzyl)-5-methyl-2-oxopyridin-1(2H)-yl]-4-methylpentanoyl}amino)-3-(4-methylphenyl)propanoic acid, (3S)-3-(1,3-benzodioxol-5-yl)-3-({(2S)-2-[3-(2-chlorobenzyl)-5-methyl-2-oxopyridin-1(2H)-yl]-4-methylpentanoyl}amino)propanoic acid, (3S)-3-(1,3-benzodioxol-5-yl)-3-({(2S)-2-[3-(2-chlorobenzyl)-5-methyl-2-oxopyridin-1(2H)-yl]-3-methylbutanoyl}amino)propanoic acid, (3S)-3-(1,3-benzodioxol-5-yl)-3-({(2S)-2-[3-(2-chlorobenzyl)-5-methyl-2-oxopyridin-1(2H)-yl]-3-phenylpropanoyl}amino)propanoic acid, (3S)-3-(1,3-benzodioxol-5-yl)-3-(((2R)-2-(1-benzyl-5-methyl-2-oxo-1,2-dihydropyridin-3-yl)hexanoyl)amino) propanoic acid and (3S)-3-({(2S)-2-[3-(2-chlorobenzyl)-5-methyl-2-oxopyridin-1(2H)-yl]-3-phenylpropanoyl}amino)-3-(4-methylphenyl)propanoic acid.

EXAMPLE 23

Synthesis of (3S)-3-(1,3-benzodioxol-5-yl)-3-{[(2R)-2-(3-benzyl-4-hydroxy-5-methyl-2-oxopyridin-1(2H)-yl)hexanoyl]amino}propanoic acid, 67, and (3S)-3-(1,3-benzodioxol-5-yl)-3-{[(2S)-2-(3-benzyl-4-hydroxy-5-methyl-2-oxopyridin-1(2H)-yl)hexanoyl]amino}propanoic acid, 68.

Step One: To a solution of methyl propionylacetate (2.00 g 15.4 mmol) in anhydrous THF (62 mL) cooled to 0° C. under a dry nitrogen atmosphere, sodium hydride (60% dispersion in mineral oil, 0.644 g, 16.1 mmol) was added in two portions. The resulting mixture was stirred for 15 minutes at 0° C., benzyl bromide (2.75 g, 16.1 mmol) was added by syringe then the mixture was allowed to warm to room temperature overnight. The resulting mixture was poured into HCl (2N) and extracted with ethyl acetate. The organic layer was washed with brine, dried over Mg SO$_4$ and filtered and the filtrate was concentrated under reduced pressure. The residue was purified by silica gel chromatography, eluting with 9:1 hexanes:ethyl acetate to give 64 (2.86 g, 84% yield).

Step Two: To a suspension of sodium hydride (60% dispersion in mineral oil, 0.623 g, 15.6 mmol) in THF (52 mL) at room temperature under a dry nitrogen atmosphere, N,N,N',N'-tetramethylethylenediamine (2.10 mL, 13.6 mmol) was added. The resulting suspension was cooled to −20° C. and a solution of 64 (2.86 g, 13.0 mmol) in THF (5 mL) was added slowly. The mixture was allowed to warm to room temperature, stirred for 10 minutes then was cooled to −20° C. To the resulting solution, n-butyllithium (1.6M in hexanes, 15.4 mL, 24.9 mmol) was added dropwise by syringe. The mixture was stirred at −20° C. for an additional 15 minutes, then quenched with the rapid addition of methyl formate (1.00 mL, 16.2 mmol) via syringe and the mixture was allowed to stir for an additional 15 minutes. The reaction was cautiously quenched with excess aqueous HCl (2N) and diluted with hexanes. The hexanes layer is washed with brine, dried over MgSO$_4$, filtered and concentrated under reduced pressure to give 65 (1.10 g, 34%) as a yellow oil. This material was used without further purification.

Step Three: A solution of 65 (0.75 g, 3.0 mmol) and 23 (0.75 g, 2.1 mmol) in methanol (30 mL, 0.1M) was heated at 45° C. under nitrogen for 1 hour before refluxing overnight. The mixture was cooled and concentrated to dryness. The residue was purified by silica gel chromatography, eluting with 2:1 hexanes/ethyl acetate, increasing to ethyl acetate to give 66 (0.40 g, 35% yield) as a white foam.

Step Four: To a solution of 66 (0.40 g, 0.73 mmol) in THF (3 mL) at room temperature, aqueous NaOH (1 mL) and methanol (2 mL) were added. The resulting solution was stirred for 15 minutes, diluted with water and extracted with ethyl ether. The aqueous layer was acidified with HCl (2N) and extracted with ethyl acetate. The ethyl acetate layer was washed with water and brine, dried over MgSO$_4$ and filtered. The filtrate was concentrated under reduced pressure and the residue was purified by reverse phase HPLC (A: 19:1 H2O:CH$^3$CN+0.1% TFA; B:19:1 CH$^3$CN:H2O+0.1% TFA; gradient elution 30% B to 100% B in 31 minutes; 254 nM). The fractions containing each of the diastereomers were separately diluted with water and extracted with ethyl acetate. The ethyl acetate layers were separately washed with water (3 times) and brine, dried over MgSO$_4$ and filtered and the filtrates were separately concentrated under reduced pressure to give (3S)-3-(1,3-benzodioxol-5-yl)-3-{[(2R)-2-(3-benzyl-4-hydroxy-5-methyl-2-oxopyridin-1(2H)-yl)hexanoyl]amino}propanoic acid, 67, (18 mg, 5% yield) and (3S)-3-(1,3-benzodioxol-5-yl)-3-{[(2S)-2-(3-benzyl-4-hydroxy-5-methyl-2-oxopyridin-1(2H)-yl)hexanoyl]amino}propanoic acid, 68, (105 mg, 28% yield). MS for 67: Calculated (M+H)$^+$=521.23; Found (M+H)$^+$=520.97. MS for 68: Calculated (M+H)$^+$=521.23; Found (M+H)$^+$=520.95.

EXAMPLE 24

Synthesis of (3S)-3-(3-isopropoxyphenyl)-3-({2-[2-oxo-4-(2-phenylethyl)pyridin-1(2H)-yl]hexanoyl}amino)propanoic acid.

Step One: To a solution of diisopropylamine (2.94 g, 29.1 mmol) in THF (20 mL) cooled to −78° C. under a dry nitrogen atmosphere, butyllithium (12.8 mL of a 2.5 M solution in hexanes, 32.0 mmol) was added by syringe and stirred at −78° C. for 15 minutes. The solution was added by cannula to a solution of 2-fluoro-4-methyl-pyridine (2.15 g, 9.40 mmol) in THF (20 mL) cooled to −78° C. under a dry nitrogen atmosphere. The resulting mixture was stirred at −78° C. for 4 hours, and then quenched with benzaldehyde (2.17 mL, 21.3 mmol). The resulting yellow solution was warmed to room temperature, diluted with water and extracted with ethyl acetate. The organic layer was washed with brine, dried over MgSO$_4$ and filtered. The filtrate was concentrated under reduced pressure and the residue was purified by silica gel chromatography, eluting with 7:3 hexanes:ethyl acetate to give 69 (1.92 g, 94%) as a yellow oil.

Step Two: To a solution of 69 (1.92 g, 8.84 mmol) in anhydrous methanol (20 mL) at room temperature under a dry nitrogen atmosphere, palladium on charcoal (1.00 g, 10% Pd dry weight basis, Degussa type E101 NE/W, wet, 50% water by weight) and four drops of glacial acetic acid were added. The nitrogen atmosphere was replaced by hydrogen (alternate five times between vacuum and hydrogen supplied by balloon) and the mixture was stirred at room temperature overnight. The mixture was filtered through Celite® 521 and the filtrate was concentrated under reduced pressure. The residue was purified by silica gel chromatography, eluting with 8:2 hexanes:ethyl acetate to give 70 (0.98 g, 55%) as a white solid.

Step Three: To a solution of 70 (0.90 g, 4.47 mmol) in hydrogen chloride (2 mL, 4.0 M in dioxane, 8.0 mmol) at room temperature, aqueous hydrogen chloride (6.0 M, 40 mL) was added and the mixture was refluxed for 3 hours. The solution was cooled to room temperature, made basic with aqueous sodium hydroxide (2N), and extracted with ethyl acetate. The organic layer was washed with brine, dried over $MgSO_4$ and filtered. The filtrate was concentrated under reduced pressure to give 71 (0.81 g, 91%) as a pale yellow solid. This material was used without purification Step Four: To a solution of 71 (0.20 g, 1.0 mmol) in methyl sulfoxide (4.0 mL) at room temperature, sodium hydride (60% w/w dispersion in mineral oil, 0.12 g, 3.0 mmol) was added. The mixture was stirred at room temperature under a dry nitrogen atmosphere for 1 hour. To the resulting mixture, ethyl 2-bromohexanoate (0.18 mL, 1.0 mmol) was added and the mixture was stirred for 30 minutes. The mixture was quenched with HCl (2N, 50 mL) and extracted with ethyl acetate. The organic layer was washed with brine, dried over $MgSO_4$ and filtered. The filtrate was concentrated under reduced pressure and the residue was purified by silica gel chromatography, eluting with 9:1 hexanes:ethyl acetate, increasing to 8:2 hexanes:ethyl acetate to give 72 (0.19 g, 0.55 mmol) as a solid.

(3S)-3-(3-isopropoxyphenyl)-3-({2-[2-oxo-4-(2-phenylethyl)pyridin-1(2H)-yl]hexanoyl}amino)propanoic acid was prepared from 72 according to procedures described in Example 1. MS: Calculated $(M-H)^-=517.27$; Found $(M-H)^-=517.21$.

EXAMPLE 25

Synthesis of (3S)-3-[3-(difluoromethyl)phenyl]-3-({2-[5-methyl-2-oxo-3-(phenylmethyl)-1(2H)-pyridinyl]hexanoyl}amino)propanoic acid.

Step One: To a solution of 3-bromobenzaldehyde, 73, (3.00 g, 16.2 mmol) in DMF (69 mL) under a dry nitrogen atmosphere, palladium acetate (73 mg, 0.32 mmol), tri-o-tolylphosphine (197 mg, 0.65 mmol), ethyl acrylate (2.20 mL, 20.3 mmol) and triethylamine (4.50 mL, 32.4 mmol) were added. The system was deoxygenated (toggle between vacuum and nitrogen five times), the mixture was heated to 125° C. for 19 hours and then cooled to room temperature. The reaction was poured into water and extracted with ether. The organic layer was washed with HCl (4N) and brine, dried over $MgSO_4$ and filtered. The filtrate was concentrated under reduced pressure to give 74 (2.74 g, 83%), which was used without further purification.

Step Two: To a flask containing 74 (1.00 g, 4.9 mmol) under a dry nitrogen atmosphere, (dimethylamino)sulfur trifluoride (0.96 mL, 9.8 mmol) was added by syringe. The mixture was heated to 90° C. behind a blast shield for 25 minutes then was cooled to room temperature. The resulting mixture was diluted with $CH_2Cl_2$ and washed with saturated aqueous $NaHCO_3$ and $H_2O$. The organic layer was dried over $MgSO_4$ and filtered and the filtrate was concentrated under reduced pressure. The residue was purified by silica gel chromatography, eluting with 1:5 ethyl acetate:hexanes to give 75 (0.62 g, 56%).

Step Three: To a solution of (R)-(+)-N-benzyl-α-methylbenzylamine (0.70 g, 3.3 mmol) in THF (6.7 mL) cooled to −78° C. under a dry nitrogen atmosphere, sec-BuLi (4.22 mL, 1.3M in cyclohexane, 5.5 mmol) was added dropwise. The resulting mixture was stirred at −78° C. for 30 minutes and then a solution of 75 (0.62 g, 2.74 mmol) in THF (3.4 mL) was added dropwise by syringe. The mixture was stirred at −78° C. for 5 hours and then quenched with glacial AcOH (2 mL) in THF (5 mL). The reaction mixture was warmed to room temperature, poured into a 1:1 mixture of saturated aqueous $NaHCO_3$:EtOAc. The organic layer was washed with $H_2O$ (2 times) and brine, dried over $MgSO_4$ and filtered. The filtrate was concentrated under reduced pressure and the residue was purified by silica gel chromatography, eluting with 1:5 ethyl actetate:hexanes to give 76 (1.2 g, 100%). This material still contained minor impurities but was used without further purification.

Step Four: To a solution of 76 (0.50 g, 1.14 mmol) in EtOH (10 mL) at room temperature under a dry nitrogen atmosphere, Pd/C (10% Pd dry weight basis, 50% water by weight, Degussa type E101 NE/W, 0.25 g) and glacial AcOH (0.5 mL) were added. The atmosphere was replaced by hydrogen (toggle between vacuum and hydrogen from a balloon five times) and the mixture was heated to 35° C. for 6 hours. The reaction was cooled to room temperature, filtered through a plug of Celite $\bar{U}$ 521 and the filtrate was concentrated under reduced pressure. The residue was diluted with $CHCl_3$ and washed with saturated aqueous $NaHCO_3$. The aqueous layer was extracted with $CHCl_3$ (2 times) and the combined organic layers were dried over $MgSO_4$ and filtered. The filtrate was concentrated under reduced pressure and the residue was purified by silica gel chromatography, eluting with 1:10 $MeOH:CHCl_3$ to give 77 (180 mg, 67%). (03S)-3-[3-(difluoromethyl)phenyl]-3-({2-[5-methyl-2-oxo-3-(phenylmethyl)-1(2H)-pyridinyl]hexanoyl}amino)propanoic acid was synthesized from 77 according to procedures described in Example 1. MS: Calculated $(M-H)^-=509.23$; Found $(M-H)^-=509.19$.

EXAMPLE 26

The ability of compounds of the present invention to inhibit binding is determined by a procedure in which a 26-amino acid peptide containing the CS1 sequence of fibronectin with an N-terminal Cys (CDELPQLVTLPHPNLHGPEILDVPST) was coupled to maleimide activated ovalbumin. Bovine serum albumin (BSA) and CS1 conjugated ovalbumin were coated onto 96-well polystyrene plates at 0.5 mg/ml in TBS (50 mM Tris, pH 7.5; 150 mM NaCl) at 4° C. for 16 hours. The plates were washed three times with TBS and blocked with TBS containing 3% BSA at room temperature for 4 hours. Blocked plates were washed three times in binding buffer (TBS; 1 mM $MgCl_2$; 1 mM $CaCl_2$; 1 mM $MnCl_2$) prior to assay. Ramos cells fluorescently labeled with calcein AM were resuspended in binding buffer ($10^7$ cells/ml) and diluted 1:2 with same buffer with or without compound. The cells were added immediately to the wells (2.5×105 cells/well) and incubated for 30 minutes at 37° C. Following three washes with binding buffer, adherent cells were lysed and quantitated using a fluorometer. The results are shown in Tables 1, 2, 3 and 4. $IC_{50}$ is defined as the dose required to give 50% inhibition. MS in Table 3 stands for Mass Spec. nd stands for not determined in the Tables. A stands for inhibition in Table 2, and the percent inhibition indicates the inhibition of cell adhesion when compound is included in the assay at a concentration of 100 μM. The lower the $IC_{50}$ value and the greater the percentage of inhibition, the more efficient the compound is at prevention of cell adhesion.

TABLE 1

| Compound Number | IC$_{50}$ (nM) | Mass Spectral Data (m/z) |
|---|---|---|
| 8 | 7 | Calc'd (M − H)$^-$ = 503.22 |
| | | Found (M − H)$^-$ = 503.24 |
| 9 | 2000 | Calc'd (M − H)$^-$ = 503.22 |
| | | Found (M − H)$^-$ = 503.24 |
| 10 | 3 | Calc'd (M − H)$^-$ = 503.22 |
| | | Found (M − H)$^-$ = 503.22 |
| 12 | 40 | Calc'd (M − H)$^-$ = 501.24 |
| | | Found (M − H)$^-$ = 501.27 |
| 13 | 70 | Calc'd (M − H)$^-$ = 473.24 |
| | | Found (M − H)$^-$ = 473.26 |
| 14 | 150 | Calc'd (M − H)$^-$ = 477.22 |
| | | Found (M − H)$^-$ = 477.25 |
| 15 | 30 | Calc'd (M + H)$^+$ = 535.25 |
| | | Found (M + H)$^+$ = 535.00 |
| 16 | 35 | Calc'd (M + H)$^+$ = 519.25 |
| | | Found (M + H)$^+$ = 519.18 |
| 17 | 60 | Calc'd (M − H)$^-$ = 521.21 |
| | | Found (M − H)$^-$ = 521.22 |
| 19 | 6 | Calc'd (M − H)$^-$ = 537.18 |
| | | Found (M − H)$^-$ = 537.22 |

TABLE 2

| Compound | IC$_{50}$ ($\mu$M) | % A | Mass Spectral Data (m/z) |
|---|---|---|---|
| (3S)-3-(1,3-benzodioxol-5-yl)-3-({(2S)-2-[2-oxo-3-(2-thienylmethyl)-1-imidazolidinyl]hexanoyl}amino)propanoic acid | 0.15 | 100 | Calc'd (M − H)$^-$ = 486.37 Found (M − H)$^-$ = 486.20 |
| (3S)-3-(1,3-benzodioxol-5-yl)-3-(((2S)-2-(2-oxo-3-(2-thienylmethyl)tetrahydro-1(2H)-pyrimidinyl)hexanoyl)amino)propanoic acid | 0.005 | 100 | Calc'd (M − H)$^-$ = 500.18 Found (M − H)$^-$ = 500.22 |
| (3S)-3-(1,3-benzodioxol-5-yl)-3-(((2S)-2-(2-oxo-4-(2-thienyl)-3-(2-thienylmethyl)tetrahydro-1(2H)-pyrimidinyl)hexanoyl)amino)propanoic acid | 0.05 | 100 | Calc'd (M − H)$^-$ = 582.17 Found (M − H)$^-$ = 582.21 |
| (3S)-3-(1,3-benzodioxol-5-yl)-3-({(2S)-2-[2-oxo-3-(2-thienylmethyl)-1,3-diazepan-1-yl]hexanoyl}amino)propanoic acid | nd | nd | nd |

TABLE 3

| Compound | Mass Spectral Data (m/z) | IC$_{50}$ ($\mu$M) |
|---|---|---|
| (3S)-3-(1,3-benzodioxol-5-yl)-3-({(2S)-2-[2,5-dioxo-1-(2-thiophenylmethyl)-1,2,3,5-tetrahydro-4H-1,4-benzodiazepin-4-yl]hexanoyl}amino)propanoic acid | Calc'd (M − H)$^-$ = 576.18 Found (M − H)$^-$ = 576.18 | 1.5 |
| (3S)-3-(1,3-benzodioxol-5-yl)-3-({(2S)-2-[(3S)-2,5-dioxo-(phenylmethyl)-4-(2-thiophenylmethyl)tetrahydro-1(2H)-pyrazinyl]hexanoyl}amino)propanoic acid | Calc'd (M − H)$^-$ = 604.21 Found (M − H)$^-$ = 604.24 | 6 |
| (3S)-3-(1,3-benzodioxol-5-yl)-3-({2-[3-(phenyloxy)phenyl]acetyl}amino)propanoic acid | Calc'd (M − H)$^-$ = 418.11 Found (M − H)$^-$ = 418.12 | >100 |
| (3S)-3-(1,3-benzodioxol-5-yl)-3-({2-[2-oxo-3-[(2-thiophenylmethyl)amino]-1(2H)-pyridinyl]hexanoyl}amino)propanoic acid | Calc'd (M − H)$^-$ = 510.17 Found (M − H)$^-$ = 510.21 | 1.3 |
| (3S)-3-(1,3-benzodioxol-5-yl)-3-({2-[2-oxo-3-(phenylmethyl)-2,3-dihydro-1H-benzimidazol-1-yl]acetyl}amino)propanoic acid | Calc'd (M − H)$^-$ = 472.15 Found (M − H)$^-$ = 472.18 | 0.2 |
| (3S)-3-(1,3-benzodioxol-5-yl)-3-({2-[2-oxo-3-(phenylmethyl)-2,3-dihydro-1H-benzimidazol-1-yl]hexanoyl}amino)propanoic acid | Calc'd (M − H)$^-$ = 528.21 Found (M − H)$^-$ = 528.22 | 0.07 |
| (3S)-3-(1,3-benzodioxol-5-yl)-3-({2-[2-oxo-3-(phenylcarbonyl)-1(2H)-pyridinyl]butanoyl}amino)propanoic acid | Calc'd (M − H)$^-$ = 461.17 Found (M − H)$^-$ = 461.18 | 0.03 |
| (3S)-3-(1,3-benzodioxol-5-yl)-3-({(2S)-2-[2-oxo-3-(phenylcarbonyl)-1(2H)-pyridinyl]hexanoyl}amino)propanoic acid | Calc'd (M − H)$^-$ = 503.18 Found (M − H)$^-$ = 503.18 | 0.55 |
| (3S)-3-(1,3-benzodioxol-5-yl)-3-({2-[2-oxo-3-(phenylmethyl)-1(2H)-pyridinyl]acetyl}amino)propanoic acid | Calc'd (M − H)$^-$ = 433.14 Found (M − H)$^-$ = 433.16 | 0.45 |
| (3S)-3-(1,3-benzodioxol-5-yl)-3-[({1-[2-oxo-3-(phenylmethyl)-1(2H)-pyridinyl]cyclohexyl}carbonyl)amino]proparioic acid | Calc'd (M − H)$^-$ = 501.20 Found (M − H)$^-$ = 501.24 | 50 |
| (3S)-3-(1,3-benzodioxol-5-yl)-3-({(2S)-2-[2-oxo-3-(phenylmethyl)-1(2H)-pyridinyl]hexanoyl}amino)propanoic acid | Calc'd (M − H)$^-$ = 489.20 Found (M − H)$^-$ = 489.20 | 0.004 |
| (3S)-3-(1,3-benzodioxol-5-yl)-3-({2-[2-oxo-3-(phenylmethyl)-2,3-dihydro-1H-imidazol-1-yl]hexanoyl}amino)propanoic acid | Calc'd (M − H)$^-$ = 478.20 Found (M − H)$^-$ = 478.23 | 0.06 |
| (3S)-3-(1,3-benzodioxol-5-yl)-3-({(2S)-2-[2,4-dioxo-1-(phenylmethyl)-1,4-dihydro-3(2H)-quinazolinyl]hexanoyl}amino)propanoic acid | Calc'd (M − H)$^-$ = 556.21 Found (M − H)$^-$ = 556.22 | 0.1 |
| (3S)-3-(1,3-benzodioxol-5-yl)-3-({2-[3-[(2-chlorophenyl)methyl]-5-methyl-2-oxo-1(2H)-pyridinyl]hexanoyl}amino)propanoic acid | Calc'd (M − H)$^-$ = 537.18 Found (M − H)$^-$ = 537.22 | 0.01 |
| (3S)-3-(1,3-benzodioxol-5-yl)-3-({2-[5,5-dimethyl-2,4-dioxo-3-(phenylmethyl)tetrahydro-1H-imidazol-1-yl]hexanoyl}amino)propanoic acid | Calc'd (M − H)$^-$ = 522.22 Found (M − H)$^-$ = 522.22 | 20 |
| (3S)-3-(1,3-benzodioxol-5-yl)-3-({2-[2-oxo-5-(phenylmethyl)-1(2H)-pyridinyl]hexanoyl}amino)propanoic acid | Calc'd (M − H)$^-$ = 489.20 Found (M − H)$^-$ = 489.21 | 0.04 |
| (3S)-3-(1,3-benzodioxol-5-yl)-3-({2-[2-oxo-3-(phenylmethyl)-1(2H)-quinoxalinyl]hexanoyl}amino)propanoic acid | Calc'd (M − H)$^-$ = 540.21 Found (M − H)$^-$ = 540.21 | 100 |
| (3S)-3-(1,3-benzodioxol-5-yl)-3-({2-[2-oxo-3-(phenylmethyl)-1(2H)-pyridinyl]pentanoyl}amino)propanoic acid | Calc'd (M − H)$^-$ = 475.18 Found (M − H)$^-$ = 475.19 | 0.06 |
| (3S)-3-(1,3-benzodioxol-5-yl)-3-({2-[3-methyl-6-oxo-5-(phenylmethyl)-1(6H)-pyridazinyl]hexanoyl}amino)propanoic acid | Calc'd (M − H)$^-$ = 504.21 Found (M − H)$^-$ = 504.24 | 0.06 |
| (3S)-3-(1,3-benzodioxol-5-yl)-3-({2-[2-oxo-3-(phenylmethyl)-3,4-dihydro-1(2H)-quinazolinyl]hexanoyl}amino)propanoic acid | Calc'd (M − H)$^-$ = 542.23 Found (M − H)$^-$ = 542.26 | 0.4 |
| (3S)-3-(1,3-benzodioxol-5-yl)-3-({2-[2-oxo-3-(phenylmethyl)-1(2H)-quinolinyl]hexanoyl}amino)propanoic acid | Calc'd (M − H)$^-$ = 539.22 Found (M − H)$^-$ = 539.22 | 2 |

TABLE 4

| Compound | IC$_{50}$ (nM) | Mass Spectral Data (m/z) |
|---|---|---|
| (3S)-3-{[(2S)-2-(3-benzyl-5-methyl-2-oxopyridin-1(2H)-yl)hexanoyl]amino}-3-(3,5-dimethoxyphenyl)propanoic acid | 10 | Measured (M − H)$^-$ = 519.25; Calculated (M − H)$^-$ = 519.25. |

TABLE 4-continued

| Compound | IC$_{50}$ (nM) | Mass Spectral Data (m/z) |
|---|---|---|
| (3S)-3-{[(2S)-2-(3-benzyl-5-methyl-2-oxopyridin-1(2H)-yl)hexanoyl]amino}-3-(3-fluoro-4-methoxyphenyl)propanoic acid | 17 | Measured (M − H)⁻ = 507.13; Calculated (M − H)⁻ = 507.23. |
| (3S)-3-(1,3-benzodioxol-5-yl)-3-{[2-(3-benzyl-2-oxopyridin-1(2H)-yl)hexanoyl]amino}propanoic acid | 30 | Measured (M − H)⁻ = 489.17; Calculated (M − H)⁻ = 489.20. |
| (3S)-3-{[2-(3-benzyl-5-methyl-2-oxopyridin-1(2H)-yl)hexanoyl]amino}-3-(3-propoxyphenyl)propanoic acid | 10 | Measured (M − H)⁻ = 517.19; Calculated (M − H)⁻ = 517.27. |
| (3S)-3-{[2-(3-benzyl-2-oxopyridin-1(2H)-yl)hexanoyl]amino}-3-(4-methoxy-2,3-dimethylphenyl)propanoic acid | 300 | Measured (M + H)⁺ = 504.94; Calculated (M + H)⁺ = 505.27. |
| (3S)-3-{[(2S)-2-(3-benzyl-5-methyl-2-oxopyridin-1(2H)-yl)hexanoyl]amino}-3-(2',6'-dimethoxy-1,1'-biphenyl-4-yl)propanoic acid | 200 | Measured (M − H)⁻ = 595.18; Calculated (M − H)⁻ = 595.28. |
| (3S)-3-{[2-(3-benzyl-5-methyl-2-oxopyridin-1(2H)-yl)hexanoyl]amino}-3-(3,4-dimethylphenyl)propanoic acid | 130 | Measured (M − H)⁻ = 487.24; Calculated (M − H)⁻ = 487.26. |
| (3S)-3-{[2-(3-benzyl-5-methyl-2-oxopyridin-1(2H)-yl)hexanoyl]amino}-3-(3-ethoxyphenyl)propanoic acid | 35 | Measured (M + H)⁺ = 504.99; Calculated (M + H)⁺ = 505.27. |
| (3S)-3-{[2-(3-benzyl-5-methyl-2-oxopyridin-1(2H)-yl)hexanoyl]amino}-3-(3,4,5-trimethoxyphenyl)propanoic acid | 33 | Measured (M − H)⁻ = 550.93; Calculated (M + H)⁺ = 551.28. |
| (3S)-3-{[2-(3-benzyl-5-methyl-2-oxopyridin-1(2H)-yl)hexanoyl]amino}-3-(4-methoxy-3,5-dimethylphenyl)propanoic acid | 140 | Measured (M + H)⁺ = 518.98; Calculated (M + H)⁺ = 519.29. |
| (3S)-3-{[2-(3-benzyl-5-methyl-2-oxopyridin-1(2H)-yl)hexanoyl]amino}-3-(6-methoxy-2-naphthyl)propanoic acid | 40 | Measured (M + H)⁺ = 540.98; Calculated (M + H)⁺ = 541.27. 541.27. |
| (3S)-3-{[2-(3-benzyl-5-methyl-2-oxopyridin-1(2H)-yl)hexanoyl]amino}-3-(3-butoxyphenyl)propanoic acid | 45 | Measured (M + H)⁺ = 533.03; Calculated (M + H)⁺ = 533.30. |
| (3S)-3-(1,3-benzodioxol-5-yl)-3-{[(2S)-2-(3-benzyl-4-hydroxy-5-methyl-2-oxopyridin-1(2H)-yl)hexanoyl]amino}propanoic acid | 200 | Measured (M + H)⁺ = 520.97; Calculated (M + H)⁺ = 521.23. |
| (3S)-3-(1,3-benzodioxol-5-yl)-3-{[(2R)-2-(3-benzyl-4-hydroxy-5-methyl-2-oxopyridin-1(2H)-yl)hexanoyl]amino}propanoic acid | 2000 | Measured (M + H)⁺ = 520.95; Calculated (M + H)⁺ = = 521.23. |
| (3S)-3-{[2-(3-benzyl-5-methyl-2-oxopyridin-1(2H)-yl)hexanoyl]amino}-3-(3-isopropoxyphenyl)propanoic acid | 4 | Measured (M + H)⁺ = 518.99; Calculated (M + H)⁺ = 519.29. |
| (3S)-3-({2-[3-(2,6-dichlorobenzyl)-5-methyl-2-oxopyridin-1(2H)-yl]hexanoyl}amino)-3-(3-isopropoxyphenyl)propanoic acid | 275 | Calculated (M + H)⁺ = 587.21; Found (M + H)⁺ = 586.95. |
| (3S)-3-(3-isopropoxyphenyl)-3-({2-[2-oxo-4-(2-phenylethyl)pyridin-1(2H)-yl]hexanoyl}amino)propanoic acid | 95 | Calculated (M − H)⁻ = 517.27; Found (M − H)⁻ = 517.21. |
| (3S)-3-{[2-(3-benzyl-5-methyl-2-oxopyridin-1(2H)-yl)hexanoyl]amino}-3-(3,5-dimethylphenyl)propanoic acid | 52 | Calculated (M − H)⁻ = 487.26; Found (M − H)⁻ = 487.20. |
| (3S)-3-{[2-(3-benzyl-5-methyl-2-oxopyridin-1(2H)-yl)hexandyl]amino}-3-(4-methoxy-2,5-dimethylphenyl)propanoic acid | 283 | Calculated (M − H)⁻ = 517.27; Found (M − H)⁻ = 517.20. |
| (3S)-3-({2-[3-(3-chlorobenzyl)-5-methyl-2-oxopyridin-1(2H)-yl]hexanoyl}amino)-3-(3-propoxyphenyl)propanoic acid | 23 | Calculated (M − H)⁻ = 551.23; Found (M − H)⁻ = 551.22. |
| (3S)-3-{[2-(3-benzyl-5-methyl-2-oxopyridin-1(2H)-yl)hexanoyl]amino}-3-[3-(trifluoromethyl)phenyl]propanoic acid | 250 | Calculated (M + H)⁺ = 529.23; Found (M + H)⁺ = 529.01. |
| (3S)-3-{[2-(3-benzyl-5-methyl-2-oxopyridin-1(2H)-yl)hexanoyl]amino}-3-[4-(trifluoromethoxy)phenyl]propanoic acid | 27 | Calculated (M + H)⁺ = 545.23; Found (M + H)⁺ = 544.97. |
| (3S)-3-({2-[3-(3-chlorobenzyl)-5-methyl-2-oxopyridin-1(2H)-yl]hexanoyl}amino)-3-(3-isopropoxypheyl)propanoic acid | 20 | Calculated (M + H)⁺ = 553.25; Found (M + H)⁺ = 552.95. |
| (3S)-3-({2-[3-(2-ethoxybenzyl)-5-methyl-2-oxopyridin-1(2H)-yl]hexanoyl}amino)-3-(3-isopropoxyphenyl)propanoic acid | 19 | Calculated (M + H)⁺ = 563.31; Found (M + H)⁺ = 563.17. |
| (3S)-3-(3-isopropoxyphenyl)-3-({2-[3-(2-methoxybenzyl)-5-methyl-2-oxopyridin-1(2H)-yl]hexanoyl}amino)propanoic acid | 4 | Calculated (M + H)⁺ = 549.30; Found (M + H)⁺ = 549.13. |
| (3S)-3-{[2-(3-benzyl-5-methyl-2-oxopyridin-1(2H)-yl)hexanoyl]amino}-3-[3-(trifluoromethoxy)phenyl]propanoic acid | 40 | Calculated (M − H)⁻ = 543.21; Found (M − H)⁻ = 543.16. |
| (3S)-3-{[2-(3-benzyl-5-methyl-2-oxopyridin-1(2H)-yl)hexanoyl]amino}-3-(3-ethoxy-4-methoxyphenyl)propanoic acid | 4 | Calculated (M − H)⁻ = 533.27; Found (M − H)⁻ = 533.22. |
| (3S)-3-{[2-(3-benzyl-5-methyl-2-oxopyridin-1(2H)-yl)hexanoyl]amino}-3-(4'-methyl-1,1'-biphenyl-4-yl)propanoic acid | 250 | Calculated (M − H)⁻ = 549.28; Found (M − H)⁻ = 549.16. |
| (3S)-3-{[2-(3-benzyl-5-methyl-2-oxopyridin-1(2H)-yl)hexanoyl]amino}-3-(4-chloro-3-isopropoxyphenyl)propanoic acid | 25 | Calculated (M − H)⁻ = 551.23; Found (M − H)⁻ = 551.20. |
| (3S)-3-{[2-(3-benzyl-5-methyl-2-oxopyridin-1(2H)-yl)hexanoyl]amino}-3-(4'-methoxy-1,1'-biphenyl-4-yl)propanoic acid | 300 | Calculated (M − H)⁻ = 565.27; Found (M − H)⁻ = 565.21. |

TABLE 4-continued

| Compound | IC₅₀ (nM) | Mass Spectral Data (m/z) |
|---|---|---|
| (3S)-3-{[2-(3-benzyl-5-methyl-2-oxopyridin-1(2H)-yl)hexanoyl]amino}-3-(4-methoxy-3-methylphenyl)propanoic acid | 9 | Calculated (M − H)⁻ = 503.25; Found (M − H)⁻ = 503.20. |
| (3S)-3-{[2-(3-benzyl-5-methyl-2-oxopyridin-1(2H)-yl)hexanoyl]amino}-3-phenylpropanoic acid | 10 | Calculated (M − H)⁻ = 459.23; Found (M − H)⁻ = 459.18. |
| (3S)-3-{[2-(3-benzyl-5-methyl-2-oxopyridin-1(2H)-yl)hexanoyl]amino}-3-(2,5-dimethylphenyl)propanoic acid | 300 | Calculated (M − H)⁻ = 487.26; Found (M − H)⁻ = 487.21. |
| (3S)-3-({2-[3-(2-chlorobenzyl)-5-methyl-2-oxopyridin-1(2H)-yl]hexanoyl}amino)-3-(4-methylphenyl)propanoic acid | 15 | Calculated (M − H)⁻ = 507.21; Found (M − H)⁻ = 507.15. |
| (3S)-3-({2-[3-(2-chlorobenzyl)-5-methyl-2-oxopyridin-1(2H)-yl]hexanoyl}amino)-3-(3-isopropoxyphenyl)propanoic acid | 5 | Calculated (M − H)⁻ = 551.23; Found (M − H)⁻ = 551.20. |
| (3S)-3-({2-[3-(2-chlorobenzyl)-5-methyl-2-oxopyridin-1(2H)-yl]hexanoyl}amino)-3-phenylpropanoic acid | 12 | Calculated (M − H)⁻ = 493.19; Found (M − H)⁻ = 493.12. |
| (3S)-3-{[2-(3-benzyl-5-methyl-2-oxopyridin-1(2H)-yl)hexanoyl]amino}-3-(3,5-difluorophenyl)propanoic acid | 25 | Calculated (M − H)⁻ = 495.21; Found(M − H)⁻ = 495.14. |
| (3S)-3-(2,3-dihydro-1H-inden-5-yl)-3-({2-5-methyl-2-oxo-3-(phenylmethyl)-1(2H)-pyridinyl]hexanoyl}amino)propanoic acid | 63 | Calculated(M − H)⁻ = 499.26; Found (M − H)⁻ = 499.23. |
| (3S)-3-({2-[3-[(2,3-dichlorophenyl)methyl]-5-methyl-2-oxo-1(2H)-pyridinyl]hexanoyl}amino)-3-{3-[(1-methylethyl)oxy]phenyl}propanoic acid | 68 | Calculated (M + H)⁺ = 586.20; Found (M + H)⁻ = 586.88. |
| (3S)-3-[1,1'-biphenyl]-3-yl-3-({2-[5-methyl-2-oxo-3-(phenylmethyl)-1(2H)-pyridinyl]hexanoyl}amino)propanoic acid | 250 | Calculated (M − H)⁻ = 535.26; Found (M − H)⁻ = 535.22. |
| (3S)-3-({2-[3-{[2,4-dichloro-6-(methyloxy)phenyl]methyl}-5-methyl-2-oxo-1(2H)-pyridinyl]hexanoyl}amino)-3-{3-[(1-methylethyl)oxy]phenyl}propanoic acid | 275 | Calculated (M + H)⁺ = 616.21; Found (M + H)⁺ = 616.88. |
| (3S)-3-(4-ethylphenyl)-3-({2-[5-methyl-2-oxo-3-(phenylmethyl)-1(2H)-pyridinyl]hexanoyl}amino)propanoic acid | 40 | Calculated (M − H)⁻ = 487.26; Found (M − H)⁻ = 487.24. |
| (3S)-3-[4-(1-methylethyl)phenyl]-3-({2-[5-methyl-2-oxo-3-(phenylmethyl)-1(2H)-pyridinyl]hexanoyl}amino)propanoic acid | 160 | Calculated (M − H)⁻ = 501.28; Found (M − H)⁻ = 501.27. |
| (3S)-3-(1-methyl-1H-indol-6-yl)-3-({2-[5-methyl-2-oxo-3-(phenylmethyl)-1(2H)-pyridinyl]hexanoyl}amino)propanoic acid | 10 | Calculated (M − H)⁻ = 512.25; Found (M − H)⁻ = 512.24. |
| (3S)-3-({2-[5-methyl-3-(2-naphthalenylmethyl)-2-oxo-1(2H)-pyridinyl]hexanoyl}amino)-3-(4-methylphenyl)propanoic acid | 400 | Calculated (M − H)⁻ = 523.26; Found (M − H)⁻ = 523.23. |
| (3S)-3-{3-[(1-methylethyl)oxy]phenyl}-3-({2-[5-methyl-3-(2-naphthalenylmethyl)-2-oxo-1(2H)-pyridinyl]hexanoyl}amino)propanoic acid | 20 | Calculated (M − H)⁻ = 567.29; Found (M − H)⁻ = 567.26. |
| (3S)-3-(2,3-dihydro-1H-inden-5-yl)-3-({2-[5-methyl-3-(2-naphthalenylmethyl)-2-oxo-1(2H)-pyridinyl]hexanoyl}amino)propanoic acid | 283 | Calculated (M − H)⁻ = 549.28; Found (M − H)⁻ = 549.21. |
| (3S)-3-({2-[5-methyl-3-(2-naphthalenylmethyl)-2-oxo-1(2H)-pyridinyl]hexanoyl}amino)-3-phenylpropanoic acid | 30 | Calculated (M − H)⁻ = 509.24; Found (M − H)⁻ = 509.19. |
| (2S)-2-({2-[5-methyl-2-oxo-3-phenylmethyl-1(2H)-pyridinyl]hexanoyl}amino)-3-phenylpropanoic acid | >10000 | Calculated (M − H)⁻ = 459.23; Found (M − H)⁻ = 459.22. |
| (3S)-3-({2-[5-methyl-2-oxo-3-(phenylmethyl)-1(2H)-pyridinyl]hexanoyl}amino)-3-[3-(2-methylpropyl)phenyl]propanoic acid | 10 | Calculated (M − H)⁻ = 515.29; Found (M − H)⁻ = 515.28. |
| (3S)-3-[3-(diethylamino)phenyl]-3-({2-[5-methyl-2-oxo-3-(phenylmethyl)-1(2H)-pyridinyl]hexanoyl}amino)propanoic acid | 10 | Calculated (M − H)⁻ = 530.30; Found (M − H)⁻ = 530.25. |
| (3S)-3-[3-(difluoromethyl)phenyl]-3-({2-[5-methyl-2-oxo-3-(phenylmethyl)-1(2H)-pyridinyl]hexanoyl}amino)propanoic acid | 20 | Calculated (M − H)⁻ = 509.23; Found (M − H)⁻ = 509.19. |
| (3S)-3-{3-[(1-methylethyl)oxy]phenyl}-3-{2-[5-methyl-3-[(2-methylphenyl)methyl]-2-oxo-1(2H)-pyridinyl]hexanoyl}amino)propanoic acid | 5 | Calculated (M + H)⁺ = 533.30; Found (M + H)⁺ = 532.94. |
| (2R)-2-({2-[5-methyl-2-oxo-3-(phenylmethyl)-1(2H)-pyridinyl]hexanoyl}amino)-3-phenylpropanoic acid | 5000 | Calculated (M − H)⁻ = 459.23; Found (M − H)⁻ = 459.22. |
| (3S)-3-(3-fluorophenyl)-3-({2-[5-methyl-2-oxo-3-(phenylmethyl)-1(2H)-pyridinyl]hexanoyl}amino)propanoic acid | 13 | Calculated (M − H)⁻ = 477.21; Found (M − H)⁻ = 477.20. |
| (2R)-2-({2-[5-methyl-2-oxo-3-(phenylmethyl)-1(2H)-pyridinyl]hexanoyl}amino)-2-phenylethanoic acid | >10000 | Calculated (M − H)⁻ = 445.21; Found (M − H)⁻ = 444.94. |
| (3S)-3-({2-[3-[(2-chloro-4-fluorophenyl)methyl]-5-methyl-2-oxo-1(2H)-pyridinyl]hexanoyl}amino)-3-{3-[(1-methylethyl)oxy]phenyl}propanoic acid | 17 | Calculated (M − H)⁻ = 569.22; Found (M − H)⁻ = 569.18. |
| (3S)-3-({2-[5-methyl-3-[(2-methylphenyl)methyl]-2-oxo-1(2H)-pyridinyl]hexanoyl}amino)-3-phenylpropanoic acid | 25 | Calculated (M + H)⁺ = 475.26; Found (M + H)⁺ = 474.94. |
| (3S)-3-{3-[(1-methylethyl)oxy]phenyl}-3-{2-[5-methyl-2-oxo-1-(phenylmethyl)-1,2-dihydro-3-pyridinyl]-2-phenylacetyl}amino)propanoic acid | 10 | Calculated (M + H)⁺ = 539.25; Found (M + H)⁺ = 538.91 |
| (3S)-3-({2-[5-methyl-3-(1-naphthalenylmethyl)-2-oxo-1(2H)-pyridinyl]hexanoyl}amino)-3-phenylpropanoic acid | 350 | Calculated (M − H)⁻ = 509.24; Found (M − H)⁻ = 509.22. |

TABLE 4-continued

| Compound | IC$_{50}$ (nM) | Mass Spectral Data (m/z) |
|---|---|---|
| (3S)-3-{3-[(1-methylethyl)oxy]phenyl}-3-({2-[5-methyl-3-(1-naphthalenylmethyl)-2-oxo-1(2H)-pyridinyl]hexanoyl}amino)propanoic acid | 67 | Calculated (M − H)⁻ = 567.29; Found (M − H)⁻ = 567.28. |
| (3S)-3-{4-methyl-3-[(1-methylethyl)oxy]phenyl}-3-({2-[5-methyl-2-oxo-3-(phenylmethyl)-1(2H)-pyridinyl]hexanoyl}amino)propanoic acid | 15 | Calculated (M − H)⁻ = 531.29; Found (M − H)⁻ = 531.26. |

SEQUENCE LISTING

```
<160> NUMBER OF SEQ ID NOS: 1

<210> SEQ ID NO 1
<211> LENGTH: 26
<212> TYPE: PRT
<213> ORGANISM: Homo sapiens

<400> SEQUENCE: 1

Cys Asp Glu Leu Pro Gln Leu Val Thr Leu Pro His Pro Asn Leu His
1               5                   10                  15

Gly Pro Glu Ile Leu Asp Val Pro Ser Thr
            20                  25
```

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:

1. A compound of the structure

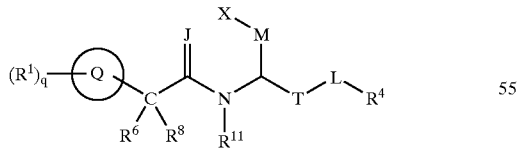

wherein circle Q represents a 2-pyridinone or 2-pyrimidone group;

q is an integer of zero to six;

M is selected from the group consisting of —C(R$^9$)(R$^{10}$)— and —(CH$_2$)$_u$—, wherein u is an integer of from 0 to 3;

J is selected from the group consisting of —O—, —S— and —NR$^{12}$—;

T is selected from the group consisting of —C(O)— and —(CH$_2$)$_b$— wherein b is an integer of from 0 to 3;

L is selected from the group consisting of —O—, —NR$^{13}$—, —S—, and —(CH$_2$)$_v$— wherein v is an integer of 0 or 1;

X is selected from the group consisting of —CO$_2$B, —PO$_3$H$_2$, —SO3H, —SO$_2$NH$_2$, —SO$_2$NHCOR$^{14}$, —OPO$_3$H$_2$, —C(O)NHC(O)R$^{15}$, —C(O)NHSO$_2$R$^{16}$, tetrazolyl, oxazolyl and hydroxyl;

R$^{11}$, R$^{12}$ and R$^{13}$ are each independently selected from the group consisting of hydrogen, alkyl, alkenyl, alkynyl, hydroxyalkyl, aliphatic acyl, alkynylamino, alkoxycarbonyl, heterocycloyl, —CH═NOH, haloalkyl, alkoxyalkyl, carboxaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups;

B, R$^1$, R$^6$, R$^8$, R$^9$, R$^{10}$, R$^{14}$, R$^{15}$ and R$^{16}$ at each occurrence are independently selected from the group consisting of hydrogen, halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, N(C$_1$-C$_3$ alkyl)—C(O)C$_1$-C$_3$ alkyl), —NHC(O)N(C$_1$-C$_3$ alkyl)C(O)—NH(C$_1$-C$_3$ alkyl), —NHC(O)NH(C$_1$-C$_6$ alkyl), —NHSO$_2$(C$_1$-C$_3$ alkyl), —NHSO$_2$(aryl), alkoxyalkyl, alkylamino, alkenylamino, di(C$_1$-C$_3$) amino, —C(O)O—(C$_1$-C$_3$)alkyl, —C(O)NH—(C$_1$-C$_3$)alkyl, —C(O)N(C$_1$-C$_3$ alkyl)$_2$, —CH═NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$alkyl), —SO$_3$—(C$_1$-C$_3$ alkyl), sulfonamido, carbamate, aryloxyalkyl and —C(O)NH(benzyl) groups; and R$^4$ is selected from the group consisting of hydrogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)—C(O)(C$_1$-C$_3$ alkyl), —NHC(O)N(C$_1$-C$_3$ alkyl)C(O)—NH(C$_1$-C$_3$ alkyl), —NHC(O)NH(C$_1$-C$_6$ alkyl), —NHSO$_2$(C$_1$-C$_3$ alkyl), —NHSO$_2$(aryl), alkoxyalkyl, alkylamino, alkenylamino, di(C$_1$-C$_3$)amino, —C(O)O—(C$_1$-C$_3$)alkyl, —C(O)NH—(C$_1$-C$_3$)alkyl, —C(O)N(C$_1$-C$_3$ alkyl)$_2$, —CH=NOH, —PO$_3$H$_2$, —OPO$_3$H$_2$, alkoxyalkoxy, carboxaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, carbamate, aryloxyalkyl and —C(O)NH(benzyl) groups;

wherein B, R$^1$, R$^4$, R$^6$, R$^8$, R$^9$, R$^{10}$, R$^{11}$, R$^{12}$, R$^{13}$, R$^{14}$, R$^{15}$ and R$^{16}$ are unsubs or substituted with at least one electron donating or electron withdrawing group;

wherein when L is —NR$^{13}$—, R$^4$ and R$^{13}$ taken together may form a ring;

and wherein at least one of R$^6$ and R$^8$ must be other than hydrogen;

and wherein when M is —C(R$^9$)(R$^{10}$)—, R$^9$ and R$^{10}$ taken together may form a ring;

or a pharmaceutically acceptable salt thereof.

2. A compound of the structure

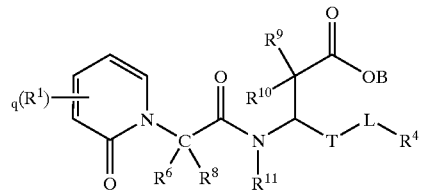

wherein q is an integer of zero to four;

T is selected from the group consisting of C(O) and (CH$_2$)$_b$ wherein b is an integer of 0 to 3;

L is selected from the group consisting of O, NR$^{13}$, S, and (CH$_2$)$_n$ wherein n is an integer of 0 or 1;

R$^{11}$ and R$^{13}$ are each independently selected from the group consisting of hydrogen, alkyl, alkenyl, alkynyl, hydroxyalkyl, aliphatic acyl, alkynylamino, alkoxycarbonyl, heterocycloyl, —CH=NOH, haloalkyl, alkoxyalkyl, carboxaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups;

B, R$^1$, R$^6$, R$^8$, R$^9$ and R$^{10}$ at each occurrence are each independently selected from the group consisting of hydrogen, halogen, alkyl, alkenyl, alkynyl, alkoxy, alkenoxy, alkynoxy, thioalkoxy, hydroxyalkoxy, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)—C(O) C$_1$-C$_3$ alkyl), —NHC(O)N(C$_1$-C$_3$ alkyl)C(O)NH (C$_1$-C$_3$ alkyl), —NHC(O)NH(C$_1$-C$_6$ alkyl), —NHSO$_2$(C$_1$-C$_3$ alkyl), —NHSO$_2$(aryl), alkoxyalkyl, alkylamino, alkenylamino, di(C$_1$-C$_3$)amino, —C(O) O—(C$_1$-C$_3$)alkyl, —C(O)NH(C$_1$-C$_3$)alkyl, —C(O)N (C$_1$-C$_3$ alkyl)$_2$, —CH=NOH, —PO$_3$H$_2$, —OPO$_3$H$_2$, haloalkyl, alkoxyalkoxy, carboxyaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO2—(C$_1$-C$_3$ alkyl), —SO$_3$—(C$_1$-C$_3$ alkyl), sulfonamido, carbamate, aryloxyalkyl and —C(O)NH (benzyl) groups; and R$^4$ is selected from the group consisting of hydrogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)—C(O)C$_1$-C$_3$ alkyl), —NHC(O)N (C$_1$-C$_3$ alkyl)C(O)—NH(C$_1$-C$_3$alkyl), —NHC(O)NH (C$_1$-C$_6$ alkyl), —NHSO$_2$(C$_1$-C$_3$ alkyl), —NHSO$_2$ (aryl), alkoxyalkyl, alkylamino, alkenylamino, di(C$_1$-C$_3$)amino, —C(O)O—(C$_1$-C$_3$)alkyl, —C(O) NH—(C$_1$-C$_3$)alkyl, —C(O)N(C$_1$-C$_3$ alkyl)$_2$, —CH=NOH, —PO$_3$H$_2$, —OPO$_3$H$_2$, alkoxyalkoxy, carboxaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, carbamate, aryloxyalkyl and —C(O)NH(benzyl) groups;

wherein B, R$^1$, R$^4$, R$^6$, R$^8$, R$^9$, R$^{10}$, R$^{11}$ and R$^{13}$ are unsubstituted or substituted with at least one electron donating or electron withdrawing group; and wherein when L is —NR$^{13}$—, R$^4$ and R$^{13}$ taken together may form a ring; and wherein at least one of R$^6$ and RS must be other than hydrogen; and wherein R$^9$ and R$^{10}$ taken together may form a ring;

or a pharmaceutically acceptable salt thereof.

3. The compound of claim 2 wherein q is one or two; R$^1$ at each occurrence is independently selected from the group consisting of aralkyl and alkyl; R$^6$ is alkyl; B, R$^8$, R$^9$, R$^{10}$ and R$^{11}$ are each independently hydrogen, T is —(CH$_2$)$_b$— wherein b is zero; L is —(CH$_2$)$_n$— wherein n is zero and R$^4$ is aryl.

4. A compound of the structure

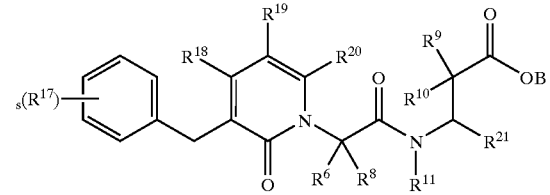

wherein s is an integer of zero to five;

R$^{21}$ is selected from the group consisting of aryl, heterocyclic aromatic, alkyheterocyclyl, heterocyclylalkyl, heterocycloyl, aralkyl, alkylaryl, alkyl, aroyl, aryloxy, cycloalkyl, cycloalkenyl, cycloalkynyl, biaryl, arylamino, thioaryl and diarylamino;

B, R$^6$, R$^8$, R$^9$, R$^{10}$, R$^{17}$, R$^{18}$, R$^{19}$ and R$^{20}$ at each occurrence are each independently selected from the group consisting of hydrogen, halogen, alkyl, alkenyl, alkynyl, alkoxy, alkenoxy, alkynoxy, thioalkoxy, hydroxyalkoxy, aliphatic acyl, —CF$_3$, —CO$_2$H, —SH, —CN, NO$_2$, —NH$_2$, —OH, alkynylamino, alkoxycarbonyl, heterocycloyl, carboxy, —N($C_1$-$C_3$ alkyl)—C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —NHSO$_2$($C_1$-$C_3$ alkyl), —NHSO$_2$(aryl), alkoxyalkyl, alkylamino, alkenylamino, di($C_1$-$C_3$) amino, —C(O)O—($C_1$-$C_3$)alkyl, —C(O)NH($C_1$-$C_3$) alkyl, —C(O)N($C_1$-$C_3$ alkyl)$_2$, —CH=NOH, —PO$_3$H$_2$, —OPO$_3$H$_2$, haloalkyl, alkoxyalkoxy, carboxyaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$-$C_3$ alkyl), —SO$_3$—($C_1$-$C_3$ alkyl), sulfonamido, carbamate, aryloxyalkyl and —C(O)NH(benzyl) groups; $R^{11}$ is selected from the group consisting of hydrogen, alkyl, alkenyl, alkynyl, hydroxyalkyl, aliphatic acyl, alkynylamino, alkoxycarbonyl, heterocycloyl, —CH=NOH, haloalkyl, alkoxyalkyl, carboxaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups; and, wherein B, $R^6$, $R^8$, $R^9$, $R^{10}$, $R^{11}$, $R^{17}$, $R^{18}$, $R^{19}$, $R^{20}$ and $R^{21}$ are unsubstituted or substituted with at least one electron donating or electron withdrawing group;

and wherein at least one of $R^6$ and $R^8$ must be other than hydrogen;

and wherein $R^9$ and $R^{10}$ taken together may form a ring;

and wherein $R^{18}$ and $R^{19}$ taken together may form a ring;

and wherein $R^{19}$ and $R^{20}$ taken together may form a ring; or a pharmaceutically acceptable salt thereof.

5. The compound of claim 4 wherein B, $R^8$, $R^9$, $R^{10}$, $R^{11}$, $R^{18}$ and $R^{20}$ are each independently hydrogen, $R^6$ and $R^{19}$ are each independently alkyl; s is an integer of zero to three; $R^{17}$ at each occurrence is independently selected from the group consisting of halogen, alkyl, haloalkyl, —CF$_3$, alkoxy and —OH; and $R^{21}$ is aryl.

6. The compound of claim 4 wherein s is zero; $R^6$ is butyl; B, $R^8$, $R^9$, $R^{10}$, $R^{11}$, $R^{18}$ and $R^{20}$ are each independently hydrogen; and $R^{21}$ is 1,3-benzodioxol-5-yl.

7. A compound of the structure

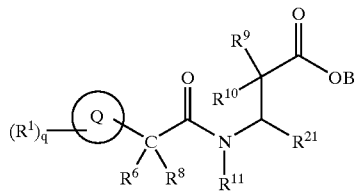

wherein circle Q is a ring selected from the group consisting of

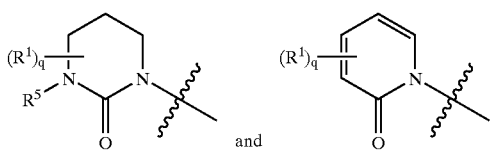

q is an integer of zero to four;

B, $R^1$, $R^6$, $R^8$, $R^9$ and $R^{10}$ are each independently selected from the group consisting of hydrogen, halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, NO$_2$, —NH$_2$, —OH, alkynylamino, alkoxycarbonyl, heterocycloyl, carboxy, —N($C_1$-$C_3$ alkyl)—C(O)$C_1$-$C_3$ alkyl), —NHC(O)NH ($C_1$-$C_3$ alkyl), —NHC(O)N($C_1$-$C_3$ alkyl)C(O)NH ($C_1$-$C_3$ alkyl), —NHSO$_2$($C_1$-$C_3$ alkyl), —NHSO$_2$ (aryl), alkoxyalkyl, —$C_1$-$C_3$ alkylamino, alkenylamino, alkynylamino, di($C_1$-$C_3$ alkyl)amino, —C(O)O—($C_1$-$C_3$ alkyl), —C(O)NH—($C_1$-$C_3$ alkyl), —CH=NOH, —PO$_3$H$_2$, —OPO$_3$H$_2$, —C(O)N($C_1$-$C_3$ alkyl)$_2$, haloalkyl, alkoxyalkoxy, carboxaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$-$C_3$ alkyl),—SO$_3$—($C_1$-$C_3$ alkyl), sulfonamido, aryloxyalkyl, carboxyl, carbamate and —C(O)NH(benzyl);

$R^5$ and $R^{11}$ are each independently selected from the group consisting of hydrogen, alkyl, alkenyl, alkynyl, hydroxyalkyl, aliphatic acyl, alkynylamino, alkoxycarbonyl, heterocycloyl, —CH=NOH, haloalkyl, alkoxyalkyl, carboxaldehyde, carboxamide, cycloalkyl, cycloalkenyl, cycloalkynyl, cycloalkylalkyl, aryl, heterocyclic aromatic, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl and —C(O)NH(benzyl) groups; and, $R^{21}$ is selected from the group consisting of aryl, heterocyclic aromatic, alkyheterocyclyl, heterocyclylalkyl, heterocycloyl, aralkyl, alkylaryl, alkyl, aroyl, aryloxy, cycloalkyl, cycloalkenyl, cycloalkynyl, biaryl, arylamino, thioaryl and diarylamino;

wherein B, $R^1$, $R^5$, $R^6$, R $R^9$, $R^{10}$, $R^{11}$ and $R^{21}$ are unsubstituted or substituted with at least one electron donating or electron withdrawing group;

and wherein at least one of $R^6$ and RS must be other than hydrogen;

and wherein $R^9$ and $R^{11}$ taken together may form a ring; or a pharmaceutically acceptable salt thereof.

8. The compound of claim 7 wherein B, $R^6$, $R^8$, $R^9$, $R^{10}$ and $R^{11}$ are each independently selected from the group consisting of hydrogen and alkyl, $R^1$ and $R^5$, at each occurrence, are independently selected from the group consisting of hydrogen, 2-thienylmethyl, benzyl and methyl and $R^{21}$ is aryl.

9. A compound selected from the group consisting of (3S)-(1,3-benzodioxol-5-yl)-3-(((2S)-2-(2-oxo-3-(2-thienylmethyl)tetrahydro-1(2H)-pyrimidinyl)hexanoyl) amino) propanoic acid, (3S)-3-(1,3-benzodioxol-5-yl)-3-((2R, S)-2-(3-benzyl-5-methyl-2-oxo-1(2H)-pyridinyl) hexanoylamino)propanoic acid, (3S)-3-(1,3-benzodioxol-5-yl)-3-((2R,S)-2-(3-(3-chlorobenzyl)-5-methyl-2-oxo-1(2H)-pyridinyl)hexanoylamino)propanoic acid, (3S)-3-(1,3-benzodioxol-5-yl)-3-(((2S)-2-(2-oxo-3-(phenylmethyl)-1 (2H)-pyridinyl)hexanoyl)amino) propanoic acid, (3S)-3-(1, 3-benzodioxol-5-yl)-3-((2-(3-chlorophenyl)methyl)-5-methyl-2-oxo-1(2H)-pyridinyl)hexanoyl)amino)propanoic acid, (3S)-3-{[(2S)-2-(3-benzyl-5-methyl-2-oxopyridin-1 (2H)-yl)hexanoyl]amino}-3-(3,5-dimethoxyphenyl) propanoic acid, (3S)-3-{[(2S)-2-(3-benzyl-5-methyl-2- oxopyridin-1(2H)-yl)hexanoyl]amino}-3-(3-fluoro-4-methoxyphenyl)propanoic acid, (3S)-3-{[2-(3-benzyl-5-methyl-2-oxopyridin-1(2H)-yl)hexanoyl]amino }-3-(3-isopropoxyphenyl)propanoic acid, (3S)-3-({2-[3-(3-chlorobenzyl)-5-methyl-2-oxopyridin-1(2H)-yl]hexanoyl}amino)-3-(3-isopropoxyphenyl)propanoic acid, (3S)-3-(3-isopropoxyphenyl)-3-({2-[3-(2-methoxybenzyl)-5-methyl-2-oxopyridin-1(2H)-yl]hexanoyl}amino)propanoic acid, (3S)-3-{[2-(3-benzyl-5-methyl-2-oxopyridin-1(2H)-yl)hexanoyl]amino}-3-(3-ethoxy-4-methoxyphenyl)propanoic acid, (3S)-3-{[2-(3-benzyl-5-methyl-2-oxopyridin-1(2H)-yl)hexanoyl]amino}-3-(4-methoxy-3-methylphenyl)propanoic acid, (3S)-3-{[2-(3-benzyl-5-methyl-2-oxopyridin-1(2H)-yl)bexanoyl]amino}-3-phenylpropanoic acid, (3S)-3-({2-[3-(2-chlorobenzyl)-5-methyl-2-oxopyridin-1(2H)-yl]hexanoyl}amino)-3-(4-methylphenyl)propanoic acid, (3S)-3-({2-[3-(2-chlorobenzyl)-5-methyl-2-oxopyridin-1(2H)-yl]hexanoyl}amino)-3-(3-isopropoxyphenyl)propanoic acid, (3S)-3-({2-[3-(2-chlorobenzyl)-5-methyl-2-oxopyridin-1(2H)-yl]hexanoyl}amino)-3-phenylpropanoic acid, (3S)-3-(1-methyl-1H-indol-6-yl)-3-((2-[5-methyl-2-oxo-3-(phenylmethyl)-1(2H)-pyridinyl]hexanoyl}amino)propanoic acid, (3S)-3-{3-[(1-methylethyl)oxy]phenyl}-3-({2-[5-methyl-3-(2-naphthalenylmethyl)-2-oxo-1(2H)-pyridinyl]hexanoyl}amino)propanoic acid, (3S)-3-({2-[5-methyl-2-oxo-3-(phenylmethyl)-1(2H)-pyridinyl]hexanoyl}amino)-3-[3-(2-methylpropyl)phenyl]propanoic acid, (3S)-3-[3-(difluoromethyl)phenyl]-3-({2-[5-methyl-2-oxo-3-(phenylmethyl)-1(2H)-pyridinyl]hexanoyl}amino)propanoic acid, (3S)-3-{3-[(1-methylethyl)oxy]phenyl}-3-({2-[5-methyl-3-[(2-methylphenyl)methyl]-2-oxo-1(2H)-pyridinyl]hexanoyl}amino)propanoic acid, (3S)-3-(3-fluorophenyl)-3-({2-[5-methyl-2-oxo-3-(phenylmethyl)-1(2H)-pyridinyl]hexanoyl}amino)propanoic acid, (3S)-3-({2-[3-[(2-chloro-4-fluorophenyl)methyl]-5-methyl-2-oxo-1(2H)-pyridinyl]hexanoyl}amino)-3-{3-[(1-methylethyl)oxy]phenyl}propanoic acid and (3S)-3-{3-[(1-methylethyl)oxy]phenyl}-3-({2-[5-methyl-2-oxo-1-(phenylmethyl)-1,2-dihydro-3-pyridinyl]-2-phenylacetyl}amino)propanoic acid and pharmaceutically acceptable salts thereof.

10. A compound selected from the group consisting of (3S)-3-{[(2S)-2-(3-benzyl-5-methyl-2-oxopyridin-1(2H)-yl)hexanoyl]aamino}-3-(3 ',4'-dimethoxy-1,1'-biphenyl-4-yl)propanoic acid, (3S)-3-({(2S)-2-[3-(2-chlorobenzyl)-5-methyl-2-oxopyridin-1(2H)-yl]hexanoyl}amino)-3-(3',4'-dimethoxy-1,1'-biphenyl-4-yl)propanoic acid, (3S)-3-(1,1'-biphenyl-4-yl)-3-({(2S)-2-[3-(2-chloro-6-methylbenzyl)-5-methyl-2-oxopyridin-1(2H)-yl]hexanoyl}amino)propanoic acid, (3S)-3-{[(2S)-2-(3-benzyl-5-methyl-2-oxopyridin-1(2H)-yl)hexanoyl]amino}-3-(1,1 '-biphenyl-4-yl)propanoic acid, (3S)-3-(1,1'-biphenyl-4-yl)-3-({(2S)-2-[3-(2-chlorobenzyl)-5-methyl-2-oxopyridin-1(2H)-yl]hexanoyl}amino)propanoic acid, (3S)-3-{[(2S)-2-(3-benzyl-5-methyl-2-oxopyridin-1(2H)-yl)hexanoyl]amino}-3-(4'-methyl-1,1'-biphenyl-4-yl)propanoic acid, (3S)-3-({(2S)-2-[3-(2-chlorobenzyl)-5-methyl-2-oxopyridin-1(2H)-yl]hexanoyl}amino)-3-(4'-methyl-1,1'-biphenyl-4-yl)propanoic acid, (3S)-3-({(2S)-2-[3-(2-chloro-6-methylbenzyl)-5-methyl-2-oxopyridin-1(2H)-yl]hexanoyl}amino)-3-(4'-methyl-1,1'-biphenyl-4-yl)propanoic acid, (3S)-3-{[(2S)-2-(3-benzyl-5-methyl-2-oxopyridin-1(2H)-yl)hexanoyl]amino}-3-(2',6'-dimethoxy-1,1'-biphenyl-4-yl)propanoic acid, (3S)-3-({(2S)-2-[3-(2-chlorobenzyl)-5-methyl-2-oxopyridin-1(2H)-yl]hexanoyl}amino)-3-(2',6'-dimethoxy-1,1'-biphenyl-4-yl)propanoic acid, (3S)-3-({(2S)-2-[3-(2-chloro-6-methylbenzyl)-5-methyl-2-oxopyridin-1(2H)-yl]hexanoyl}amino)-3-(2',6'-dimethoxy-1,1'-biphenyl-4-yl)propanoic acid, (3S)-3-{[(2S)-2-(3-benzyl-5-methyl-2-oxopyridin-1(2H)-yl)hexanoyl]amino}-3-biphenyl-3-yl)propanoic acid, (3S)-3-(1,1'-biphenyl-3-yl)-3-({(2S)-2-[3-(2-chlorobenzyl)-5-methyl-2-oxopyridin-1(2H)-yl]hexanoyl}amino)propanoic acid, (3S)-3-(1,1'-biphenyl-3-yl)-3-({(2S)-2-[3-(2-chloro-6-methylbenzyl)-5-methyl-2-oxopyridin-1(2H)-yl]hexanoyl}amino)propanoic acid, (3S)-3-{[(2S)-2-(3-benzyl-5-methyl-2-oxopyridin-1(2H)-yl)hexanoyl]amino}-3-(2'-methoxy-1,1'-biphenyl-3-yl)propanoic acid, (3S)-3-({(2S)-2-[3-(2-chlorobenzyl)-5-methyl-2-oxopyridin-1(2H)-yl]hexanoyl}amino)-3-(2'-methoxy-1,1'-biphenyl-3-yl)propanoic acid, (3S)-3-({(2S)-2-[3-(2-chloro-6-methylbenzyl)-5-methyl-2-oxopyridin-1(2H)-yl]hexanoyl}amino)-3-(2'-methoxy-1,1'-biphenyl-3-yl)propanoic acid, (3S)-3-({(2S)-2-[3-(2-fluoro-6-methoxybenzyl)-5-methyl-2-oxopyridin-1(2H)-yl]hexanoyl}amino)-3-(4-methylphenyl)propanoic acid, (3S)-3-({(2S)-2-[3-(2,6-dimethylbenzyl)-5-methyl-2-oxopyridin-1(2H)-yl]hexanoyl}amino)-3-(4-methylphenyl)propanoic acid, (3S)-3-({(2S)-2-[3-(3,5-dimethylbenzyl)-5-methyl-2-oxopyridin-1(2H)-yl]hexanoyl}amino)-3-(4-methylphenyl)propanoic acid, (3S)-3-({(2S)-2-[3-(2,6-dichlorobenzyl)-5-methyl-2-oxopyridin-1(2H)-yl]hexanoyl}amino)-3-(4-methylphenyl)propanoic acid, (3S)-3-({(2S)-2-[3-(2-chloro-6-fluorobenzyl)-5-methyl-2-oxopyridin-1(2H)-yl]hexanoyl}amino)-3-(4-methylphenyl)propanoic acid, (3S)-3-({(2S)-2-[3-(2,6-difluorobenzyl)-5-methyl-2-oxopyridin-1(2H)-yl]hexanoyl}amino)-3-(4-methylphenyl)propanoic acid, (3S)-3-(1,3-benzodioxol-5-yl)-3-({(2S)-2-[3-(2,6-difluorobenzyl)-5-methyl-2-oxopyridin-1(2H)-yl]hexanoyl}amino)propanoic acid, (3S)-3-(1,3-benzodioxol-5-yl)-3-({(2S)-2-[3-(2-chloro-6-fluorobenzyl)-5-methyl-2-oxopyridin-1(2H)-yl]hexanoyl}amino)propanoic acid, (3S)-3-(1,3-benzodioxol-5-yl)-3-({(2S)-2-[3-(2,6-dichlorobenzyl)-5-methyl-2-oxopyridin-1(2H)-yl]hexanoyl}amino)propanoic acid, (3S)-3-(1,3-benzodioxol-5-yl)-3-({(2S)-2-[3-(2,6-dimethylbenzyl)-5-methyl-2-oxopyridin-1(2H)-yl]hexanoyl}amino)propanoic acid, (3S)-3-(1,3-benzodioxol-5-yl)-3-({(2S)-2-[3-(3,5-dimethylbenzyl)-5-methyl-2-oxopyridin-1(2H)-yl]hexanoyl}amino)propanoic acid, (3S)-3-(1,3-benzodioxol-5-yl)-3-({(2S)-2-[3-(2-fluoro-6-methoxybenzyl)-5-methyl-2-oxopyridin-1(2H)-yl]hexanoyl}amino)propanoic acid, (3S)-3-({(2S)-2-[3-(2-chlorobenzyl)-5-methyl-2-oxopyridin-1(2H)-yl]hexanoyl}amino)-3-(3,4-diethoxyphenyl)propanoic acid, (3S)-3-(3,4-diethoxyphenyl)-3-({(2S)-2-[3-(2,6-difluorobenzyl)-5-methyl-2-oxopyridin-1(2H)-yl]hexanoyl}amino)propanoic acid, (3S)-3-({(2S)-2-[3-(2,6-difluorobenzyl)-5-methyl-2-oxopyridin-1(2H)-yl]hexanoyl}amino)-3-(3-ethoxyphenyl)propanoic acid, (3S)-3-({(2S)-2-[3-(2-chloro-6-fluorobenzyl)-5-methyl-2-oxopyridin-1(2H)-yl]hexanoyl}amino)-3-(3-ethoxyphenyl)propanoic acid, (3S)-3-({(2S)-2-[3-(2-chlorobenzyl)-5-methyl-2-oxopyridin-1(2H)-yl]-3-methylbutanoyl}amino)-3-(4-methylphenyl)propanoic acid, (3S)-3-({(2S)-2-[3-(2-chlorobenzyl)-5-methyl-2-oxopyridin-1(2H)-yl]4-methylpentanoyl}amino)-3-(4-methylphenyl)propanoic acid, (3S)-3-(1,3-benzodioxol-5-yl)-3-({(2S)-2-[3-(2-chlorobenzyl)-5-methyl-2-oxopyridin-1(2H)-yl]-4-methylpentanoyl}amino)propanoic acid, (3S)-3-(1,3-benzodioxol-5-yl)-3-({(2S)-2-[3-(2-chlorobenzyl)-5-methyl-2-oxopyridin-1(2H)-yl]-3-methylbutanoyl}amino)propanoic acid, (3S)-3-(1,3-benzodioxol-5-yl)-3-({(2S)-2-[3-(2-chlorobenzyl)-5- methyl-2-oxopyridin-1(2H)-yl]-3-phenylpropanoyl}amino)propanoic acid, (3S)-3-({(2S)-2-[3-(2-chlorobenzyl)-5-methyl-2-oxopyridin-1(2H)-yl]-3-phenylpropanoyl}-amino)-3-(4-methylphenyl)propanoic acid, (3S)-3-(1,3-benzodioxol-5-yl)-3-(((2R)-2-(1-benzyl-5-methyl-2-oxo-1,2-dihydropyridin-3-yl)hexanoyl)amino)propanoic acid and pharmaceutically acceptable salts thereof.

11. (3S)-3-(1,3-benzodioxol-5-yl)-3-((2S)-2-(3-benzyl-5-methyl-2-oxo-1(2H)-pyridinyl)hexanoylamino)propanoic acid or a pharmaceutically acceptable salt thereof.

12. A pharmaceutical composition comprising:
a compound of claim 1;
in a pharmaceutically acceptable carrier.

13. A method for treating a disease state selected from the group consisting of asthma, multiple sclerosis, arthritis, inflammatory bowel disease, contact hypersensitivity, cardiac allograft rejection and diabetes in a mammal comprising administering to said mammal a therapeutic amount of a compound of claim 1.

* * * * *